US009814769B2

(12) United States Patent
Ghunaim et al.

(10) Patent No.: US 9,814,769 B2
(45) Date of Patent: Nov. 14, 2017

(54) **VACCINES AGAINST PATHOGENIC *ESCHERICHIA COLI* AND METHODS OF USING THE SAME**

(71) Applicant: QATAR UNIVERSITY, Doha (QA)

(72) Inventors: Haitham Tawfiq Ghunaim, Al-Sadd (QA); Marawan A. Abu Madi, Doha (QA); Andrew Potter, Saskatoon (CA); Brenda Allan, Saskatoon (CA)

(73) Assignee: QATAR UNIVERSITY, Doha (QA)

( * ) Notice: Subject to any disclaimer, the term of this patent is extended or adjusted under 35 U.S.C. 154(b) by 0 days.

(21) Appl. No.: 14/872,044

(22) Filed: Sep. 30, 2015

(65) Prior Publication Data

US 2016/0106826 A1 Apr. 21, 2016

Related U.S. Application Data

(60) Provisional application No. 62/057,857, filed on Sep. 30, 2014.

(51) Int. Cl.

| | |
|---|---|
| ***A61K 39/108*** | (2006.01) |
| ***C07K 14/245*** | (2006.01) |
| ***C07K 14/285*** | (2006.01) |
| ***A61K 39/102*** | (2006.01) |
| *A61K 39/00* | (2006.01) |

(52) U.S. Cl.

CPC ........ *A61K 39/0258* (2013.01); *A61K 39/102* (2013.01); *C07K 14/245* (2013.01); *C07K 14/285* (2013.01); *A61K 2039/53* (2013.01); *A61K 2039/541* (2013.01); *A61K 2039/552* (2013.01); *C07K 2319/55* (2013.01)

(58) Field of Classification Search

CPC ............................. C12Q 1/6837; C12Q 1/689; C12Q 2565/513; C07K 14/245; C07K 2319/00; C07K 14/285; C07K 2319/55; A61K 39/00; A61K 39/0258; A61K 2039/53; A61K 2039/541; A61K 2039/552; A61K 39/102

See application file for complete search history.

(56) References Cited

U.S. PATENT DOCUMENTS

| | | | | |
|---|---|---|---|---|
| 4,281,061 A * | 7/1981 | Zuk | G01N 33/542 435/188 |
| 5,352,448 A | 10/1994 | Bowersock et al. | |
| 5,837,268 A * | 11/1998 | Potter | A61K 47/48238 424/184.1 |
| 5,871,750 A * | 2/1999 | Potter | C07K 14/285 424/184.1 |
| 6,500,434 B1 * | 12/2002 | Langermann | A61K 39/0258 424/184.1 |
| 6,610,307 B1 | 8/2003 | Prideaux et al. | |
| 6,846,477 B2 | 1/2005 | Keich et al. | |
| 2008/0311138 A1 | 12/2008 | De Magistris | |
| 2010/0285135 A1 | 11/2010 | Wendorf | |
| 2011/0223197 A1 | 9/2011 | Vajdy | |
| 2012/0064151 A1 | 3/2012 | Abraham | |
| 2012/0107322 A1 | 5/2012 | Scarselli et al. | |
| 2012/0308600 A1 | 12/2012 | Costantino et al. | |

FOREIGN PATENT DOCUMENTS

| | | |
|---|---|---|
| CA | 2081950 | 5/1993 |
| JP | 2008-231123 | 10/2008 |
| JP | 2011-234721 | 11/2011 |
| WO | WO 99/56755 | * 11/1999 |
| WO | WO 2011/080595 | 7/2011 |

OTHER PUBLICATIONS

Kariyawasam et al Veterinary Microbiology. 2004; 98:273-284.*

Kariyawasam et al , Avian Dis. Jul.-Sep. 2002;46(3):668-78.*

Haitham Tawfiq 2005. Masters Abstracts International, (2005) vol. 44, No. 2; 1- 138 pages.*

Klemm et al ( Journal of Bacteriology, Jan. 1996, pp. 61-67).*

Marklund et al (Molecular Microbiology, V. 6, (16) 2006).*

Acres, S D et al. "Immunization of Calves Against Enterotoxigenic Colibacillosis by Vaccinating Dams with Purified K99 Antigen and Whole Cell Bacterins," Infection and Immunity, Jul. 1979, pp. 121-126.

Agricultural Research Service, "Construction of Live Mucosal and Injectable Bacterial Vaccines Against Avian and Bovine Respiratory Diseases," Accessed May 22, 2014 <http://portal.nifa.usda.gov/web/crisprojectpages/0406786-construction-of-live-mucosal-and-injectable-bacterial-vaccines-against-avian-and-bovine-respiratory-diseases.html>.

Ghunaim, Haitham et al., "Advances in vaccination against avian pathogenic *Escherichia coli* respiratory disease: Potentials and limitations," Veterinary Microbiology, vol. 172, Issues 1-2, Aug. 6, 2014, pp. 13-22.

Gupta, Satish et al. "Antigens specificities and characterization of antibodies against major periodontopathic bacteria: Aggregatibacter actinomycetemcomitans and Porphyromonas gingivalis," J Cranio Max Dis, 2014; 3, pp. 32-42.

Meeusen, Els N. "Exploiting mucosal surfaces for the development of mucosal vaccines," Vaccine, vol. 29, Issue 47, Nov. 3, 2011, pp. 8506-8511.

* cited by examiner

*Primary Examiner* — Padmavathi Baskar

(74) *Attorney, Agent, or Firm* — Squire Patton Boggs (US) LLP

(57) ABSTRACT

Provided herein are compositions and methods for vaccinating against infection with pathogenic *Escherichia coli* (*E. coli*). In some embodiments, the compositions may include a vaccine including an immunogenic portion of at least two *E. coli* proteins described herein.

5 Claims, 10 Drawing Sheets

SEQUENCE LISTING

<160> NUMBER OF SEQ ID NOS: 30

<210> SEQ ID NO 1
<211> LENGTH: 3356
<212> TYPE: DNA
<213> ORGANISM: Escherichia coli
<220> FEATURE:
<221> NAME/KEY: misc_feature
<222> LOCATION: (1)..(3356)
<223> OTHER INFORMATION: Escherichia coli fimD, fimF, fimG, fimH, uxaA
      and gntP

<400> SEQUENCE: 1

```
gcgcgcgttg ggataaaact gctcatgacg ctaacccaca ataataagcc gctgccgttt     60

ggggcgatgg tgacatcaga gagtagccag agtagcggca ttgttgcgga taatggtcag    120

gtttacctca gcggaatgcc tttagcggga aaagtgcagg tgaaatgggg agaagaggaa    180

aatgctcact gtgtcgccaa ttatcaactg ccaccagaga gtcagcagca gttattaacc    240

cagctatcag ctgaatgtcg ttaaggggc gtgatgagaa acaaaccttt ttatcttctt    300

tgcgcttttt tgtggctggc ggtaagtcac gctttggctg cggatagcac gattactatc    360

cgcggctatg tcagagataa tggctgtagt gtggccgctg aatcaaccaa ttttactgtt    420

gatctgatgg aaaacgcggc gaagcaattt aacaacattg gcgcgacgac tcctgttgtt    480

ccatttcgta ttttgctgtc accctgtggt aacgccgttt ctgccgtaaa ggttgggttt    540

accggcgttg cagatagcca caatgccaac ctgcttgcac ttgaaaatac ggtgtcagcg    600

gctgcgggac tgggaataca gcttctgaat gagcagcaaa atgagatacc ccttaatgcc    660

ccatcgtccg cgatttcgtg gacgaccctg acgccgggta aaccaaatac gttgaatttt    720

tacgcccggc taatggcgac acaggtgcct gtcactgcgg ggcatattaa tgccacggct    780

accttcactc ttgaatatca gtaactggag atgctcatga aatggtgcaa acgtgggtat    840

ttattggcgg caatgttggc gttcgcaagt gcgacgatac aggcagccga tgtcaccatc    900

acggtgaacg gtaaggtcgt cgccaaaccg tgcacagttt ccaccaccaa tgccacggta    960

gatctcggcg atctttattc tttcagtctt atgtctgccg ggcggcatc ggcctggcat   1020

gatgttgcgc ttgagttgac taattgtccg gtgggaacgt cgagggtcac tgccagcttc   1080

agcggggcag ccgacagtac cggatattat aaaaatcagg ggaccgcgca aaacatccag   1140

ttagagctac aggatgacag tggcaacaca ttgaatactg gcgcaaccaa aacagttcag   1200

gtggatgatt cctcacaatc agcgcacttc ccgttacagg tcagagcatt gaccgtaaat   1260
```

```
ggtggagcca ctcagggaac cattcaggca gtgattagca tcacctatac ctacagctga   1320

acccaaagag atgattgtaa tgaaacgagt tattaccctg tttgctgtac tgctgatggg   1380

ctggtcggta aatgcctggt cattcgcctg taaaaccgcc aatggtaccg caatccctat   1440

tggcggtggc agcgccaatg tttatgtaaa ccttgcgcct gccgtgaatg tggggcaaaa   1500

gctggtcgta gatctttcga cgcaaatctt ttgccataac gattacccag aaaccattac   1560

agactatgtc acactgcaac gaggttcggc ttatggcggc gtgttatcta gtttttccgg   1620

gaccgtaaaa tataatggca gtagctatcc tttccctact accagcgaaa cgccgcgggt   1680

tgtttataat tcgagaacgg ataagccgtg gccggtggcg ctttatttga cgccggtgag   1740

cagtgcgggg ggagtggcga ttaaagctgg ctcattaatt gccgtgctta ttttgcgaca   1800

gaccaacaac tataacagcg atgatttcca gtttgtgtgg aatatttacg ccaataatga   1860

tgtggtggtg cccactggcg gctgcgatgt ttctgctcgt gatgtcaccg ttactctgcc   1920

ggactaccct ggttcagtgc cgattcctct taccgtttat tgtgcgaaaa gccaaaacct   1980

ggggtattac ctctccggca caaccgcaga tgcgggcaac tcgattttca ccaataccgc   2040

gtcgttttca cccgcgcagg gcgtcggcgt acagttgacg cgcaacggta cgattattcc   2100

agcgaataac acggtatcgt taggagcagt agggacttcg gcggtaagtc tgggattaac   2160

ggcaaattac gcacgtaccg gagggcaggt gactgcaggg aatgtgcaat cgattattgg   2220

cgtgactttt gtttatcaat aaagaaatca cagggcattg ctaatgcagg tacgcaatat   2280

tacctgaagc taaaatctgc acgttagccc tttgtaggcc agataagacg cgtcagcgtc   2340

gcatctggca taaacaaagc gcactttacc gacaatccga acagagcctg ccaatggcag   2400

gctcaggtgc tcttttacgc taccatgcta ataatcagca caataatcag cccaaccacg   2460

gagttgacca gctccagcag accccaggtt ttcaacgtgt cttttactga caggtcaaag   2520

taatctaaga ggcattgcta atgtagggaa tgtgtctgaa cctgcggtca ttgtcagtac   2580

cagcatcagg ccaatgccga ataccaccca gagaatgtta agcacatgca taacgtttta   2640

ccttacctgg ttgaaccgtt gttattttgg gcgacatgtt atgtaaattg gtcaaccatt   2700

gttgcgatga atgtcacatc ctctgatcaa taaccatcga ttaccctttg ctgcaatttg   2760

cagcaacaac caggagagtg aaattcttgt gatgtggtta accaatttta gaattcgggt   2820

tgacatgtct taccaaaagg tagaacttat acgccatctc atccgatgca acgccacggc   2880

tgcggtctgg ttgttcatcc ggatacctaa acaactccgg ggctccacgt ctctttgctg   2940

tggaacccac tatgtgaaag aggaaaaatc atggaacaga cctggcgctg gtacggccca   3000

aacgatccgg tttctttagc tgatgtccgt caggcgggcg caactggcgt ggttaccgcg   3060

ctgcaccata tcccgaacgg cgaagtatgg tccgtagaag agatcctcaa acgcaaggcg   3120

atcgttgaag acgcaggcct ggtgtggtct gtcgttgaaa gcgtaccaat tcacgaagat   3180

atcaaaaccc acactggcaa ctatgagcag tggattgcta actatcagca gaccctgcgc   3240

aacctggcgc agtgcggcat tcgcaccgtg tgctacaact tcatgccggt gctcgactgg   3300

acccgtactg acctcgaata cgtgctgcca gacggctcca aagctctgcg cttcga        3356
```

<210> SEQ ID NO 2
<211> LENGTH: 300
<212> TYPE: PRT
<213> ORGANISM: Escherichia coli
<220> FEATURE:
<221> NAME/KEY: misc_feature
<222> LOCATION: (1)..(300)

<223> OTHER INFORMATION: Type 1 fimbriae adhesin, precursor polypeptide (FimH)

<400> SEQUENCE: 2

```
Met Lys Arg Val Ile Thr Leu Phe Ala Val Leu Leu Met Gly Trp Ser
1               5                   10                  15

Val Asn Ala Trp Ser Phe Ala Cys Lys Thr Ala Asn Gly Thr Ala Ile
            20                  25                  30

Pro Ile Gly Gly Gly Ser Ala Asn Val Tyr Val Asn Leu Ala Pro Ala
        35                  40                  45

Val Asn Val Gly Gln Lys Leu Val Val Asp Leu Ser Thr Gln Ile Phe
    50                  55                  60

Cys His Asn Asp Tyr Pro Glu Thr Ile Thr Asp Tyr Val Thr Leu Gln
65                  70                  75                  80

Arg Gly Ser Ala Tyr Gly Gly Val Leu Ser Ser Phe Ser Gly Thr Val
                85                  90                  95

Lys Tyr Asn Gly Ser Ser Tyr Pro Phe Pro Thr Thr Ser Glu Thr Pro
            100                 105                 110

Arg Val Val Tyr Asn Ser Arg Thr Asp Lys Pro Trp Pro Val Ala Leu
        115                 120                 125

Tyr Leu Thr Pro Val Ser Ser Ala Gly Gly Val Ala Ile Lys Ala Gly
    130                 135                 140

Ser Leu Ile Ala Val Leu Ile Leu Arg Gln Thr Asn Asn Tyr Asn Ser
145                 150                 155                 160

Asp Asp Phe Gln Phe Val Trp Asn Ile Tyr Ala Asn Asn Asp Val Val
                165                 170                 175

Val Pro Thr Gly Gly Cys Asp Val Ser Ala Arg Asp Val Thr Val Thr
            180                 185                 190

Leu Pro Asp Tyr Pro Gly Ser Val Pro Ile Pro Leu Thr Val Tyr Cys
        195                 200                 205

Ala Lys Ser Gln Asn Leu Gly Tyr Tyr Leu Ser Gly Thr Thr Ala Asp
    210                 215                 220

Ala Gly Asn Ser Ile Phe Thr Asn Thr Ala Ser Phe Ser Pro Ala Gln
225                 230                 235                 240

Gly Val Gly Val Gln Leu Thr Arg Asn Gly Thr Ile Ile Pro Ala Asn
                245                 250                 255

Asn Thr Val Ser Leu Gly Ala Val Gly Thr Ser Ala Val Ser Leu Gly
            260                 265                 270

Leu Thr Ala Asn Tyr Ala Arg Thr Gly Gly Gln Val Thr Ala Gly Asn
        275                 280                 285

Val Gln Ser Ile Ile Gly Val Thr Phe Val Tyr Gln
    290                 295                 300
```

<210> SEQ ID NO 3
<211> LENGTH: 1011
<212> TYPE: DNA
<213> ORGANISM: Escherichia coli
<220> FEATURE:
<221> NAME/KEY: misc_feature
<222> LOCATION: (1)..(1011)
<223> OTHER INFORMATION: E. coli papG gene for P-pili protein

<400> SEQUENCE: 3

```
atgaaaaaat ggttcccagc tttgttattt tccttgtgtg tgtctggtga gtcctctgca      60

tggaataata ttgtctttta ctcccttgga aacgttaact cttatcaggg agggaatgtg     120

gtgattactc aaaggccaca atttataact tcgtggcgcc cgggcattgc tacggtaacc     180
```

```
tggaatcagt gtaatggtcc tgggtttgct gatggttcct gggcttacta cagggagtat    240

attgcgtggg tagtattccc caaaaaggtt atgaccaaaa atggatatcc cttatttatt    300

gaggttcata ataaaggtag ctggagtgag gagaatactg gtgacaatga cagctatttt    360

tttctcaagg ggtataagtg ggatgagcgg gcctttgatg caggtaattt gtgtcagaaa    420

ccaggagaaa caacccgtct gactgagaaa tttgacgata ttatttttaa agtcgcccta    480

cctgcagatc ttcctttagg ggattattct gttacaattc catacacttc cggcatgcag    540

cgtcatttcg cgagttactt gggggcccgt tttaaaatcc catacaatgt ggccaaaact    600

ctcccaagag agaatgaaat gttattctta tttaagaata tcggcggatg ccgtccttct    660

gcacagtctc tggaaataaa gcatggtgat ctgtctatta atagcgctaa taatcattat    720

gcggctcaga ctctttctgt gtcttgcgat gtgcctgcaa atattcgttt tatgctgtta    780

agaaatacaa ctccgacata cagccatggt aagaaatttt cggttggtct ggggcatggc    840

tgggactcca ttgtttcggt taacggggtg gacacaggag agacaacgat gagatggtac    900

aaagcaggta cacaaaacct gaccatcggc agtcgcctct atggtgaatc ttcaaagata    960

caaccaggag tactatctgg ttcagcaacg ctgctcatga tattgccata a            1011
```

```
<210> SEQ ID NO 4
<211> LENGTH: 336
<212> TYPE: PRT
<213> ORGANISM: Escherichia coli
<220> FEATURE:
<221> NAME/KEY: misc_feature
<222> LOCATION: (1)..(336)
<223> OTHER INFORMATION: PapG Protein

<400> SEQUENCE: 4

Met Lys Lys Trp Phe Pro Ala Leu Leu Phe Ser Leu Cys Val Ser Gly
1               5                   10                  15

Glu Ser Ser Ala Trp Asn Asn Ile Val Phe Tyr Ser Leu Gly Asn Val
            20                  25                  30

Asn Ser Tyr Gln Gly Gly Asn Val Val Ile Thr Gln Arg Pro Gln Phe
        35                  40                  45

Ile Thr Ser Trp Arg Pro Gly Ile Ala Thr Val Thr Trp Asn Gln Cys
    50                  55                  60

Asn Gly Pro Gly Phe Ala Asp Gly Ser Trp Ala Tyr Tyr Arg Glu Tyr
65                  70                  75                  80

Ile Ala Trp Val Val Phe Pro Lys Lys Val Met Thr Lys Asn Gly Tyr
                85                  90                  95

Pro Leu Phe Ile Glu Val His Asn Lys Gly Ser Trp Ser Glu Glu Asn
            100                 105                 110

Thr Gly Asp Asn Asp Ser Tyr Phe Phe Leu Lys Gly Tyr Lys Trp Asp
        115                 120                 125

Glu Arg Ala Phe Asp Ala Gly Asn Leu Cys Gln Lys Pro Gly Glu Thr
    130                 135                 140

Thr Arg Leu Thr Glu Lys Phe Asp Asp Ile Ile Phe Lys Val Ala Leu
145                 150                 155                 160

Pro Ala Asp Leu Pro Leu Gly Asp Tyr Ser Val Thr Ile Pro Tyr Thr
                165                 170                 175

Ser Gly Met Gln Arg His Phe Ala Ser Tyr Leu Gly Ala Arg Phe Lys
            180                 185                 190

Ile Pro Tyr Asn Val Ala Lys Thr Leu Pro Arg Glu Asn Glu Met Leu
        195                 200                 205
```

```
Phe Leu Phe Lys Asn Ile Gly Gly Cys Arg Pro Ser Ala Gln Ser Leu
    210                 215                 220

Glu Ile Lys His Gly Asp Leu Ser Ile Asn Ser Ala Asn Asn His Tyr
225                 230                 235                 240

Ala Ala Gln Thr Leu Ser Val Ser Cys Asp Val Pro Ala Asn Ile Arg
                245                 250                 255

Phe Met Leu Leu Arg Asn Thr Thr Pro Thr Tyr Ser His Gly Lys Lys
            260                 265                 270

Phe Ser Val Gly Leu Gly His Gly Trp Asp Ser Ile Val Ser Val Asn
        275                 280                 285

Gly Val Asp Thr Gly Glu Thr Thr Met Arg Trp Tyr Lys Ala Gly Thr
    290                 295                 300

Gln Asn Leu Thr Ile Gly Ser Arg Leu Tyr Gly Glu Ser Ser Lys Ile
305                 310                 315                 320

Gln Pro Gly Val Leu Ser Gly Ser Ala Thr Leu Leu Met Ile Leu Pro
                325                 330                 335
```

<210> SEQ ID NO 5
<211> LENGTH: 2769
<212> TYPE: DNA
<213> ORGANISM: Escherichia coli
<220> FEATURE:
<221> NAME/KEY: misc_feature
<222> LOCATION: (1)..(2769)
<223> OTHER INFORMATION: E. coli plasmid pFS8 cloacin DF13/aerobactin receptor gene (Includes IutA)

<400> SEQUENCE: 5

```
gatctgcacg tattcttaat cgcgtaatgg gacgtgattt attcgatctc agtatgccgc      60

ccgccctgat tcagtggcgc aggcacctag ggaaaacgca gccggacttg tctttaactc     120

gctacacagc atctttgggc tgattttttc cgcccgtatg gaggaataat gatgataagc     180

aaaaagtata cgctttgggc tctcaaccca ctgcttctta ccatgatggc gccagcagtc     240

gctcaacaaa ccgatgatga aacgttcgtg gtgtctgcca accgcagcaa tcgcaccgta     300

gcggagatgg cgcaaaccac ctgggttatc gaaaacgccg aactggaaca gcagattcag     360

ggcggcaaag agcttaaaga cgcactggct cagctgatcc ctggccttga cgtcagcagc     420

cggagccgca ccaactacgg tatgaatgtg cgtggccgcc cgctggtcgt gctggttgac     480

ggcgtgcgtc tcaactcttc acgtaccgac agccgacaac tggactctat agatcctttt     540

aatatgcacc atattgaagt gatcttcggt gcgacgtccc tgtacggcgg cggcagtacc     600

ggtggcctga tcaacatcgt gaccaaaaaa ggccagccgg aaaccatgat ggagtttgag     660

gctggcacca aaagtggctt tagcagcagt aaagatcacg atgaacgcat tgccggagct     720

gtctccggcg gaaatgagca tatctccgga cgtctttccg tggcatatca gaaatttggc     780

ggctggtttg acggtaacgg cgatgccacc ttgcttgata acacccagac cggcctgcag     840

tactccgatc ggctggacat catgggaact ggtacgctga acatcgatga atcccggcag     900

cttcagttga tcacacagta ctataaaagc cagggcgacg acgattacgg gcttaatctc     960

gggaaaggct tctctgccat cagagggacc agcacgccat tcgtcagtaa cgggctgaat    1020

tccgaccgta ttcccggcac tgacgggcat ttgatcagcc tgcagtactc tgacagcgct    1080

tttctgggac aggagctggt cggtcaggtt tactaccgcg atgagtcgtt gcgattctac    1140

ccgttcccga cggtaaatgc gaacaaacag gtgacggctt tctcttcgtc acagcaggac    1200

accgaccagt acggcatgaa actgactctg aacagcaaac cgatggacgg ctggcaaatc    1260
```

```
acctgggggc tggatgctga tcatgagcgc tttacctcca accagatgtt cttcgacctg   1320

gctcaggcaa gcgcttccgg agggctgaac aacaagaaga tttacaccac cgggcgctat   1380

ccgtcgtatg acatcaccaa cctggcggcc ttcctgcaat caggctatga catcaataat   1440

ctctttaccc tcaacggtgg cgtacgctat cagtacactg aaaacaagat tgatgatttc   1500

atcggctacg cgcagcaacg gcagattggc gccgggaagg ctacatccgc cgacgcattc   1560

tggcggctca gtcgattacg acacttcctg ttcaacgccg gtctgctgat gcacatcacc   1620

gaaccgcagc aggcatggct caacttctcc cagggcctgg agctgccgga cccgggtaaa   1680

tactatggtc gcggcatcta tggtgctgca gtgaacggcc atcttcctct aacaaagagt   1740

gtgaacgtca gcgacagcaa gctggaaggc gtgaaagtcg attcttatga gctgggctgg   1800

cgctttactg gcaataatct gcgtacccaa atcgcggcct actattcgat ttctgataag   1860

agcgtggtgg cgaataaaga tctgaccatc agcgtggtgg acgacaaacg ccgtatttac   1920

ggcgtggaag gtgcggtgga ctacctgatt cctgatactg actggagtac cggagtgaac   1980

ttcaacgtgc tgaaaactga gtcgaaagtg aacggtacct ggcagaaata cgatgtgaag   2040

acagcaagcc catcaaaagc gacagcctac attggctggg caccggaccc gtggagtctg   2100

cgcgtgcaga gcaccacctc ctttgacgtg agcgacgcgc agggctacaa ggtcgatggc   2160

tataccaccg tggatctgct cggcagttat cagcttccgg tgggtacact cagcttcagc   2220

attgaaaacc tcttcgaccg tgactacacc actgtctggg ggcagcgtgc accactgtac   2280

tacagcccgg gttacggccc agcgtcactg tacgactaca aaggcagggg ccgaaccttt   2340

ggtctgaact actctgtgct gttctgaccg gtattccttt acaacaaagg tacgctgata   2400

tcaacatggc cgctgacagc caagttgata tcatataata cacgacataa tctgtagtca   2460

gggaggatag actctttact gactacagat tatgtcctgt tccgtgctca tttcctcaaa   2520

aaaatacaag aaaagaatta gtattctaac aaaaagtgaa ataaattgta tcaaactccc   2580

tcttttaatc ctgttgagta aatcagcttt tgcaatagga ttgaaagagt gtaagtggaa   2640

tctcttccgg atactcgtta ccaccgtggc tagaatatct acggctgcgg gggtgatgct   2700

gccaacttac tgatttagtg tatgatggtg tttttgaggt gctccagtgg cttctgtttc   2760

tatcagctg                                                           2769
```

```
<210> SEQ ID NO 6
<211> LENGTH: 733
<212> TYPE: PRT
<213> ORGANISM: Escherichia coli
<220> FEATURE:
<221> NAME/KEY: misc_feature
<222> LOCATION: (1)..(733)
<223> OTHER INFORMATION: IutA Amino Acid Sequence

<400> SEQUENCE: 6

Met Met Ile Ser Lys Lys Tyr Thr Leu Trp Ala Leu Asn Pro Leu Leu
1               5                   10                  15

Leu Thr Met Met Ala Pro Ala Val Ala Gln Gln Thr Asp Asp Glu Thr
            20                  25                  30

Phe Val Val Ser Ala Asn Arg Ser Asn Arg Thr Val Ala Glu Met Ala
        35                  40                  45

Gln Thr Thr Trp Val Ile Glu Asn Ala Glu Leu Glu Gln Gln Ile Gln
    50                  55                  60

Gly Gly Lys Glu Leu Lys Asp Ala Leu Ala Gln Leu Ile Pro Gly Leu
65                  70                  75                  80
```

```
Asp Val Ser Ser Arg Ser Arg Thr Asn Tyr Gly Met Asn Val Arg Gly
                85                  90                  95

Arg Pro Leu Val Val Leu Val Asp Gly Val Arg Leu Asn Ser Ser Arg
            100                 105                 110

Thr Asp Ser Arg Gln Leu Asp Ser Ile Asp Pro Phe Asn Ile Asp His
        115                 120                 125

Ile Glu Val Ile Ser Gly Ala Thr Ser Leu Tyr Gly Gly Gly Ser Thr
    130                 135                 140

Gly Gly Leu Ile Asn Ile Val Thr Lys Lys Gly Gln Pro Glu Thr Met
145                 150                 155                 160

Met Glu Phe Glu Ala Gly Thr Lys Ser Gly Phe Ser Ser Ser Lys Asp
                165                 170                 175

His Asp Glu Arg Ile Ala Gly Ala Val Ser Gly Gly Asn Glu His Ile
            180                 185                 190

Ser Gly Arg Leu Ser Val Ala Tyr Gln Lys Phe Gly Gly Trp Phe Asp
        195                 200                 205

Gly Asn Gly Asp Ala Thr Leu Leu Asp Asn Thr Gln Thr Gly Leu Gln
    210                 215                 220

Tyr Ser Asp Arg Leu Asp Ile Met Gly Thr Gly Thr Leu Asn Ile Asp
225                 230                 235                 240

Glu Ser Arg Gln Leu Gln Leu Ile Thr Gln Tyr Tyr Lys Ser Gln Gly
                245                 250                 255

Asp Asp Asp Tyr Gly Leu Asn Leu Gly Lys Gly Phe Ser Ala Ile Arg
            260                 265                 270

Gly Thr Ser Thr Pro Phe Val Ser Asn Gly Leu Asn Ser Asp Arg Ile
        275                 280                 285

Pro Gly Thr Glu Arg His Leu Ile Ser Leu Gln Tyr Ser Asp Ser Ala
    290                 295                 300

Phe Leu Gly Gln Glu Leu Val Gly Gln Val Tyr Tyr Arg Asp Glu Ser
305                 310                 315                 320

Leu Arg Phe Tyr Pro Phe Pro Thr Val Asn Ala Asn Lys Gln Val Thr
                325                 330                 335

Ala Phe Ser Ser Ser Gln Gln Asp Thr Asp Gln Tyr Gly Met Lys Leu
            340                 345                 350

Thr Leu Asn Ser Lys Pro Met Asp Gly Trp Gln Ile Thr Trp Gly Leu
        355                 360                 365

Asp Ala Asp His Glu Arg Phe Thr Ser Asn Gln Met Phe Phe Asp Leu
    370                 375                 380

Ala Gln Ala Ser Ala Ser Gly Gly Leu Asn Asn Lys Lys Ile Tyr Thr
385                 390                 395                 400

Thr Gly Arg Tyr Pro Ser Tyr Asp Ile Thr Asn Leu Ala Ala Phe Leu
                405                 410                 415

Gln Ser Gly Tyr Asp Ile Asn Asn Leu Phe Thr Leu Asn Gly Gly Val
            420                 425                 430

Arg Tyr Gln Tyr Thr Glu Asn Lys Ile Asp Asp Phe Ile Gly Tyr Ala
        435                 440                 445

Gln Gln Arg Gln Ile Ala Ala Gly Lys Ala Thr Ser Ala Asp Ala Ile
    450                 455                 460

Pro Gly Gly Ser Val Asp Tyr Asp Asn Phe Leu Phe Asn Ala Gly Leu
465                 470                 475                 480

Leu Met His Ile Thr Glu Arg Gln Gln Ala Trp Leu Asn Phe Ser Gln
                485                 490                 495
```

```
Gly Val Glu Leu Pro Asp Pro Gly Lys Tyr Tyr Gly Arg Gly Ile Tyr
            500                 505                 510

Gly Ala Ala Val Asn Gly His Leu Pro Leu Thr Lys Ser Val Asn Val
        515                 520                 525

Ser Asp Ser Lys Leu Glu Gly Val Lys Val Asp Ser Tyr Glu Leu Gly
    530                 535                 540

Trp Arg Phe Thr Gly Asn Asn Leu Arg Thr Gln Ile Ala Ala Tyr Tyr
545                 550                 555                 560

Ser Ile Ser Asp Lys Ser Val Val Ala Asn Lys Asp Leu Thr Ile Ser
                565                 570                 575

Val Val Asp Asp Lys Arg Arg Ile Tyr Gly Val Glu Gly Ala Val Asp
            580                 585                 590

Tyr Leu Ile Pro Asp Thr Asp Trp Ser Thr Gly Val Asn Phe Asn Val
        595                 600                 605

Leu Lys Thr Glu Ser Lys Val Asn Gly Thr Trp Gln Lys Tyr Asp Val
    610                 615                 620

Lys Thr Ala Ser Pro Ser Lys Ala Thr Ala Tyr Ile Gly Trp Ala Pro
625                 630                 635                 640

Asp Pro Trp Ser Leu Arg Val Gln Ser Thr Thr Ser Phe Asp Val Ser
                645                 650                 655

Asp Ala Gln Gly Tyr Lys Val Asp Gly Tyr Thr Thr Ala Asp Leu Leu
            660                 665                 670

Gly Ser Tyr Gln Leu Pro Val Gly Thr Leu Ser Phe Ser Ile Glu Asn
        675                 680                 685

Leu Phe Asp Arg Asp Tyr Thr Thr Val Trp Gly Gln Arg Ala Pro Leu
    690                 695                 700

Tyr Tyr Ser Pro Gly Tyr Gly Pro Ala Ser Leu Tyr Asp Tyr Lys Gly
705                 710                 715                 720

Arg Gly Arg Thr Phe Gly Leu Asn Tyr Ser Val Leu Phe
                725                 730
```

<210> SEQ ID NO 7
<211> LENGTH: 34
<212> TYPE: DNA
<213> ORGANISM: Escherichia coli
<220> FEATURE:
<221> NAME/KEY: misc_feature
<222> LOCATION: (1)..(34)
<223> OTHER INFORMATION: fimH F

<400> SEQUENCE: 7
gcgtccggat ccaaacgagt tattaccctg tttg 34

<210> SEQ ID NO 8
<211> LENGTH: 37
<212> TYPE: DNA
<213> ORGANISM: Escherichia coli
<220> FEATURE:
<221> NAME/KEY: misc_feature
<222> LOCATION: (1)..(37)
<223> OTHER INFORMATION: fimH R

<400> SEQUENCE: 8
gcgccgcgcc atggttattg ataaacaaaa gtcacgc 37

<210> SEQ ID NO 9
<211> LENGTH: 36
<212> TYPE: DNA
<213> ORGANISM: Escherichia coli
<220> FEATURE:

<221> NAME/KEY: misc_feature
<222> LOCATION: (1)..(36)
<223> OTHER INFORMATION: iutA F

<400> SEQUENCE: 9
cgcggcggat ccataagcaa aaagtatacg ctttgg 36

<210> SEQ ID NO 10
<211> LENGTH: 34
<212> TYPE: DNA
<213> ORGANISM: Escherichia coli
<220> FEATURE:
<221> NAME/KEY: misc_feature
<222> LOCATION: (1)..(34)
<223> OTHER INFORMATION: iutA R

<400> SEQUENCE: 10
tctggaccat ggtcagaaca gcacagagta gttc 34

<210> SEQ ID NO 11
<211> LENGTH: 33
<212> TYPE: DNA
<213> ORGANISM: Escherichia coli
<220> FEATURE:
<221> NAME/KEY: misc_feature
<222> LOCATION: (1)..(33)
<223> OTHER INFORMATION: papG R

<400> SEQUENCE: 11
gcgcaggcta gcttatggca atatcatgag cag 33

<210> SEQ ID NO 12
<211> LENGTH: 20
<212> TYPE: DNA
<213> ORGANISM: Escherichia coli
<220> FEATURE:
<221> NAME/KEY: misc_feature
<222> LOCATION: (1)..(20)
<223> OTHER INFORMATION: fimHseqF1

<400> SEQUENCE: 12
ttccctacta ccagcgaaac 20

<210> SEQ ID NO 13
<211> LENGTH: 20
<212> TYPE: DNA
<213> ORGANISM: Escherichia coli
<220> FEATURE:
<221> NAME/KEY: misc_feature
<222> LOCATION: (1)..(20)
<223> OTHER INFORMATION: fimHseqF2

<400> SEQUENCE: 13
gtacagttga cgcgcaacgg 20

<210> SEQ ID NO 14
<211> LENGTH: 20
<212> TYPE: DNA
<213> ORGANISM: Escherichia coli
<220> FEATURE:
<221> NAME/KEY: misc_feature
<222> LOCATION: (1)..(20)
<223> OTHER INFORMATION: aerobactin receptor FS8FseqF1

<400> SEQUENCE: 14
gacagccgac aactggactc 20

<210> SEQ ID NO 15
<211> LENGTH: 20
<212> TYPE: DNA
<213> ORGANISM: Escherichia coli
<220> FEATURE:
<221> NAME/KEY: misc_feature
<222> LOCATION: (1)..(20)
<223> OTHER INFORMATION: aerobactin receptor FS8FseqF2

<400> SEQUENCE: 15
aatcccggca gcttcagttg 20

<210> SEQ ID NO 16
<211> LENGTH: 20
<212> TYPE: DNA
<213> ORGANISM: Escherichia coli
<220> FEATURE:
<221> NAME/KEY: misc_feature
<222> LOCATION: (1)..(20)
<223> OTHER INFORMATION: aerobactin receptor FS8FseqF3

<400> SEQUENCE: 16
cctccaacca gatgttcttc 20

<210> SEQ ID NO 17
<211> LENGTH: 20
<212> TYPE: DNA
<213> ORGANISM: Escherichia coli
<220> FEATURE:
<221> NAME/KEY: misc_feature
<222> LOCATION: (1)..(20)
<223> OTHER INFORMATION: aerobactin receptor FS8FseqF4

<400> SEQUENCE: 17
aacggccatc ttcctctaac 20

<210> SEQ ID NO 18
<211> LENGTH: 20
<212> TYPE: DNA
<213> ORGANISM: Escherichia coli
<220> FEATURE:
<221> NAME/KEY: misc_feature
<222> LOCATION: (1)..(20)
<223> OTHER INFORMATION: aerobactin receptor FS8FseqF5

<400> SEQUENCE: 18
agagcaccac ctcctttgac 20

<210> SEQ ID NO 19
<211> LENGTH: 9
<212> TYPE: PRT
<213> ORGANISM: Artificial Sequence
<220> FEATURE:
<223> OTHER INFORMATION: Synthetic: Leukotoxin Repeat Sequence
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 19

Leu Xaa Gly Gly Xaa Gly Asn Asp Xaa
1 5

```
<210> SEQ ID NO 20
<211> LENGTH: 953
<212> TYPE: PRT
<213> ORGANISM: Pasteurella haemolytica
<220> FEATURE:
<221> NAME/KEY: misc_feature
<222> LOCATION: (1)..(953)
<223> OTHER INFORMATION: Leukotoxin A protein sequence

<400> SEQUENCE: 20

Met Gly Asn Lys Leu Thr Asn Ile Ser Thr Asn Leu Lys Ser Ser Trp
1               5                   10                  15

Leu Thr Ala Lys Ser Gly Leu Asn Arg Thr Gly Gln Ser Leu Ala Lys
            20                  25                  30

Ala Gly Gln Ser Leu Lys Thr Gly Ala Lys Lys Ile Ile Leu Tyr Ile
        35                  40                  45

Pro Lys Asp Tyr Gln Tyr Asp Thr Asp Lys Gly Asn Gly Leu Gln Asp
    50                  55                  60

Leu Val Lys Ala Ala Glu Glu Leu Gly Ile Glu Val Gln Lys Glu Glu
65                  70                  75                  80

Ser Asn Asp Ile Ala Lys Ala Gln Thr Ser Leu Gly Thr Ile His Asn
                85                  90                  95

Val Leu Gly Leu Thr Glu Arg Gly Ile Val Leu Ser Ala Pro Gln Leu
            100                 105                 110

Asp Lys Leu Leu Gln Lys Thr Lys Val Gly Gln Ala Ile Gly Ser Thr
        115                 120                 125

Glu Asn Ile Thr Lys Gly Phe Ser Asn Ala Lys Thr Val Leu Ser Gly
    130                 135                 140

Ile Gln Ser Ile Leu Gly Ser Val Leu Ala Gly Met Asp Leu Asp Glu
145                 150                 155                 160

Ala Leu Gln Asn Asn Ser Asn Glu Leu Thr Leu Ala Lys Ala Gly Leu
                165                 170                 175

Glu Leu Thr Asn Ser Leu Ile Glu Asn Ile Ala Asn Ser Val Lys Thr
            180                 185                 190

Leu Asp Ala Phe Gly Asp Gln Ile Asn Gln Leu Gly Ser Lys Leu Gln
        195                 200                 205

Asn Val Lys Gly Leu Ser Ser Leu Gly Glu Lys Leu Lys Gly Leu Ser
    210                 215                 220

Gly Phe Asp Lys Thr Ser Leu Gly Leu Asp Ile Val Ser Gly Leu Leu
225                 230                 235                 240

Ser Gly Ala Thr Ala Ala Leu Val Leu Ala Asp Lys Asn Ala Ser Thr
                245                 250                 255

Ser Arg Lys Val Gly Ala Gly Phe Glu Leu Ala Asn Gln Val Val Gly
            260                 265                 270

Asn Ile Thr Lys Ala Val Ser Ser Tyr Ile Leu Ala Gln Arg Val Ala
        275                 280                 285

Ala Gly Leu Ser Ser Thr Gly Pro Val Ala Ala Leu Ile Ala Ser Thr
    290                 295                 300

Val Ser Leu Ala Ile Ser Pro Leu Ser Phe Ala Gly Ile Ala Asp Lys
305                 310                 315                 320

Phe Asn His Ala Lys Ser Leu Glu Ser Tyr Ala Glu Arg Phe Lys Lys
                325                 330                 335

Leu Gly Tyr Asp Gly Asp Asn Leu Leu Ala Glu Tyr Gln Arg Gly Thr
            340                 345                 350
```

```
Gly Thr Ile Asp Ala Ser Val Thr Ala Ile Asn Thr Ala Leu Ala Ala
        355                 360                 365

Ile Ala Gly Gly Val Ser Ala Ala Ala Ala Gly Ser Val Val Ala Ser
    370                 375                 380

Pro Ile Ala Leu Leu Val Ser Gly Ile Thr Gly Val Ile Ser Thr Ile
385                 390                 395                 400

Leu Gln Tyr Ser Lys Gln Ala Met Phe Glu His Val Ala Asn Lys Ile
                405                 410                 415

His Asn Lys Ile Val Glu Trp Glu Lys Asn Asn Pro Gly Lys Asn Tyr
            420                 425                 430

Phe Glu Asn Gly Tyr Asp Ala Arg Tyr Leu Ala Asn Leu Gln Asp Asn
        435                 440                 445

Met Lys Phe Leu Leu Asn Leu Asn Lys Glu Leu Gln Ala Glu Arg Val
    450                 455                 460

Ile Ala Ile Thr Gln Gln Gln Trp Asp Asn Asn Ile Gly Asp Leu Ala
465                 470                 475                 480

Gly Ile Ser Arg Leu Gly Glu Lys Val Leu Ser Gly Lys Ala Tyr Val
                485                 490                 495

Asp Ala Phe Glu Glu Gly Gln His Leu Lys Ala Asp Lys Leu Val Gln
            500                 505                 510

Leu Asp Ser Ala Lys Gly Ile Ile Asp Val Ser Asn Thr Gly Glu Ala
        515                 520                 525

Lys Thr Gln His Ile Leu Phe Arg Thr Pro Leu Leu Thr Pro Gly Thr
    530                 535                 540

Glu Lys Arg Glu Arg Val Gln Thr Gly Lys Tyr Glu Tyr Ile Thr Lys
545                 550                 555                 560

Leu His Ile Asn Arg Val Asp Ser Trp Lys Ile Thr Asp Gly Ala Ala
                565                 570                 575

Ser Ser Thr Phe Asp Leu Thr Asn Val Val Gln Arg Ile Gly Ile Glu
            580                 585                 590

Leu Asp Asn Ala Gly Asn Val Thr Lys Thr Lys Glu Thr Lys Ile Ile
        595                 600                 605

Ala Lys Leu Gly Glu Gly Asp Asp Asn Val Phe Val Gly Ser Gly Thr
    610                 615                 620

Thr Glu Ile Asp Gly Gly Glu Gly Tyr Asp Arg Val His Tyr Ser Arg
625                 630                 635                 640

Gly Asn Tyr Gly Ala Leu Thr Ile Asp Ala Thr Lys Glu Thr Glu Gln
                645                 650                 655

Gly Ser Tyr Thr Val Asn Arg Phe Val Glu Ser Gly Lys Ala Leu His
            660                 665                 670

Glu Val Thr Ser Thr His Thr Ala Leu Val Gly Asn Arg Glu Glu Lys
        675                 680                 685

Ile Glu Tyr Arg His Ser Asn Asn Gln His His Ala Gly Tyr Tyr Thr
    690                 695                 700

Lys Asp Thr Leu Lys Ala Val Glu Glu Ile Ile Gly Thr Ser His Asn
705                 710                 715                 720

Asp Ile Phe Lys Gly Ser Lys Phe Asn Asp Ala Phe Asn Gly Gly Asp
                725                 730                 735

Gly Val Asp Thr Ile Asp Gly Asn Asp Gly Asn Asp Arg Leu Phe Gly
            740                 745                 750

Gly Lys Gly Asp Asp Ile Ile Asp Gly Gly Asn Gly Asp Asp Phe Ile
        755                 760                 765

Asp Gly Gly Lys Gly Asn Asp Leu Leu His Gly Gly Lys Gly Asp Asp
```

```
    770                 775                 780

Ile Phe Val His Arg Gln Gly Asp Gly Asn Asp Ser Ile Thr Glu Ser
785                 790                 795                 800

Glu Gly Asn Asp Lys Leu Ser Phe Ser Asp Ser Asn Leu Lys Asp Leu
                805                 810                 815

Thr Phe Glu Lys Val Asn His His Leu Val Ile Thr Asn Thr Lys Gln
            820                 825                 830

Glu Lys Val Thr Ile Gln Asn Trp Phe Arg Glu Ala Glu Phe Ala Lys
        835                 840                 845

Thr Ile Gln Asn Tyr Val Ala Thr Arg Asp Asp Lys Ile Glu Glu Ile
    850                 855                 860

Ile Gly Gln Asn Gly Glu Arg Ile Thr Ser Lys Gln Val Asp Glu Leu
865                 870                 875                 880

Ile Glu Lys Gly Asn Gly Lys Ile Ala Gln Ser Glu Leu Thr Lys Val
                885                 890                 895

Val Asp Asn Tyr Gln Leu Leu Lys Tyr Ser Arg Asp Ala Ser Asn Ser
            900                 905                 910

Leu Asp Lys Leu Ile Ser Ser Ala Ser Ala Phe Thr Ser Ser Asn Asp
        915                 920                 925

Ser Arg Asn Val Leu Ala Ser Pro Thr Ser Met Leu Asp Pro Ser Leu
    930                 935                 940

Ser Ser Ile Gln Phe Ala Arg Ala Ala
945                 950


<210> SEQ ID NO 21
<211> LENGTH: 1011
<212> TYPE: DNA
<213> ORGANISM: Escherichia coli
<220> FEATURE:
<221> NAME/KEY: misc_feature
<222> LOCATION: (1)..(1011)
<223> OTHER INFORMATION: Escherichia coli strain APEC 41 PapGII (papGII)
      gene, complete cds

<400> SEQUENCE: 21

atgaaaaaat ggttccctgc tttgttattt tccttgtgtg tgtctggtga gtcctctgca     60

tggaataata ttgtctttta ctcccttgga aacgttaact cttatcaggg agggaatgtg    120

gtgattactc aaaggccaca atttataact tcgtggcgcc cgggcattgc tacggtaacc    180

tggaatcagt gtaatggtcc tgggtttgct gatggttcct gggcttacta cagggagtat    240

attgcgtggg tagtattccc caaaaaggtt atgaccaaaa atggatatcc cttatttatt    300

gaggttcata ataaaggtag ctggagtgag gagaatactg gtgacaatga cagctatttt    360

tttctcaagg ggtataagtg ggatgagcgg gcctttgatg caggtaattt gtgtcagaaa    420

ccaggagaaa caacccgtct gactgagaaa tttgacgata ttatttttaa agtcgcccta    480

cctgcagatc ttcctttagg ggattattct gttacaattc catacacttc cggcatgcag    540

cgtcatttcg cgagttactt gggagcccgt tttaaaatcc catacaatgt ggccaaaact    600

ctcccaagag agaatgaaat gttattctta tttaagaata tcggcggatg ccgtccttct    660

gcacagtctc tggaaataaa gcatggtgat ctgtctatta atagcgctaa taatcattat    720

gcggctcaga ctctttctgt gtcttgcgat gtgcctgcaa atattcgttt tatgctgtta    780

agaaatacaa ctccgacata cagccatggt aagaaatttt cggttggtct ggggcatggc    840

tgggactcca ttgtttcggt taacggggtg gacacaggag agacaacgat gagatggtac    900

aaagcaggta cacaaaacct gaccatcggc agtcgcctct atggtgaatc ttcaaagata    960
```

```
caaccaggag tactatctgg ttcagcaacg ctgctcatga tattgccata a          1011


<210> SEQ ID NO 22
<211> LENGTH: 1011
<212> TYPE: DNA
<213> ORGANISM: Escherichia coli
<220> FEATURE:
<221> NAME/KEY: misc_feature
<222> LOCATION: (1)..(1011)
<223> OTHER INFORMATION: Escherichia coli strain APEC 1 PapGII (papGII)
      gene, complete cds

<400> SEQUENCE: 22

atgaaaaaat ggttccctgc tttgttattt tccttgtgtg tgtctggtga gtcctctgca     60

tggaataata ttgtctttta ctcccttgga aacgttaact cttatcaggg agggaatgtg    120

gtgattactc aaaggccaca atttataact tcgtggcgcc cgggcattgc tacggtaacc    180

tggaatcagt gtaatggtcc tgggtttgct gatggtttct gggcttacta cagggagtat    240

attgcgtggg tagtattccc caaaaaggtt atgaccaaaa atggatatcc cttatttatt    300

gaggttcata ataaaggtag ctggagtgag gagaatactg gtgacaatga cagctatttt    360

tttctcaagg ggtataagtg ggatgagcgg gcctttgatg caggtaattt gtgtcagaaa    420

ccaggagaaa caacccgtct gactgagaaa tttgacgata ttatttttaa agtcgcccta    480

cctgcagatc ttcctttagg ggattattct gttacaattc catacacttc cggcatgcag    540

cgtcatttcg cgagttactt gggagcccgt tttaaaatcc catacaatgt ggccaaaact    600

ctcccaagag agaatgaaat gttattctta tttaagaata tcggcggatg ccgtccttct    660

gcacagtctc tggaaataaa gcatggtgat ctgtctatta atagcgctaa taatcattat    720

gcggctcaga ctctttctgt gtcttgcgat gtgcctgcaa atattcgttt tatgctgtta    780

agaaatacaa ctccgacata cagccatggt aagaaatttt cggttggtct ggggcatggc    840

tgggactcca ttgtttcggt taacggggtg gacacaggag agacaacgat gagatggtac    900

aaagcaggta cacaaaacct gaccatcggc agtcgcctct atggtgaatc ttcaaagata    960

caaccaggag tactatctgg ttcagcaacg ctgctcatga tattgccata a          1011


<210> SEQ ID NO 23
<211> LENGTH: 336
<212> TYPE: PRT
<213> ORGANISM: Escherichia coli
<220> FEATURE:
<221> NAME/KEY: misc_feature
<222> LOCATION: (1)..(336)
<223> OTHER INFORMATION: Escherichia coli strain APEC 41 PapGII (papGII)
      gene, complete cds

<400> SEQUENCE: 23

Met Lys Lys Trp Phe Pro Ala Leu Leu Phe Ser Leu Cys Val Ser Gly
1               5                   10                  15

Glu Ser Ser Ala Trp Asn Asn Ile Val Phe Tyr Ser Leu Gly Asn Val
            20                  25                  30

Asn Ser Tyr Gln Gly Gly Asn Val Val Ile Thr Gln Arg Pro Gln Phe
        35                  40                  45

Ile Thr Ser Trp Arg Pro Gly Ile Ala Thr Val Thr Trp Asn Gln Cys
    50                  55                  60

Asn Gly Pro Gly Phe Ala Asp Gly Ser Trp Ala Tyr Tyr Arg Glu Tyr
65                  70                  75                  80

Ile Ala Trp Val Val Phe Pro Lys Lys Val Met Thr Lys Asn Gly Tyr
```

```
                85                  90                  95

Pro Leu Phe Ile Glu Val His Asn Lys Gly Ser Trp Ser Glu Glu Asn
            100                 105                 110

Thr Gly Asp Asn Asp Ser Tyr Phe Phe Leu Lys Gly Tyr Lys Trp Asp
        115                 120                 125

Glu Arg Ala Phe Asp Ala Gly Asn Leu Cys Gln Lys Pro Gly Glu Thr
    130                 135                 140

Thr Arg Leu Thr Glu Lys Phe Asp Asp Ile Ile Phe Lys Val Ala Leu
145                 150                 155                 160

Pro Ala Asp Leu Pro Leu Gly Asp Tyr Ser Val Thr Ile Pro Tyr Thr
                165                 170                 175

Ser Gly Met Gln Arg His Phe Ala Ser Tyr Leu Gly Ala Arg Phe Lys
            180                 185                 190

Ile Pro Tyr Asn Val Ala Lys Thr Leu Pro Arg Glu Asn Glu Met Leu
        195                 200                 205

Phe Leu Phe Lys Asn Ile Gly Gly Cys Arg Pro Ser Ala Gln Ser Leu
    210                 215                 220

Glu Ile Lys His Gly Asp Leu Ser Ile Asn Ser Ala Asn Asn His Tyr
225                 230                 235                 240

Ala Ala Gln Thr Leu Ser Val Ser Cys Asp Val Pro Ala Asn Ile Arg
                245                 250                 255

Phe Met Leu Leu Arg Asn Thr Thr Pro Thr Tyr Ser His Gly Lys Lys
            260                 265                 270

Phe Ser Val Gly Leu Gly His Gly Trp Asp Ser Ile Val Ser Val Asn
        275                 280                 285

Gly Val Asp Thr Gly Glu Thr Thr Met Arg Trp Tyr Lys Ala Gly Thr
    290                 295                 300

Gln Asn Leu Thr Ile Gly Ser Arg Leu Tyr Gly Glu Ser Ser Lys Ile
305                 310                 315                 320

Gln Pro Gly Val Leu Ser Gly Ser Ala Thr Leu Leu Met Ile Leu Pro
                325                 330                 335


<210> SEQ ID NO 24
<211> LENGTH: 336
<212> TYPE: PRT
<213> ORGANISM: Escherichia coli
<220> FEATURE:
<221> NAME/KEY: misc_feature
<222> LOCATION: (1)..(336)
<223> OTHER INFORMATION: Escherichia coli strain APEC 1 PapGII (papGII)
      gene, complete cds

<400> SEQUENCE: 24

Met Lys Lys Trp Phe Pro Ala Leu Leu Phe Ser Leu Cys Val Ser Gly
1               5                   10                  15

Glu Ser Ser Ala Trp Asn Asn Ile Val Phe Tyr Ser Leu Gly Asn Val
            20                  25                  30

Asn Ser Tyr Gln Gly Gly Asn Val Val Ile Thr Gln Arg Pro Gln Phe
        35                  40                  45

Ile Thr Ser Trp Arg Pro Gly Ile Ala Thr Val Thr Trp Asn Gln Cys
    50                  55                  60

Asn Gly Pro Gly Phe Ala Asp Gly Phe Trp Ala Tyr Tyr Arg Glu Tyr
65                  70                  75                  80

Ile Ala Trp Val Val Phe Pro Lys Lys Val Met Thr Lys Asn Gly Tyr
                85                  90                  95

Pro Leu Phe Ile Glu Val His Asn Lys Gly Ser Trp Ser Glu Glu Asn
```

```
            100                 105                 110

Thr Gly Asp Asn Asp Ser Tyr Phe Phe Leu Lys Gly Tyr Lys Trp Asp
        115                 120                 125

Glu Arg Ala Phe Asp Ala Gly Asn Leu Cys Gln Lys Pro Gly Glu Thr
    130                 135                 140

Thr Arg Leu Thr Glu Lys Phe Asp Asp Ile Ile Phe Lys Val Ala Leu
145                 150                 155                 160

Pro Ala Asp Leu Pro Leu Gly Asp Tyr Ser Val Thr Ile Pro Tyr Thr
                165                 170                 175

Ser Gly Met Gln Arg His Phe Ala Ser Tyr Leu Gly Ala Arg Phe Lys
            180                 185                 190

Ile Pro Tyr Asn Val Ala Lys Thr Leu Pro Arg Glu Asn Glu Met Leu
        195                 200                 205

Phe Leu Phe Lys Asn Ile Gly Gly Cys Arg Pro Ser Ala Gln Ser Leu
    210                 215                 220

Glu Ile Lys His Gly Asp Leu Ser Ile Asn Ser Ala Asn Asn His Tyr
225                 230                 235                 240

Ala Ala Gln Thr Leu Ser Val Ser Cys Asp Val Pro Ala Asn Ile Arg
                245                 250                 255

Phe Met Leu Leu Arg Asn Thr Thr Pro Thr Tyr Ser His Gly Lys Lys
            260                 265                 270

Phe Ser Val Gly Leu Gly His Gly Trp Asp Ser Ile Val Ser Val Asn
        275                 280                 285

Gly Val Asp Thr Gly Glu Thr Thr Met Arg Trp Tyr Lys Ala Gly Thr
    290                 295                 300

Gln Asn Leu Thr Ile Gly Ser Arg Leu Tyr Gly Glu Ser Ser Lys Ile
305                 310                 315                 320

Gln Pro Gly Val Leu Ser Gly Ser Ala Thr Leu Leu Met Ile Leu Pro
                325                 330                 335


<210> SEQ ID NO 25
<211> LENGTH: 300
<212> TYPE: PRT
<213> ORGANISM: Escherichia coli
<220> FEATURE:
<221> NAME/KEY: misc_feature
<222> LOCATION: (1)..(300)
<223> OTHER INFORMATION: FimH [Escherichia coli]

<400> SEQUENCE: 25

Met Lys Arg Val Ile Thr Leu Phe Ala Val Leu Leu Met Gly Trp Ser
1               5                   10                  15

Val Asn Ala Trp Ser Phe Ala Cys Lys Thr Ala Asn Gly Thr Ala Ile
            20                  25                  30

Pro Ile Gly Gly Gly Ser Ala Asn Val Tyr Val Asn Leu Ala Pro Ala
        35                  40                  45

Val Asn Val Gly Gln Asn Leu Val Val Asp Leu Ser Thr Gln Ile Phe
    50                  55                  60

Cys His Asn Asp Tyr Pro Glu Thr Ile Thr Asp Tyr Val Thr Leu Gln
65                  70                  75                  80

Arg Gly Ser Ala Tyr Gly Gly Val Leu Ser Asn Phe Ser Gly Thr Val
                85                  90                  95

Lys Tyr Ser Gly Ser Ser Tyr Pro Phe Pro Thr Thr Ser Glu Thr Pro
            100                 105                 110

Arg Val Val Tyr Asn Ser Arg Thr Asp Lys Pro Trp Pro Val Ala Leu
        115                 120                 125
```

```
Tyr Leu Thr Pro Val Ser Ser Ala Gly Gly Val Ala Ile Lys Ala Gly
    130                 135                 140

Ser Leu Ile Ala Val Leu Ile Leu Arg Gln Thr Asn Asn Tyr Asn Ser
145                 150                 155                 160

Asp Asp Phe Gln Phe Val Trp Asn Ile Tyr Ala Asn Asn Asp Val Val
                165                 170                 175

Val Pro Thr Gly Gly Cys Asp Val Ser Ala Arg Asp Val Thr Val Thr
            180                 185                 190

Leu Pro Asp Tyr Pro Gly Ser Val Pro Ile Pro Leu Thr Val Tyr Cys
        195                 200                 205

Ala Lys Ser Gln Asn Leu Gly Tyr Tyr Leu Ser Gly Thr Thr Ala Asp
    210                 215                 220

Ala Gly Asn Ser Ile Phe Thr Asn Thr Ala Ser Phe Ser Pro Ala Gln
225                 230                 235                 240

Gly Val Gly Val Gln Leu Thr Arg Asn Gly Thr Ile Ile Pro Ala Asn
                245                 250                 255

Asn Thr Val Ser Leu Gly Ala Val Gly Thr Ser Ala Val Ser Leu Gly
            260                 265                 270

Leu Thr Ala Asn Tyr Ala Arg Thr Gly Gly Gln Val Thr Ala Gly Asn
        275                 280                 285

Val Lys Ser Ile Ile Gly Val Thr Phe Val Tyr Gln
    290                 295                 300


<210> SEQ ID NO 26
<211> LENGTH: 733
<212> TYPE: PRT
<213> ORGANISM: Escherichia coli
<220> FEATURE:
<221> NAME/KEY: misc_feature
<222> LOCATION: (1)..(733)
<223> OTHER INFORMATION: IutA [Escherichia coli APEC O1]

<400> SEQUENCE: 26

Met Met Ile Ser Lys Lys Tyr Thr Leu Trp Ala Leu Asn Pro Leu Leu
1               5                   10                  15

Leu Thr Met Met Ala Pro Ala Val Ala Gln Gln Thr Asp Asp Glu Thr
            20                  25                  30

Phe Val Val Ser Ala Asn Arg Ser Asn Arg Thr Val Ala Glu Met Ala
        35                  40                  45

Gln Thr Thr Trp Val Ile Glu Asn Ala Glu Leu Glu Gln Gln Ile Gln
    50                  55                  60

Gly Gly Lys Glu Leu Lys Asp Ala Leu Ala Gln Leu Ile Pro Gly Leu
65                  70                  75                  80

Asp Val Ser Ser Arg Ser Arg Thr Asn Tyr Gly Met Asn Val Arg Gly
                85                  90                  95

Arg Pro Leu Val Val Leu Val Asp Gly Val Arg Leu Asn Ser Ser Arg
            100                 105                 110

Thr Asp Ser Arg Gln Leu Asp Ser Ile Asp Pro Phe Asn Ile Asp His
        115                 120                 125

Ile Glu Val Ile Ser Gly Ala Thr Ser Leu Tyr Gly Gly Gly Ser Thr
    130                 135                 140

Gly Gly Leu Ile Asn Ile Val Thr Lys Lys Gly Gln Pro Glu Thr Met
145                 150                 155                 160

Met Glu Phe Glu Ala Gly Thr Lys Ser Gly Phe Ser Ser Ser Lys Asp
                165                 170                 175
```

```
His Asp Glu Arg Ile Ala Gly Ala Val Ser Gly Gly Asn Glu His Ile
            180                 185                 190

Ser Gly Arg Leu Ser Val Ala Tyr Gln Lys Phe Gly Gly Trp Phe Asp
        195                 200                 205

Gly Asn Gly Asp Ala Thr Leu Leu Asp Asn Thr Gln Thr Gly Leu Gln
    210                 215                 220

Tyr Ser Asp Arg Leu Asp Ile Met Gly Thr Gly Thr Leu Asn Ile Asp
225                 230                 235                 240

Glu Ser Arg Gln Leu Gln Leu Ile Thr Gln Tyr Tyr Lys Ser Gln Gly
                245                 250                 255

Asp Asp Asp Tyr Gly Leu Asn Leu Gly Lys Gly Phe Ser Ala Ile Arg
            260                 265                 270

Gly Thr Ser Thr Pro Phe Val Ser Asn Gly Leu Asn Ser Asp Arg Ile
        275                 280                 285

Pro Gly Thr Glu Arg His Leu Ile Ser Leu Gln Tyr Ser Asp Ser Ala
    290                 295                 300

Phe Leu Gly Gln Glu Leu Val Gly Gln Val Tyr Tyr Arg Asp Glu Ser
305                 310                 315                 320

Leu Arg Phe Tyr Pro Phe Pro Thr Val Asn Ala Asn Lys Gln Val Thr
                325                 330                 335

Ala Phe Ser Ser Ser Gln Gln Asp Thr Asp Gln Tyr Gly Met Lys Leu
            340                 345                 350

Thr Leu Asn Ser Lys Pro Met Asp Gly Trp Gln Ile Thr Trp Gly Leu
        355                 360                 365

Asp Ala Asp His Glu Arg Phe Thr Ser Asn Gln Met Phe Phe Asp Leu
    370                 375                 380

Ala Gln Ala Ser Ala Ser Gly Gly Leu Asn Asn Lys Lys Ile Tyr Thr
385                 390                 395                 400

Thr Gly Arg Tyr Pro Ser Tyr Asp Ile Thr Asn Leu Ala Ala Phe Leu
                405                 410                 415

Gln Ser Gly Tyr Asp Ile Asn Asn Leu Phe Thr Leu Asn Gly Gly Val
            420                 425                 430

Arg Tyr Gln Tyr Thr Glu Asn Lys Ile Asp Asp Phe Ile Gly Tyr Ala
        435                 440                 445

Gln Gln Arg Gln Ile Ala Ala Gly Lys Ala Thr Ser Ala Asp Ala Ile
    450                 455                 460

Pro Gly Gly Ser Val Asp Tyr Asp Asn Phe Leu Phe Asn Ala Gly Leu
465                 470                 475                 480

Leu Met His Ile Thr Glu Arg Gln Gln Ala Trp Leu Asn Phe Ser Gln
                485                 490                 495

Gly Val Glu Leu Pro Asp Pro Gly Lys Tyr Tyr Gly Arg Gly Ile Tyr
            500                 505                 510

Gly Ala Ala Val Asn Gly His Leu Pro Leu Thr Lys Ser Val Asn Val
        515                 520                 525

Ser Asp Ser Lys Leu Glu Gly Val Lys Val Asp Ser Tyr Glu Leu Gly
    530                 535                 540

Trp Arg Phe Thr Gly Asn Asn Leu Arg Thr Gln Ile Ala Ala Tyr Tyr
545                 550                 555                 560

Ser Ile Ser Asp Lys Ser Val Val Ala Asn Lys Asp Leu Thr Ile Ser
                565                 570                 575

Val Val Asp Asp Lys Arg Arg Ile Tyr Gly Val Glu Gly Ala Val Asp
            580                 585                 590

Tyr Leu Ile Pro Asp Thr Asp Trp Ser Thr Gly Val Asn Phe Asn Val
```

```
        595                 600                 605

Leu Lys Thr Glu Ser Lys Val Asn Gly Thr Trp Gln Lys Tyr Asp Val
    610                 615                 620

Lys Thr Ala Ser Pro Ser Lys Ala Thr Ala Tyr Ile Gly Trp Ala Pro
625                 630                 635                 640

Asp Pro Trp Ser Leu Arg Val Gln Ser Thr Thr Ser Phe Asp Val Ser
                645                 650                 655

Asp Ala Gln Gly Tyr Lys Val Asp Gly Tyr Thr Thr Ala Asp Leu Leu
            660                 665                 670

Gly Ser Tyr Gln Leu Pro Val Gly Thr Leu Ser Phe Ser Ile Glu Asn
        675                 680                 685

Leu Phe Asp Arg Asp Tyr Thr Thr Val Trp Gly Gln Arg Ala Pro Leu
    690                 695                 700

Tyr Tyr Ser Pro Gly Tyr Gly Pro Ala Ser Leu Tyr Asp Tyr Lys Gly
705                 710                 715                 720

Arg Gly Arg Thr Phe Gly Leu Asn Tyr Ser Val Leu Phe
                725                 730


<210> SEQ ID NO 27
<211> LENGTH: 8224
<212> TYPE: DNA
<213> ORGANISM: Artificial Sequence
<220> FEATURE:
<223> OTHER INFORMATION: Synthetic: Leukotoxin-FimH Fusion

<400> SEQUENCE: 27

gaattccggg ggattatgcg ttaagcataa agtgtaaagc ctggggtgcc taatgagtga     60

gctaactcac attaattgcg ttgcgctcac tgcccgcttt ccagtcggga aacctgtcgt    120

gccagctgca ttaatgaatc ggccaacgcg cggggagagg cggtttgcgt attgggcgcc    180

agggtggttt ttcttttcac cagtgagacg ggcaacagct gattgccctt caccgcctgg    240

ccctgagaga gttgcagcaa gcggtccacg ctggtttgcc ccagcaggcg aaaatcctgt    300

ttgatggtgg ttgacggcgg gatataacat gagctgtctt cggtatcgtc gtatcccact    360

accgagatat ccgcaccaac gcgcagcccg gactcggtaa tggcgcgcat tgcgcccagc    420

gccatctgat cgttggcaac cagcatcgca gtgggaacga tgccctcatt cagcatttgc    480

atggtttgtt gaaaaccgga catggcactc cagtcgcctt cccgttccgc tatcggctga    540

atttgattgc gagtgagata tttatgccag ccagccagac gcagacgcgc cgagacagaa    600

cttaatgggc ccgctaacag cgcgatttgc tggtgaccca atgcgaccag atgctccacg    660

cccagtcgcg taccgtcttc atgggagaaa ataatactgt tgatgggtgt ctggtcagag    720

acatcaagaa ataacgccgg aacattagtg caggcagctt ccacagcaat ggcatcctgg    780

tcatccagcg gatagttaat gatcagccca ctgacgcgtt gcgcgagaag attgtgcacc    840

gccgctttac aggcttcgac gccgcttcgt tctaccatcg acaccaccac gctggcaccc    900

agttgatcgg cgcgagattt aatcgccgcg acaatttgcg acggcgcgtg cagggccaga    960

ctggaggtgg caacgccaat cagcaacgac tgtttgcccg ccagttgttg tgccacgcgg   1020

ttgggaatgt aattcagctc cgccatcgcc gcttccactt tttcccgcgt tttcgcagaa   1080

acgtggctgg cctggttcac cacgcgggaa acggtctgat aagagacacc ggcatactct   1140

gcgacatcgt ataacgttac tggtttcaca ttcaccaccc tgaattgact ctcttccggg   1200

cgctatcatg ccataccgcg aaaggttttg cgccattcga tggtgtcaac cttgcagagc   1260

tgcgccttta ttattatccg ccgggagaaa atattgtgga ggtttatcca ataggtattg   1320
```

```
gattgcaggg gctggaaacc cggtgatgga aacgcgtgtt gggcagaaaa tccctaaccc   1380
aacctggacg cctacgcagg cattcgtcag cgttcgctgg aggtgcggat taaattaccg   1440
ccagtcgttc tgccgaccaa ataacccgct agacgttacg cactgcctcg tgcatggtaa   1500
tggcgaatac ctcattcatg gtaccagtgc gccggacagc gtcggtttgc gcgtcagttc   1560
agggtgtatt cgcatgaatg caccggatat taaagccttg ttctccaggt gcggacggga   1620
acgtggtgaa agtgatcaac gaaccggtaa atattccgtg gatctaacgg gatgcgttat   1680
gttgaagtga gaccggtcga cgcatgccag gacaacttct ggtccggtaa cgtgctgagc   1740
ccggccaagc ttactcccca tccccctgtt gacaattaat catcggctcg tataatgtgt   1800
ggaattgtga gcggataaca atttcacagg aaacaggatc actaaggagg tttaaatatg   1860
gctactgtta tagatctaag cttcccaaaa actggggcaa aaaaaattat cctctatatt   1920
ccccaaaatt accaatatga tactgaacaa ggtaatggtt tacaggattt agtcaaagcg   1980
gccgaagagt tggggattga ggtacaaaga gaagaacgca ataatattgc aacagctcaa   2040
accagtttag gcacgattca aaccgctatt ggcttaactg agcgtggcat tgtgttatcc   2100
gctccacaaa ttgataaatt gctacagaaa actaaagcag gccaagcatt aggttctgcc   2160
gaaagcattg tacaaaatgc aaataaagcc aaaactgtat tatctggcat tcaatctatt   2220
ttaggctcag tattggctgg aatggattta gatgaggcct tacagaataa cagcaaccaa   2280
catgctcttg ctaaagctgg cttggagcta acaaattcat taattgaaaa tattgctaat   2340
tcagtaaaaa cacttgacga atttggtgag caaattagtc aatttggttc aaaactacaa   2400
aatatcaaag gcttagggac tttaggagac aaactcaaaa atatcggtgg acttgataaa   2460
gctggccttg gtttagatgt tatctcaggg ctattatcgg gcgcaacagc tgcacttgta   2520
cttgcagata aaaatgcttc aacagctaaa aaagtgggtg cgggttttga attggcaaac   2580
caagttgttg gtaatattac caaagccgtt tcttcttaca ttttagccca acgtgttgca   2640
gcaggtttat cttcaactgg gcctgtggct gctttaattg cttctactgt ttctcttgcg   2700
attagcccat tagcatttgc cggtattgcc gataaattta atcatgcaaa aagtttagag   2760
agttatgccg aacgctttaa aaaattaggc tatgacggag ataatttatt agcagaatat   2820
cagcggggaa cagggactat tgatgcatcg gttactgcaa ttaataccgc attggccgct   2880
attgctggtg gtgtgtctgc tgctgcagcc ggctcggtta ttgcttcacc gattgcctta   2940
ttagtatctg ggattaccgg tgtaatttct acgattctgc aatattctaa acaagcaatg   3000
tttgagcacg ttgcaaataa aattcataac aaaattgtag aatgggaaaa aaataatcac   3060
ggtaagaact actttgaaaa tggttacgat gcccgttatc ttgcgaattt acaagataat   3120
atgaaattct tactgaactt aaacaaagag ttacaggcag aacgtgtcat cgctattact   3180
cagcagcaat gggataacaa cattggtgat ttagctggta ttagccgttt aggtgaaaaa   3240
gtccttagtg gtaaagccta tgtggatgcg tttgaagaag gcaaacacat taaagccgat   3300
aaattagtac agttggattc ggcaaacggt attattgatg tgagtaattc gggtaaagcg   3360
aaaactcagc atatcttatt cagaacgcca ttattgacgc cgggaacaga gcatcgtgaa   3420
cgcgtacaaa caggtaaata tgaatatatt accaagctca atattaaccg tgtagatagc   3480
tggaaaatta cagatggtgc agcaagttct acctttgatt taactaacgt tgttcagcgt   3540
attggtattg aattagacaa tgctggaaat gtaactaaaa ccaaagaaac aaaaattatt   3600
gccaaacttg gtgaaggtga tgacaacgta tttgttggtt ctggtacgac ggaaattgat   3660
```

```
ggcggtgaag gttacgaccg agttcactat agccgtggaa actatggtgc tttaactatt   3720
gatgcaacca aagagaccga gcaaggtagt tataccgtaa atcgtttcgt agaaaccggt   3780
aaagcactac acgaagtgac ttcaacccat accgcattag tgggcaaccg tgaagaaaaa   3840
atagaatatc gtcatagcaa taaccagcac catgccggtt attacaccaa agataccttg   3900
aaagctgttg aagaaattat cggtacatca cataacgata tctttaaagg tagtaagttc   3960
aatgatgcct ttaacggtgg tgatggtgtc gatactattg acggtaacga cggcaatgac   4020
cgcttatttg gtggtaaagg cgatgatatt ctcgatggtg gaaatggtga tgattttatc   4080
gatggcggta aaggcaacga cctattacac ggtggcaagg gcgatgatat tttcgttcac   4140
cgtaaaggcg atggtaatga tattattacc gattctgacg gcaatgataa attatcattc   4200
tctgattcga acttaaaaga tttaacattt gaaaaagtta aacataatct tgtcatcacg   4260
aatagcaaaa aagagaaagt gaccattcaa aactggttcc gagaggctga ttttgctaaa   4320
gaagtgccta attataaagc aactaaagat gagaaaatcg aagaaatcat cggtcaaaat   4380
ggcgagcgga tcacctcaaa gcaagttgat gatcttatcg caaaaggtaa cggcaaaatt   4440
acccaagatg agctatcaaa agttgttgat aactatgaat tgctcaaaca tagcaaaaat   4500
gtgacaaaca gcttagataa gttaatctca tctgtaagtg catttacctc gtctaatgat   4560
tcgagaaatg tattagtggc tccaacttca atgttggatc aaagtttatc ttctcttcaa   4620
tttgctaggg gatccaaacg agttattacc ctgtttgctg tactgctgat gggctggtcg   4680
gtaaatgcct ggtcattcgc ctgtaaaacc gccaatggta ccgcaatccc tattggcggt   4740
ggcagcgcca atgtttatgt aaaccttgcg cctgccgtga atgtggggca aaagctggtc   4800
gtagatcttt cgacgcaaat cttttgccat aacgattacc cagaaaccat tacagactat   4860
gtcacactgc aacgaggttc ggcttatggc ggcgtgttat ctagtttttc cgggaccgta   4920
aaatataatg gcagtagcta tcctttccct actaccagcg aaacgccgcg ggttgtttat   4980
aattcgagaa cggataagcc gtggccggtg gcgctttatt tgacgccggt gagcagtgcg   5040
gggggagtgg cgattaaagc tggctcatta attgccgtgc ttattttgcg acagaccaac   5100
aactataaca gcgatgattt ccagtttgtg tggaatattt acgccaataa tgatgtggtg   5160
gtgcccactg gcggctgcga tgtttctgct cgtgatgtca ccgttactct gccggactac   5220
cctggttcag tgccgattcc tcttaccgtt tattgtgcga aaagccaaaa cctggggtat   5280
tacctctccg gcacaaccgc agatgcgggc aactcgattt tcaccaatac cgcgtcgttt   5340
tcacccgcgc agggcgtcgg cgtacagttg acgcgcaacg gtacgattat tccagcgaat   5400
aacacggtat cgttaggagc agtagggact tcggcggtaa gtctgggatt aacggcaaat   5460
tacgcacgta ccggagggca ggtgactgca gggaatgtgc aatcgattat tggcgtgact   5520
tttgtttatc aataaccatg gcatcacagt atcgtgatga cagaggcagg gagtgggaca   5580
aaattgaaat caaataatga ttttattttg actgatagtg acctgttcgt tgcaacaaat   5640
tgataagcaa tgctttttta taatgccaac ttagtataaa aaagctgaac gagaaacgta   5700
aaatgatata aatatcaata tattaaatta gattttgcat aaaaaacaga ctacataata   5760
ctgtaaaaca caacatatgc agtcactatg aatcaactac ttagatggta ttagtgacct   5820
gtaacagagc attagcgcaa ggtgattttt gtcttcttgc gctaattttt tgtcatcaaa   5880
cctgtcgcac tccagagaag cacaaagcct cgcaatccag tgcaaagctc tgcctcgcgc   5940
gtttcggtga tgacggtgaa aacctctgac acatgcagct cccggagacg gtcacagctt   6000
gtctgtaagc ggatgccggg agcagacaag cccgtcaggg cgcgtcagcg ggtgttggcg   6060
```

```
ggtgtcgggg cgcagccatg acccagtcac gtagcgatag cggagtgtat actggcttaa   6120
ctatgcggca tcagagcaga ttgtactgag agtgcaccat atgcggtgtg aaataccgca   6180
cagatgcgta aggagaaaat accgcatcag gcgctcttcc gcttcctggc tcactgactc   6240
gctgcgctcg gtcgttcggc tgcggcgagc ggtatcagct cactcaaagg cggtaatacg   6300
gttatccaca gaatcagggg ataacgcagg aaagaacatg tgagcaaaag gccagcaaaa   6360
ggccaggaac cgtaaaaagg ccgcgttgct ggcgtttttc cataggctcc gcccccctga   6420
cgagcatcac aaaaatcgac gctcaagtca gaggtggcga aacccgacag gactataaag   6480
ataccaggcg tttccccctg gaagctccct cgtgcgctct cctgttccga ccctgccgct   6540
taccggatac ctgtccgcct ttctcccttc gggaagcgtg gcgctttctc atagctcacg   6600
ctgtaggtat ctcagttcgg tgtaggtcgt tcgctccaag ctgggctgtg tgcacgaacc   6660
ccccgttcag cccgaccgct gcgccttatc cggtaactat cgtcttgagt ccaacccggt   6720
aagacacgac ttatcgccac tggcagcagc cactggtaac aggattagca gagcgaggta   6780
tgtaggcggt gctacagagt tcttgaagtg gtggcctaac tacggctaca ctagaaggac   6840
agtatttggt atctgcgctc tgctgaagcc agttaccttc ggaaaaagag ttggtagctc   6900
ttgatccggc aaacaaacca ccgctggtag cggtggtttt tttgtttgca agcagcagat   6960
tacgcgcaga aaaaaaggat ctcaagaaga tcctttgatc ggggctacgg ggtctgacgc   7020
tcagtggaac gaaaactcac gttaagggat tttggtcatg agattatcaa aaaggatctt   7080
cacctagatc cttttaaatt aaaaatgaag ttttaaatca atctaaagta tatatgagta   7140
aacttggtct gacagttacc aatgcttaat cagtgaggca cctatctcag cgatctgtct   7200
atttcgttca tccatagttg cctgactccc cgtcgtgtag ataactacga tacgggaggg   7260
cttaccatct ggccccagtg ctgcaatgat accgcgagac ccacgctcac cggctccaga   7320
tttatcagca ataaaccagc cagccggaag ggccgagcgc agaagtggtc ctgcaacttt   7380
atccgcctcc atccagtcta ttaattgttg ccgggaagct agagtaagta gttcgccagt   7440
taatagtttg cgcaacgttg ttgccattgc tgcaggcatc gtggtgtcac gctcgtcgtt   7500
tggtatggct tcattcagct ccggttccca acgatcaagg cgagttacat gatcccccat   7560
gttgtgcaaa aaagcggtta gctccttcgg tcctccgatc gttgtcagaa gtaagttggc   7620
cgcagtgtta tcactcatgg ttatggcagc actgcataat tctcttactg tcatgccatc   7680
cgtaagatgc ttttctgtga ctggtgagta ctcaaccaag tcattctgag aatagtgtat   7740
gcggcgaccg agttgctctt gcccggcgtc aacacgggat aataccgcgc cacatagcag   7800
aactttaaaa gtgctcatca ttggaaaacg ttcttcgggg cgaaaactct caaggatctt   7860
accgctgttg agatccagtt cgatgtaacc cactcgtgca cccaactgat cttcagcatc   7920
ttttactttc accagcgttt ctgggtgagc aaaaacagga aggcaaaatg ccgcaaaaaa   7980
gggaataagg gcgacacgga aatgttgaat actcatactc ttcctttttc aatattattg   8040
aagcatttat cagggttatt gtctcatgag cggatacata tttgaatgta tttagaaaaa   8100
taaacaaata ggggttccgc gcacatttcc ccgaaaagtg ccacctgacg tctaagaaac   8160
cattattatc atgacattaa cctataaaaa taggcgtatc acgaggccct ttcgtcttca   8220
agaa                                                                8224
```

<210> SEQ ID NO 28
<211> LENGTH: 8337
<212> TYPE: DNA

<213> ORGANISM: Artificial Sequence
<220> FEATURE:
<223> OTHER INFORMATION: Synthetic: Leukotoxin-PapG Fusion

<400> SEQUENCE: 28

```
gaattccggg ggattatgcg ttaagcataa agtgtaaagc ctggggtgcc taatgagtga     60
gctaactcac attaattgcg ttgcgctcac tgcccgcttt ccagtcggga aacctgtcgt    120
gccagctgca ttaatgaatc ggccaacgcg cggggagagg cggtttgcgt attgggcgcc    180
agggtggttt ttcttttcac cagtgagacg ggcaacagct gattgccctt caccgcctgg    240
ccctgagaga gttgcagcaa gcggtccacg ctggtttgcc ccagcaggcg aaaatcctgt    300
ttgatggtgg ttgacggcgg gatataacat gagctgtctt cggtatcgtc gtatcccact    360
accgagatat ccgcaccaac gcgcagcccg gactcggtaa tggcgcgcat tgcgcccagc    420
gccatctgat cgttggcaac cagcatcgca gtgggaacga tgccctcatt cagcatttgc    480
atggtttgtt gaaaaccgga catggcactc cagtcgcctt cccgttccgc tatcggctga    540
atttgattgc gagtgagata tttatgccag ccagccagac gcagacgcgc cgagacagaa    600
cttaatgggc ccgctaacag cgcgatttgc tggtgaccca atgcgaccag atgctccacg    660
cccagtcgcg taccgtcttc atgggagaaa ataatactgt tgatgggtgt ctggtcagag    720
acatcaagaa ataacgccgg aacattagtg caggcagctt ccacagcaat ggcatcctgg    780
tcatccagcg gatagttaat gatcagccca ctgacgcgtt gcgcgagaag attgtgcacc    840
gccgctttac aggcttcgac gccgcttcgt tctaccatcg acaccaccac gctggcaccc    900
agttgatcgg cgcgagattt aatcgccgcg acaatttgcg acggcgcgtg cagggccaga    960
ctggaggtgg caacgccaat cagcaacgac tgtttgcccg ccagttgttg tgccacgcgg   1020
ttgggaatgt aattcagctc cgccatcgcc gcttccactt tttcccgcgt tttcgcagaa   1080
acgtggctgg cctggttcac cacgcgggaa acggtctgat aagagacacc ggcatactct   1140
gcgacatcgt ataacgttac tggtttcaca ttcaccaccc tgaattgact ctcttccggg   1200
cgctatcatg ccataccgcg aaaggttttg cgccattcga tggtgtcaac cttgcagagc   1260
tgcgccttta ttattatccg ccgggagaaa atattgtgga ggtttatcca ataggtattg   1320
gattgcaggg gctggaaacc cggtgatgga aacgcgtgtt gggcagaaaa tccctaaccc   1380
aacctggacg cctacgcagg cattcgtcag cgttcgctgg aggtgcggat taaattaccg   1440
ccagtcgttc tgccgaccaa ataacccgct agacgttacg cactgcctcg tgcatggtaa   1500
tggcgaatac ctcattcatg gtaccagtgc gccggacagc gtcggtttgc gcgtcagttc   1560
agggtgtatt cgcatgaatg caccggatat taaagccttg ttctccaggt gcggacggga   1620
acgtggtgaa agtgatcaac gaaccggtaa atattccgtg gatctaacgg gatgcgttat   1680
gttgaagtga gaccggtcga cgcatgccag gacaacttct ggtccggtaa cgtgctgagc   1740
ccggccaagc ttactcccca tccccctgtt gacaattaat catcggctcg tataatgtgt   1800
ggaattgtga gcggataaca atttcacagg aaacaggatc actaaggagg tttaaatatg   1860
gctactgtta tagatctaag cttcccaaaa actggggcaa aaaaaattat cctctatatt   1920
ccccaaaatt accaatatga tactgaacaa ggtaatggtt tacaggattt agtcaaagcg   1980
gccgaagagt tggggattga ggtacaaaga gaagaacgca ataatattgc aacagctcaa   2040
accagtttag gcacgattca aaccgctatt ggcttaactg agcgtggcat tgtgttatcc   2100
gctccacaaa ttgataaatt gctacagaaa actaaagcag gccaagcatt aggttctgcc   2160
gaaagcattg tacaaaatgc aaataaagcc aaaactgtat tatctggcat tcaatctatt   2220
```

```
ttaggctcag tattggctgg aatggattta gatgaggcct tacagaataa cagcaaccaa   2280
catgctcttg ctaaagctgg cttggagcta acaaattcat taattgaaaa tattgctaat   2340
tcagtaaaaa cacttgacga atttggtgag caaattagtc aatttggttc aaaactacaa   2400
aatatcaaag gcttagggac tttaggagac aaactcaaaa atatcggtgg acttgataaa   2460
gctggccttg gtttagatgt tatctcaggg ctattatcgg gcgcaacagc tgcacttgta   2520
cttgcagata aaaatgcttc aacagctaaa aaagtgggtg cgggttttga attggcaaac   2580
caagttgttg gtaatattac caaagccgtt tcttcttaca ttttagccca acgtgttgca   2640
gcaggtttat cttcaactgg gcctgtggct gctttaattg cttctactgt ttctcttgcg   2700
attagcccat tagcatttgc cggtattgcc gataaattta atcatgcaaa aagtttagag   2760
agttatgccg aacgctttaa aaaattaggc tatgacggag ataatttatt agcagaatat   2820
cagcggggaa cagggactat tgatgcatcg gttactgcaa ttaataccgc attggccgct   2880
attgctggtg gtgtgtctgc tgctgcagcc ggctcggtta ttgcttcacc gattgcctta   2940
ttagtatctg ggattaccgg tgtaatttct acgattctgc aatattctaa acaagcaatg   3000
tttgagcacg ttgcaaataa aattcataac aaaattgtag aatgggaaaa aaataatcac   3060
ggtaagaact actttgaaaa tggttacgat gcccgttatc ttgcgaattt acaagataat   3120
atgaaattct tactgaactt aaacaaagag ttacaggcag aacgtgtcat cgctattact   3180
cagcagcaat gggataacaa cattggtgat ttagctggta ttagccgttt aggtgaaaaa   3240
gtccttagtg gtaaagccta tgtggatgcg tttgaagaag gcaaacacat taaagccgat   3300
aaattagtac agttggattc ggcaaacggt attattgatg tgagtaattc gggtaaagcg   3360
aaaactcagc atatcttatt cagaacgcca ttattgacgc cgggaacaga gcatcgtgaa   3420
cgcgtacaaa caggtaaata tgaatatatt accaagctca atattaaccg tgtagatagc   3480
tggaaaatta cagatggtgc agcaagttct acctttgatt taactaacgt tgttcagcgt   3540
attggtattg aattagacaa tgctggaaat gtaactaaaa ccaaagaaac aaaaattatt   3600
gccaaacttg gtgaaggtga tgacaacgta tttgttggtt ctggtacgac ggaaattgat   3660
ggcggtgaag gttacgaccg agttcactat agccgtggaa actatggtgc tttaactatt   3720
gatgcaacca aagagaccga gcaaggtagt tataccgtaa atcgtttcgt agaaaccggt   3780
aaagcactac acgaagtgac ttcaacccat accgcattag tgggcaaccg tgaagaaaaa   3840
atagaatatc gtcatagcaa taaccagcac catgccggtt attacaccaa agataccttg   3900
aaagctgttg aagaaattat cggtacatca cataacgata tctttaaagg tagtaagttc   3960
aatgatgcct ttaacggtgg tgatggtgtc gatactattg acggtaacga cggcaatgac   4020
cgcttatttg gtggtaaagg cgatgatatt ctcgatggtg gaaatggtga tgattttatc   4080
gatggcggta aaggcaacga cctattacac ggtggcaagg gcgatgatat tttcgttcac   4140
cgtaaaggcg atggtaatga tattattacc gattctgacg gcaatgataa attatcattc   4200
tctgattcga acttaaaaga tttaacattt gaaaaagtta aacataatct tgtcatcacg   4260
aatagcaaaa aagagaaagt gaccattcaa aactggttcc gagaggctga ttttgctaaa   4320
gaagtgccta attataaagc aactaaagat gagaaaatcg aagaaatcat cggtcaaaat   4380
ggcgagcgga tcacctcaaa gcaagttgat gatcttatcg caaaaggtaa cggcaaaatt   4440
acccaagatg agctatcaaa agttgttgat aactatgaat tgctcaaaca tagcaaaaat   4500
gtgacaaaca gcttagataa gttaatctca tctgtaagtg catttacctc gtctaatgat   4560
```

```
tcgagaaatg tattagtggc tccaacttca atgttggatc aaagtttatc ttctcttcaa   4620
tttgctaggg gatccaaaaa atggttccca gctttgttat tttccttgtg tgtgtctggt   4680
gagtcctctg catggaataa tattgtcttt tactcccttg gaaacgttaa ctcttatcag   4740
ggagggaatg tggtgattac tcaaaggcca caatttataa cttcgtggcg cccgggcatt   4800
gctacggtaa cctggaatca gtgtaatggt cctgggtttg ctgatggttc ctgggcttac   4860
tacagggagt atattgcgtg ggtagtattc cccaaaaagg ttatgaccaa aaatggatat   4920
cccttattta ttgaggttca taataaaggt agctggagtg aggagaatac tggtgacaat   4980
gacagctatt tttttctcaa ggggtataag tgggatgagc gggcctttga tgcaggtaat   5040
ttgtgtcaga aaccaggaga aacaacccgt ctgactgaga aatttgacga tattattttt   5100
aaagtcgccc tacctgcaga tcttccttta ggggattatt ctgttacaat tccatacact   5160
tccggcatgc agcgtcattt cgcgagttac ttgggggccc gttttaaaat cccatacaat   5220
gtggccaaaa ctctcccaag agagaatgaa atgttattct tatttaagaa tatcggcgga   5280
tgccgtcctt ctgcacagtc tctggaaata aagcatggtg atctgtctat taatagcgct   5340
aataatcatt atgcggctca gactctttct gtgtcttgcg atgtgcctgc aaatattcgt   5400
tttatgctgt taagaaatac aactccgaca tacagccatg gtaagaaatt ttcggttggt   5460
ctggggcatg gctgggactc cattgtttcg gttaacgggg tggacacagg agagacaacg   5520
atgagatggt acaaagcagg tacacaaaac ctgaccatcg gcagtcgcct ctatggtgaa   5580
tcttcaaaga tacaaccagg agtactatct ggttcagcaa cgctgctcat gatattgcca   5640
taagctagcc atggcatcac agtatcgtga tgacagaggc agggagtggg acaaaattga   5700
aatcaaataa tgattttatt ttgactgata gtgacctgtt cgttgcaaca aattgataag   5760
caatgctttt ttataatgcc aacttagtat aaaaaagctg aacgagaaac gtaaaatgat   5820
ataaatatca atatattaaa ttagattttg cataaaaaac agactacata atactgtaaa   5880
acacaacata tgcagtcact atgaatcaac tacttagatg gtattagtga cctgtaacag   5940
agcattagcg caaggtgatt tttgtcttct tgcgctaatt ttttgtcatc aaacctgtcg   6000
cactccagag aagcacaaag cctcgcaatc cagtgcaaag ctctgcctcg cgcgtttcgg   6060
tgatgacggt gaaaacctct gacacatgca gctcccggag acggtcacag cttgtctgta   6120
agcggatgcc gggagcagac aagcccgtca gggcgcgtca gcgggtgttg gcgggtgtcg   6180
gggcgcagcc atgacccagt cacgtagcga tagcggagtg tatactggct taactatgcg   6240
gcatcagagc agattgtact gagagtgcac catatgcggt gtgaaatacc gcacagatgc   6300
gtaaggagaa aataccgcat caggcgctct tccgcttcct ggctcactga ctcgctgcgc   6360
tcggtcgttc ggctgcggcg agcggtatca gctcactcaa aggcggtaat acggttatcc   6420
acagaatcag gggataacgc aggaaagaac atgtgagcaa aaggccagca aaaggccagg   6480
aaccgtaaaa aggccgcgtt gctggcgttt ttccataggc tccgcccccc tgacgagcat   6540
cacaaaaatc gacgctcaag tcagaggtgg cgaaacccga caggactata aagataccag   6600
gcgtttcccc ctggaagctc cctcgtgcgc tctcctgttc cgaccctgcc gcttaccgga   6660
tacctgtccg cctttctccc ttcgggaagc gtggcgcttt ctcatagctc acgctgtagg   6720
tatctcagtt cggtgtaggt cgttcgctcc aagctgggct gtgtgcacga accccccgtt   6780
cagcccgacc gctgcgcctt atccggtaac tatcgtcttg agtccaaccc ggtaagacac   6840
gacttatcgc cactggcagc agccactggt aacaggatta gcagagcgag gtatgtaggc   6900
ggtgctacag agttcttgaa gtggtggcct aactacggct acactagaag gacagtattt   6960
```

```
ggtatctgcg ctctgctgaa gccagttacc ttcggaaaaa gagttggtag ctcttgatcc   7020
ggcaaacaaa ccaccgctgg tagcggtggt ttttttgttt gcaagcagca gattacgcgc   7080
agaaaaaaag gatctcaaga agatcctttg atcggggcta cggggtctga cgctcagtgg   7140
aacgaaaact cacgttaagg gattttggtc atgagattat caaaaaggat cttcacctag   7200
atccttttaa attaaaaatg aagttttaaa tcaatctaaa gtatatatga gtaaacttgg   7260
tctgacagtt accaatgctt aatcagtgag gcacctatct cagcgatctg tctatttcgt   7320
tcatccatag ttgcctgact ccccgtcgtg tagataacta cgatacggga gggcttacca   7380
tctggcccca gtgctgcaat gataccgcga gacccacgct caccggctcc agatttatca   7440
gcaataaacc agccagccgg aagggccgag cgcagaagtg gtcctgcaac tttatccgcc   7500
tccatccagt ctattaattg ttgccgggaa gctagagtaa gtagttcgcc agttaatagt   7560
ttgcgcaacg ttgttgccat tgctgcaggc atcgtggtgt cacgctcgtc gtttggtatg   7620
gcttcattca gctccggttc ccaacgatca aggcgagtta catgatcccc catgttgtgc   7680
aaaaaagcgg ttagctcctt cggtcctccg atcgttgtca gaagtaagtt ggccgcagtg   7740
ttatcactca tggttatggc agcactgcat aattctctta ctgtcatgcc atccgtaaga   7800
tgcttttctg tgactggtga gtactcaacc aagtcattct gagaatagtg tatgcggcga   7860
ccgagttgct cttgcccggc gtcaacacgg gataataccg cgccacatag cagaacttta   7920
aaagtgctca tcattggaaa acgttcttcg gggcgaaaac tctcaaggat cttaccgctg   7980
ttgagatcca gttcgatgta acccactcgt gcacccaact gatcttcagc atcttttact   8040
ttcaccagcg tttctgggtg agcaaaaaca ggaaggcaaa atgccgcaaa aaagggaata   8100
agggcgacac ggaaatgttg aatactcata ctcttccttt ttcaatatta ttgaagcatt   8160
tatcagggtt attgtctcat gagcggatac atatttgaat gtatttagaa aaataaacaa   8220
ataggggttc cgcgcacatt tccccgaaaa gtgccacctg acgtctaaga aaccattatt   8280
atcatgacat taacctataa aaataggcgt atcacgaggc cctttcgtct tcaagaa      8337
```

```
<210> SEQ ID NO 29
<211> LENGTH: 9517
<212> TYPE: DNA
<213> ORGANISM: Artificial Sequence
<220> FEATURE:
<223> OTHER INFORMATION: Synthetic: Leukotoxin-IutA Fusion

<400> SEQUENCE: 29
```

```
gaattccggg ggattatgcg ttaagcataa agtgtaaagc ctggggtgcc taatgagtga     60
gctaactcac attaattgcg ttgcgctcac tgcccgcttt ccagtcggga aacctgtcgt    120
gccagctgca ttaatgaatc ggccaacgcg cggggagagg cggtttgcgt attgggcgcc    180
agggtggttt ttcttttcac cagtgagacg ggcaacagct gattgccctt caccgcctgg    240
ccctgagaga gttgcagcaa gcggtccacg ctggtttgcc ccagcaggcg aaaatcctgt    300
ttgatggtgg ttgacggcgg gatataacat gagctgtctt cggtatcgtc gtatcccact    360
accgagatat ccgcaccaac gcgcagcccg gactcggtaa tggcgcgcat tgcgcccagc    420
gccatctgat cgttggcaac cagcatcgca gtgggaacga tgccctcatt cagcatttgc    480
atggtttgtt gaaaaccgga catggcactc cagtcgcctt cccgttccgc tatcggctga    540
atttgattgc gagtgagata tttatgccag ccagccagac gcagacgcgc cgagacagaa    600
cttaatgggc ccgctaacag cgcgatttgc tggtgaccca atgcgaccag atgctccacg    660
```

```
cccagtcgcg taccgtcttc atgggagaaa ataatactgt tgatgggtgt ctggtcagag    720
acatcaagaa ataacgccgg aacattagtg caggcagctt ccacagcaat ggcatcctgg    780
tcatccagcg gatagttaat gatcagccca ctgacgcgtt gcgcgagaag attgtgcacc    840
gccgctttac aggcttcgac gccgcttcgt tctaccatcg acaccaccac gctggcaccc    900
agttgatcgg cgcgagattt aatcgccgcg acaatttgcg acggcgcgtg cagggccaga    960
ctggaggtgg caacgccaat cagcaacgac tgtttgcccg ccagttgttg tgccacgcgg   1020
ttgggaatgt aattcagctc cgccatcgcc gcttccactt tttcccgcgt tttcgcagaa   1080
acgtggctgg cctggttcac cacgcgggaa acggtctgat aagagacacc ggcatactct   1140
gcgacatcgt ataacgttac tggtttcaca ttcaccaccc tgaattgact ctcttccggg   1200
cgctatcatg ccataccgcg aaaggttttg cgccattcga tggtgtcaac cttgcagagc   1260
tgcgccttta ttattatccg ccgggagaaa atattgtgga ggtttatcca ataggtattg   1320
gattgcaggg gctggaaacc cggtgatgga aacgcgtgtt gggcagaaaa tccctaaccc   1380
aacctggacg cctacgcagg cattcgtcag cgttcgctgg aggtgcggat taaattaccg   1440
ccagtcgttc tgccgaccaa ataacccgct agacgttacg cactgcctcg tgcatggtaa   1500
tggcgaatac ctcattcatg gtaccagtgc gccggacagc gtcggtttgc gcgtcagttc   1560
agggtgtatt cgcatgaatg caccggatat taaagccttg ttctccaggt gcggacggga   1620
acgtggtgaa agtgatcaac gaaccggtaa atattccgtg gatctaacgg gatgcgttat   1680
gttgaagtga gaccggtcga cgcatgccag gacaacttct ggtccggtaa cgtgctgagc   1740
ccggccaagc ttactcccca tccccctgtt gacaattaat catcggctcg tataatgtgt   1800
ggaattgtga gcggataaca atttcacagg aaacaggatc actaaggagg tttaaatatg   1860
gctactgtta tagatctaag cttcccaaaa actggggcaa aaaaaattat cctctatatt   1920
ccccaaaatt accaatatga tactgaacaa ggtaatggtt tacaggattt agtcaaagcg   1980
gccgaagagt tggggattga ggtacaaaga gaagaacgca ataatattgc aacagctcaa   2040
accagtttag gcacgattca aaccgctatt ggcttaactg agcgtggcat tgtgttatcc   2100
gctccacaaa ttgataaatt gctacagaaa actaaagcag gccaagcatt aggttctgcc   2160
gaaagcattg tacaaaatgc aaataaagcc aaaactgtat tatctggcat tcaatctatt   2220
ttaggctcag tattggctgg aatggattta gatgaggcct tacagaataa cagcaaccaa   2280
catgctcttg ctaaagctgg cttggagcta acaaattcat taattgaaaa tattgctaat   2340
tcagtaaaaa cacttgacga atttggtgag caaattagtc aatttggttc aaaactacaa   2400
aatatcaaag gcttagggac tttaggagac aaactcaaaa atatcggtgg acttgataaa   2460
gctggccttg gtttagatgt tatctcaggg ctattatcgg gcgcaacagc tgcacttgta   2520
cttgcagata aaaatgcttc aacagctaaa aaagtgggtg cgggttttga attggcaaac   2580
caagttgttg gtaatattac caaagccgtt tcttcttaca ttttagccca acgtgttgca   2640
gcaggtttat cttcaactgg gcctgtggct gctttaattg cttctactgt ttctcttgcg   2700
attagcccat tagcatttgc cggtattgcc gataaattta atcatgcaaa aagtttagag   2760
agttatgccg aacgctttaa aaaattaggc tatgacggag ataatttatt agcagaatat   2820
cagcggggaa cagggactat tgatgcatcg gttactgcaa ttaataccgc attggccgct   2880
attgctggtg gtgtgtctgc tgctgcagcc ggctcggtta ttgcttcacc gattgcctta   2940
ttagtatctg ggattaccgg tgtaatttct acgattctgc aatattctaa acaagcaatg   3000
tttgagcacg ttgcaaataa aattcataac aaaattgtag aatgggaaaa aaataatcac   3060
```

```
ggtaagaact actttgaaaa tggttacgat gcccgttatc ttgcgaattt acaagataat   3120
atgaaattct tactgaactt aaacaaagag ttacaggcag aacgtgtcat cgctattact   3180
cagcagcaat gggataacaa cattggtgat ttagctggta ttagccgttt aggtgaaaaa   3240
gtccttagtg gtaaagccta tgtggatgcg tttgaagaag gcaaacacat taaagccgat   3300
aaattagtac agttggattc ggcaaacggt attattgatg tgagtaattc gggtaaagcg   3360
aaaactcagc atatcttatt cagaacgcca ttattgacgc cgggaacaga gcatcgtgaa   3420
cgcgtacaaa caggtaaata tgaatatatt accaagctca atattaaccg tgtagatagc   3480
tggaaaatta cagatggtgc agcaagttct acctttgatt taactaacgt tgttcagcgt   3540
attggtattg aattagacaa tgctggaaat gtaactaaaa ccaaagaaac aaaaattatt   3600
gccaaacttg gtgaaggtga tgacaacgta tttgttggtt ctggtacgac ggaaattgat   3660
ggcggtgaag gttacgaccg agttcactat agccgtggaa actatggtgc tttaactatt   3720
gatgcaacca aagagaccga gcaaggtagt tataccgtaa atcgtttcgt agaaaccggt   3780
aaagcactac acgaagtgac ttcaacccat accgcattag tgggcaaccg tgaagaaaaa   3840
atagaatatc gtcatagcaa taaccagcac catgccggtt attacaccaa agataccttg   3900
aaagctgttg aagaaattat cggtacatca cataacgata tctttaaagg tagtaagttc   3960
aatgatgcct ttaacggtgg tgatggtgtc gatactattg acggtaacga cggcaatgac   4020
cgcttatttg gtggtaaagg cgatgatatt ctcgatggtg gaaatggtga tgattttatc   4080
gatggcggta aaggcaacga cctattacac ggtggcaagg gcgatgatat tttcgttcac   4140
cgtaaaggcg atggtaatga tattattacc gattctgacg gcaatgataa attatcattc   4200
tctgattcga acttaaaaga tttaacattt gaaaaagtta aacataatct tgtcatcacg   4260
aatagcaaaa aagagaaagt gaccattcaa aactggttcc gagaggctga ttttgctaaa   4320
gaagtgccta attataaagc aactaaagat gagaaaatcg aagaaatcat cggtcaaaat   4380
ggcgagcgga tcacctcaaa gcaagttgat gatcttatcg caaaaggtaa cggcaaaatt   4440
acccaagatg agctatcaaa agttgttgat aactatgaat tgctcaaaca tagcaaaaat   4500
gtgacaaaca gcttagataa gttaatctca tctgtaagtg catttacctc gtctaatgat   4560
tcgagaaatg tattagtggc tccaacttca atgttggatc aaagtttatc ttctcttcaa   4620
tttgctaggg gatccataag caaaaagtat acgctttggg ctctcaaccc actgcttctt   4680
accatgatgg cgccagcagt cgctcaacaa accgatgatg aaacgttcgt ggtgtctgcc   4740
aaccgcagca atcgcaccgt agcggagatg gcgcaaacca cctgggttat cgaaaacgcc   4800
gaactggaac agcagattca gggcggcaaa gagcttaaag acgcactggc tcagctgatc   4860
cctggccttg acgtcagcag ccggagccgc accaactacg gtatgaatgt gcgtggccgc   4920
ccgctggtcg tgctggttga cggcgtgcgt ctcaactctt cacgtaccga cagccgacaa   4980
ctggactcta tagatccttt taatatgcac catattgaag tgatcttcgg tgcgacgtcc   5040
ctgtacggcg gcggcagtac cggtggcctg atcaacatcg tgaccaaaaa aggccagccg   5100
gaaaccatga tggagtttga ggctggcacc aaaagtggct ttagcagcag taaagatcac   5160
gatgaacgca ttgccggagc tgtctccggc ggaaatgagc atatctccgg acgtctttcc   5220
gtggcatatc agaaatttgg cggctggttt gacggtaacg gcgatgccac cttgcttgat   5280
aacacccaga ccggcctgca gtactccgat cggctggaca tcatgggaac tggtacgctg   5340
aacatcgatg aatcccggca gcttcagttg atcacacagt actataaaag ccagggcgac   5400
```

```
gacgattacg ggcttaatct cgggaaaggc ttctctgcca tcagagggac cagcacgcca   5460

ttcgtcagta acgggctgaa ttccgaccgt attcccggca ctgacgggca tttgatcagc   5520

ctgcagtact ctgacagcgc ttttctggga caggagctgg tcggtcaggt ttactaccgc   5580

gatgagtcgt tgcgattcta cccgttcccg acggtaaatg cgaacaaaca ggtgacggct   5640

ttctcttcgt cacagcagga caccgaccag tacggcatga aactgactct gaacagcaaa   5700

ccgatggacg gctggcaaat cacctggggg ctggatgctg atcatgagcg ctttacctcc   5760

aaccagatgt tcttcgacct ggctcaggca agcgcttccg gagggctgaa caacaagaag   5820

atttacacca ccgggcgcta tccgtcgtat gacatcacca acctggcggc cttcctgcaa   5880

tcaggctatg acatcaataa tctctttacc ctcaacggtg gcgtacgcta tcagtacact   5940

gaaaacaaga ttgatgattt catcggctac gcgcagcaac ggcagattgg cgccgggaag   6000

gctacatccg ccgacgcatt ctggcggctc agtcgattac gacacttcct gttcaacgcc   6060

ggtctgctga tgcacatcac cgaaccgcag caggcatggc tcaacttctc ccagggcctg   6120

gagctgccgg acccgggtaa atactatggt cgcggcatct atggtgctgc agtgaacggc   6180

catcttcctc taacaaagag tgtgaacgtc agcgacagca agctggaagg cgtgaaagtc   6240

gattcttatg agctgggctg gcgctttact ggcaataatc tgcgtaccca aatcgcggcc   6300

tactattcga tttctgataa gagcgtggtg gcgaataaag atctgaccat cagcgtggtg   6360

gacgacaaac gccgtattta cggcgtggaa ggtgcggtgg actacctgat tcctgatact   6420

gactggagta ccggagtgaa cttcaacgtg ctgaaaactg agtcgaaagt gaacggtacc   6480

tggcagaaat acgatgtgaa gacagcaagc ccatcaaaag cgacagccta cattggctgg   6540

gcaccggacc cgtggagtct gcgcgtgcag agcaccacct cctttgacgt gagcgacgcg   6600

cagggctaca aggtcgatgg ctataccacc gtggatctgc tcggcagtta tcagcttccg   6660

gtgggtacac tcagcttcag cattgaaaac ctcttcgacc gtgactacac cactgtctgg   6720

gggcagcgtg caccactgta ctacagcccg ggttacggcc cagcgtcact gtacgactac   6780

aaaggcaggg gccgaacctt tggtctgaac tactctgtgc tgttctgacc atggcatcac   6840

agtatcgtga tgacagaggc agggagtggg acaaaattga aatcaaataa tgattttatt   6900

ttgactgata gtgacctgtt cgttgcaaca aattgataag caatgctttt ttataatgcc   6960

aacttagtat aaaaaagctg aacgagaaac gtaaaatgat ataaatatca atatattaaa   7020

ttagattttg cataaaaaac agactacata atactgtaaa acacaacata tgcagtcact   7080

atgaatcaac tacttagatg gtattagtga cctgtaacag agcattagcg caaggtgatt   7140

tttgtcttct tgcgctaatt ttttgtcatc aaacctgtcg cactccagag aagcacaaag   7200

cctcgcaatc cagtgcaaag ctctgcctcg cgcgtttcgg tgatgacggt gaaaacctct   7260

gacacatgca gctcccggag acggtcacag cttgtctgta agcggatgcc gggagcagac   7320

aagcccgtca gggcgcgtca gcgggtgttg gcgggtgtcg gggcgcagcc atgacccagt   7380

cacgtagcga tagcggagtg tatactggct taactatgcg gcatcagagc agattgtact   7440

gagagtgcac catatgcggt gtgaaatacc gcacagatgc gtaaggagaa aataccgcat   7500

caggcgctct tccgcttcct ggctcactga ctcgctgcgc tcggtcgttc ggctgcggcg   7560

agcggtatca gctcactcaa aggcggtaat acggttatcc acagaatcag gggataacgc   7620

aggaaagaac atgtgagcaa aaggccagca aaaggccagg aaccgtaaaa aggccgcgtt   7680

gctggcgttt ttccataggc tccgcccccc tgacgagcat cacaaaaatc gacgctcaag   7740

tcagaggtgg cgaaacccga caggactata aagataccag gcgtttcccc ctggaagctc   7800
```

```
cctcgtgcgc tctcctgttc cgaccctgcc gcttaccgga tacctgtccg cctttctccc   7860

ttcgggaagc gtggcgcttt ctcatagctc acgctgtagg tatctcagtt cggtgtaggt   7920

cgttcgctcc aagctgggct gtgtgcacga accccccgtt cagcccgacc gctgcgcctt   7980

atccggtaac tatcgtcttg agtccaaccc ggtaagacac gacttatcgc cactggcagc   8040

agccactggt aacaggatta gcagagcgag gtatgtaggc ggtgctacag agttcttgaa   8100

gtggtggcct aactacggct acactagaag gacagtattt ggtatctgcg ctctgctgaa   8160

gccagttacc ttcggaaaaa gagttggtag ctcttgatcc ggcaaacaaa ccaccgctgg   8220

tagcggtggt ttttttgttt gcaagcagca gattacgcgc agaaaaaaag gatctcaaga   8280

agatcctttg atcggggcta cggggtctga cgctcagtgg aacgaaaact cacgttaagg   8340

gattttggtc atgagattat caaaaaggat cttcacctag atccttttaa attaaaaatg   8400

aagttttaaa tcaatctaaa gtatatatga gtaaacttgg tctgacagtt accaatgctt   8460

aatcagtgag gcacctatct cagcgatctg tctatttcgt tcatccatag ttgcctgact   8520

ccccgtcgtg tagataacta cgatacggga gggcttacca tctggcccca gtgctgcaat   8580

gataccgcga gacccacgct caccggctcc agatttatca gcaataaacc agccagccgg   8640

aagggccgag cgcagaagtg gtcctgcaac tttatccgcc tccatccagt ctattaattg   8700

ttgccgggaa gctagagtaa gtagttcgcc agttaatagt ttgcgcaacg ttgttgccat   8760

tgctgcaggc atcgtggtgt cacgctcgtc gtttggtatg gcttcattca gctccggttc   8820

ccaacgatca aggcgagtta catgatcccc catgttgtgc aaaaaagcgg ttagctcctt   8880

cggtcctccg atcgttgtca gaagtaagtt ggccgcagtg ttatcactca tggttatggc   8940

agcactgcat aattctctta ctgtcatgcc atccgtaaga tgcttttctg tgactggtga   9000

gtactcaacc aagtcattct gagaatagtg tatgcggcga ccgagttgct cttgcccggc   9060

gtcaacacgg gataataccg cgccacatag cagaacttta aaagtgctca tcattggaaa   9120

acgttcttcg gggcgaaaac tctcaaggat cttaccgctg ttgagatcca gttcgatgta   9180

acccactcgt gcacccaact gatcttcagc atcttttact ttcaccagcg tttctgggtg   9240

agcaaaaaca ggaaggcaaa atgccgcaaa aaagggaata agggcgacac ggaaatgttg   9300

aatactcata ctcttccttt ttcaatatta ttgaagcatt tatcagggtt attgtctcat   9360

gagcggatac atatttgaat gtatttagaa aaataaacaa ataggggttc cgcgcacatt   9420

tccccgaaaa gtgccacctg acgtctaaga aaccattatt atcatgacat taacctataa   9480

aaataggcgt atcacgaggc cctttcgtct tcaagaa                             9517

<210> SEQ ID NO 30
<211> LENGTH: 33
<212> TYPE: DNA
<213> ORGANISM: Escherichia coli
<220> FEATURE:
<221> NAME/KEY: misc_feature
<222> LOCATION: (1)..(33)
<223> OTHER INFORMATION: papG F

<400> SEQUENCE: 30

gcgcagggat ccaaaaaatg gttcccagct ttg                                   33
```

VACCINES AGAINST PATHOGENIC *ESCHERICHIA COLI* AND METHODS OF USING THE SAME

CROSS-REFERENCE TO RELATED APPLICATION:

The present application is related to and claims the benefit and priority of U.S. Provisional Patent Application No. 62/057,857, filed Sep. 30, 2014, the entirety of which is hereby incorporated herein by reference.

REFERENCE TO SEQUENCE LISTING SUBMITTED VIA EFS-WEB

This application includes an electronically submitted sequence listing in .txt format. The .txt file contains a sequence listing entitled "2015-12-14 432743.10035_ST25.txt" created on Dec. 14, 2015 and is 86,809 bytes in size. The sequence listing contained in this .txt file is part of the specification and is hereby incorporated by reference herein in its entirety.

FIELD

Provided herein are compositions and methods for vaccinating a subject against pathogenic *Escherichia coli* (*E. coli*).

BACKGROUND

*E. coli* is a gram-negative, rod-shaped bacterium that is commonly found in the lower intestine of warm-blooded organisms. Most *E. coli* strains are harmless. However, some strains are pathogenic and can cause serious illness in humans and other animals. Illnesses caused by pathogenic *E. coli* include, for example, gastrointestinal infections, skin infections, respiratory infections, urinary tract infections, neonatal meningitis, inflammation, septicemia, mastitis, colibacillosis, perihepatitis, pericarditis, and peritonitis.

In particular, avian pathogenic *E. coli* (APEC) is a group of *E. coli* strains that cause a variety of respiratory and skin diseases in chickens, turkeys, and other avian species. APEC are the most common bacterial pathogen in chickens, costing the poultry industry hundreds of millions of dollars in economic losses worldwide. The economic losses from colibacillosis, caused by APEC, arise from the increased mortality and decreased growth rate of the affected birds. For example, in Brazil, which is the world's largest exporter of chicken meat, APEC are responsible for 45.2% of condemned poultry carcasses. See Fallavena et al., *Avian Pathol.,* 2000, 29:557-562, incorporated by reference in its entirety.

In addition to the economic losses, APEC isolates are suspected to be a major source for spreading antimicrobial resistance to other human and animal pathogens, mainly through their plasmids and the exchange of genetic material with other bacteria. Even in countries and regions with strict limits on antibiotic use in the poultry industry, such as the U.S., Australia, and Europe, up to 92% of avian *E. coli* isolates are resistant to three or more antimicrobial drugs. See Gyles et al., *Anim. Health Res. Rev.,* 2008, 9:149-158, incorporated by reference in its entirety.

APEC are abundant on chicken farms, and inhalation of dust particles loaded with bacteria is the main route of infection. The disease develops quickly, within 24-48 hours, and can only be cured though the use of antimicrobial drugs. The short lifespan of meat-type chickens (37-40 days) makes using antibiotics a very unlikely scenario, as the infection typically occurs around 21-28 days of age and antimicrobial treatment requires a withdrawal period of at least 14 days before the birds are shipped off the farm. Moreover, increased use of antibiotics, due to APEC, contributes to the emergence of antibiotic-resistant strains of pathogenic *E. coli.*

Accordingly prevention of APEC is a better option than treatment. Provided herein are vaccines that prevent APEC, and infection with other forms of pathogenic *E. coli*. Also provided herein are methods of using these vaccines to prevent infection of avians with APEC and infection of other subjects with pathogenic *E. coli.*

While vaccines against APEC do exist, most APEC vaccines involve the use of whole microorganisms. The subunit vaccines described herein are advantageous in that they induce a more targeted and uniform immune response, and can be manufactured more consistently.

SUMMARY

Provided herein are vaccines that target proteins that are important for infection by pathogenic *E. coli*. In some embodiments, the pathogenic *E. coli* are APEC.

In some embodiments, provided herein is a composition comprising at least one of: (a) an immunogenic portion of at least two isolated proteins selected from a PapG protein, a FimH protein, and an IutA protein, or variants thereof, or (b) at least one isolated polynucleotide encoding the at least two isolated proteins of (a).

In some embodiments, provided herein is a composition comprising an immunogenic portion of at least two isolated proteins selected from a PapG protein, a FimH protein, and an IutA protein, or variants thereof.

In some embodiments, provided herein is a composition comprising at least one polynucleotide encoding at least two isolated proteins selected from a PapG protein, a FimH protein, and an IutA protein, or variants thereof.

In some embodiments, the PapG protein has the sequence provided in SEQ ID NO: 4, the FimH protein has the sequence provided in SEQ ID NO: 2, and/or the IutA protein has the sequence provided in SEQ ID NO: 6.

In some embodiments, a variant has at least 80%, 90%, 95%, or 99% sequence identity with the PapG protein of SEQ ID NO: 4, the FimH protein of SEQ ID NO: 2, or the IutA protein of SEQ ID NO: 6.

In some embodiments, the composition further comprises a leukotoxin A protein. In some aspects, the leukotoxin A is part of a fusion protein with a protein that is an immunogen, such as PapG, FimH, and/or IutA. In some aspects, the leukotoxin A is a leukotoxin A from an organism selected from *Pasteurella* sp., *P. haemolytica, Aggregatibacter* sp., *A. actinomycetemcomitans, Fusobacterium* sp., *F. necrophorum, Mannheimia* sp., *M. glucosidal, M. ruminalis*, and *M. haemolytica*. Also provided are nucleic acids encoding the fusions.

In some embodiments, the composition further comprises an adjuvant. In some embodiments, the adjuvant is selected from chitosan, an oil emulsion, a toxin, an aluminum salt, alum, a mineral oil, squalane, thimerosal, interleukin-1, interleukin-2, interleukin-12, Freund's complete adjuvant, Freund's incomplete adjuvant, and a polymer.

In some embodiments, the composition is formulated for intranasal or intramuscular delivery.

Also provided are methods for vaccinating against a pathogenic *Escherichia coli,* comprising administering an effective amount of a composition provided herein to a subject.

In some embodiments, the subject is selected from an avian and a mammal. In some aspects, the avian is selected from a chicken and a turkey. In some aspects, the mammal is selected from a cow, a pig, a horse, a sheep, a camel, and a human.

In some embodiments, the subject is an avian, and the *Escherichia coli* is an avian pathogenic *Escherichia coli* (APEC).

In some embodiments, the subject is a human and the *Escherichia coli* causes a urinary tract infection.

In some embodiments, the composition induces a mucosal antibody response. In some aspects, wherein the mucosal antibody response is selected from the induction of secretory IgA antibody activity in the intestine, the induction of IgA antibody activity in the respiratory tract, and combinations thereof.

In some embodiments, the composition induces a serum antibody response. In some aspects, the serum antibody response comprises the induction of IgY, IgM, and IgA antibody activity in the serum.

BRIEF DESCRIPTION OF THE DRAWINGS

FIG. 5 provides an SDS-PAGE gel showing overexpression of IutA protein fused to the *Pasteurella haemolytica* leukotoxin gene, as indicated by the arrow. Induced protein can be seen at the top of lanes 3, 5, and 9.

DETAILED DESCRIPTION

1. Definitions

Figure 1:
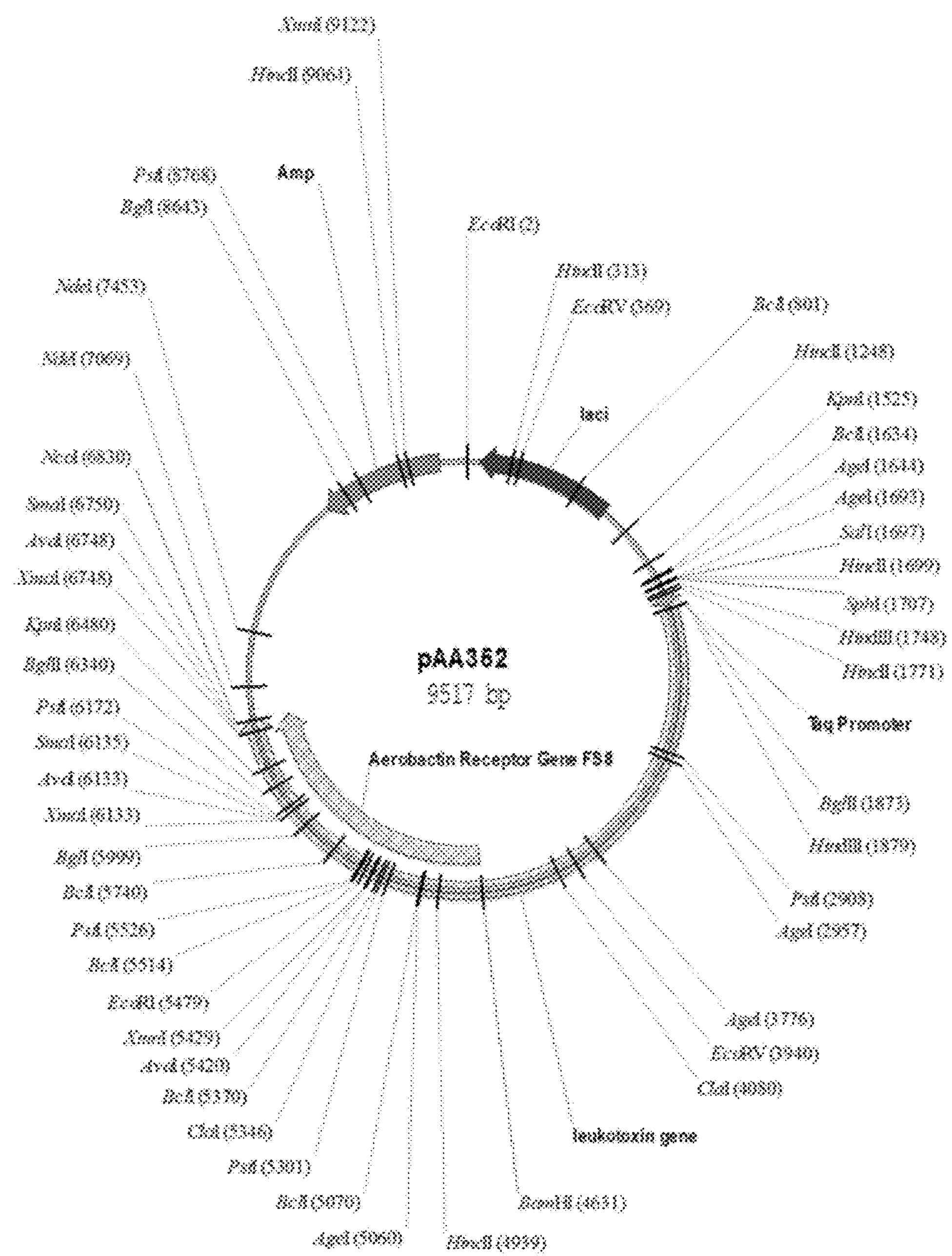
FIG. 1 provides a map of plasmid pAA352 with the inserted aerobactin receptor gene (iutA). The plasmid has a *Pasteurella haemolytica* leukotoxin gene fused to iutA so that they can be expressed as a fusion protein. The plasmid also contains an inducible promoter and ampicillin resistance gene.

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a difference over what is generally understood in the art. The techniques and procedures known in the art that are described or referenced herein are generally well understood and commonly employed using conventional methodologies by those skilled in the art.

As used herein, the singular forms "a," "an," and "the" include the plural referents unless the context clearly indicates otherwise.

As used herein, the term "about" refers to the stated value plus or minus 10%. For example, a value of "about 10" encompasses a range of 9 to 11.

As used herein, "vaccinating" or "vaccinate" refers, in certain embodiments, to preventing infection of a subject with a pathogenic *E. coli*. In some embodiments, the infection is not completely prevented, but the exposure of the subject's immune system to a vaccine provided herein primes the immune system to control or eliminate the pathogenic *E. coli* after infection. In some embodiments, the prevention, control, or elimination of a pathogenic *E. coli* infection can be evaluated by one or more physical parameters. The physical parameters can include, for example, diarrhea, inflammation, tissue damage, pain, breathing rate, heart rate, and the like. Prevention, control, or elimination of a pathogenic *E. coli* infection may also be assessed by quantifying the amount of the pathogenic *E. coli* itself in a subject, or a tissue or fluid from the subject. This quantification can be performed using standard methods, such as, for example, bacterial culture techniques, immunoassays, and nucleic acid-based amplification methods.

As used herein, the term "effective amount" refers to an amount of a composition provided herein that is useful for vaccinating against an infection with a pathogenic *E. coli.*

As used herein, the term "subject" means any subject suitable for vaccination with the compositions and methods provided herein. Subjects include, for example, avians and mammals. Avians include, for example, chickens and turkeys. Mammals include, for example, humans, monkeys, cows, horses, camels, goats, and sheep. In certain embodiments, the subject is an avian. In some aspects, the avian is selected from a chicken and a turkey.

The term "sequence identity," as used herein, is generally expressed as a percentage and refers to the percent of amino acid residues or nucleotides, as appropriate, that are identical between two sequences when optimally aligned. For the purposes of this disclosure, optimal alignment is achieved by using the Clustal Omega alignment tool described in Sievers et al., *Mol. Sys. Biol.,* 2011, 7:539(1-6); Goujon et al., *Nuc. Acids Res.,* 2010, 38(Suppl.):W695-699; and McWilliam et al., *Nuc. Acids Res.,* 2013, 41:W597-600, each of which is incorporated by reference in its entirety.

The term "isolated," when used to refer to proteins or nucleic acids, means a protein or nucleic acid that has been separated and/or recovered from a component of its natural environment. Components of the natural environment may include enzymes, hormones, and other proteinaceous or nonproteinaceous materials. In some embodiments, an isolated protein or nucleic acid is purified to homogeneity by gel electrophoresis (e.g., agarose gel electrophoresis for nucleic acids, and polyacrylamide gel electrophoresis for proteins).

2. Immunogens

Provided herein are vaccines that induce an immune response to proteins expressed by pathogenic *E. coli*. In some embodiments, the vaccine induces an immune response to at least one protein found at the tip of the *E. coli* fimbriae (e.g., PapG and/or FimH). These proteins may be important for the attachment of *E. coli* to the lung tissue of hosts. In some embodiments, the vaccines induce an immune response to at least one protein component of the outer membrane receptor of the iron acquisition system of *E. coli* (e.g., IutA).

In some embodiments, a vaccine provided herein induces an immune response to at least one protein selected from PapG, FimH, and IutA. In some aspects, a vaccine provided herein induces an immune response to at least two proteins selected from PapG, FimH, and IutA. In some aspects, a vaccine provided herein induces an immune response to all three of PapG, FimH, and IutA.

2.1. PapG

As described above, a vaccine provided herein can induce an immune response against any suitable PapG protein. In some embodiments, the PapG protein is a PapG protein expressed by a pathogenic *E. coli*. In some embodiments, the pathogenic *E. coli* is an APEC.

In some embodiments, the PapG protein used to vaccinate the subject comprises, consists essentially of, or consists of a PapG protein encoded by SEQ ID NO: 3 (GenBank Accession No. X61237; GI: 42307), SEQ ID NO: 21 (GenBank Accession No. AY212280.1; GI: 37786764), or SEQ ID NO: 22 (GenBank Accession No. AY212279.1; GI: 37786762). In some embodiments, the PapG protein used to vaccinate the subject comprises, consists essentially of, or consists of a PapG protein encoded by a variant of SEQ ID NO: 3, SEQ ID NO: 21, or SEQ ID NO: 22. In some embodiments, the PapG protein used to vaccinate the subject comprises, consists essentially of, or consists of a portion of a PapG protein encoded by a portion of SEQ ID NO: 3, SEQ ID NO: 21, or SEQ ID NO: 22; or a portion of a PapG protein encoded by a variant of a portion of SEQ ID NO: 3, SEQ ID NO: 21, or SEQ ID NO: 22.

In some embodiments, a variant PapG protein is encoded by a polynucleotide with at least 80% sequence identity to the polynucleotide of SEQ ID NO: 3, SEQ ID NO: 21, or SEQ ID NO: 22. In some aspects, a variant PapG protein is encoded by a polynucleotide with at least 90% sequence identity to the polynucleotide of SEQ ID NO: 3, SEQ ID NO: 21, or SEQ ID NO: 22. In some aspects, a variant PapG protein is encoded by a polynucleotide with at least 95% sequence identity to the polynucleotide of SEQ ID NO: 3, SEQ ID NO: 21, or SEQ ID NO: 22. In some aspects, a variant PapG protein is encoded by a polynucleotide with at least 99% sequence identity to the polynucleotide of SEQ ID NO: 3, SEQ ID NO: 21, or SEQ ID NO: 22.

In some embodiments, the PapG protein comprises, consists essentially of, or consists of the PapG protein provided in SEQ ID NO: 4 (GenBank Accession No. X61237; GI: 42307), SEQ ID NO: 23 (GenBank Accession No. AY212280.1; GI: 37786764), or SEQ ID NO: 24 (GenBank Accession No. AY212279.1; GI: 37786762). In some embodiments, the PapG protein comprises, consists essentially of, or consists of a variant of SEQ ID NO: 4, SEQ ID NO: 23, or SEQ ID NO: 24. In some embodiments, the PapG protein comprises, consists essentially of, or consists of a portion of SEQ ID NO: 4, SEQ ID NO: 23, or SEQ ID NO: 24; or a portion of a variant of SEQ ID NO: 4, SEQ ID NO: 23, or SEQ ID NO: 24.

In some embodiments, a variant PapG protein is a protein having at least 80% sequence identity to SEQ ID NO: 4, SEQ ID NO: 23, or SEQ ID NO: 24. In some aspects, a variant PapG protein is a protein having at least 90% sequence identity to SEQ ID NO: 4, SEQ ID NO: 23, or SEQ ID NO: 24. In some aspects, a variant PapG protein is a protein having at least 95% sequence identity to SEQ ID NO: 4, SEQ ID NO: 23, or SEQ ID NO: 24. In some aspects, a variant PapG protein is a protein having at least 99% sequence identity to SEQ ID NO: 4, SEQ ID NO: 23, or SEQ ID NO: 24.

A skilled artisan can select an appropriate PapG protein, or variant thereof, based on, for example, the sequence of the PapG protein in an *E. coli* species for which protection against infection is useful. Similarly, a skilled artisan can select a portion of a PapG protein based on, for example, the function of the portion (e.g., the function of a protein domain) and the immunogenicity of the portion (i.e., its ability to stimulate an immune response). In some embodiments, a portion of the PapG protein comprises, consists essentially of, or consists of at least 20, 40, 60, 80, or 100 contiguous amino acid residues from SEQ ID NO: 4, SEQ ID NO: 23, or SEQ ID NO: 24.

2.2. FimH

As described above, a vaccine provided herein can induce an immune response against any suitable FimH protein. In some embodiments, the FimH protein is a FimH protein expressed by a pathogenic *E. coli*. In some embodiments, the pathogenic *E. coli* is an APEC.

In some embodiments, the FimH protein used to vaccinate the subject comprises, consists essentially of, or consists of a FimH protein encoded by nucleotides 1340-2242 of SEQ ID NO: 1 (GenBank Accession No. AJ225176; GI: 3286745). In some embodiments, the FimH protein used to vaccinate the subject comprises, consists essentially of, or consists of a FimH protein encoded by a variant of nucleotides 1340-2242 of SEQ ID NO: 1. In some embodiments, the FimH protein used to vaccinate the subject comprises, consists essentially of, or consists of a portion of a FimH protein encoded by a portion of nucleotides 1340-2242 of SEQ ID NO: 1, or a portion of a FimH protein encoded by a variant of a portion of nucleotides 1340-2242 of SEQ ID NO: 1.

In some embodiments, a variant FimH protein is encoded by a polynucleotide with at least 80% sequence identity to nucleotides 1340-2242 of SEQ ID NO: 1. In some aspects, a variant FimH protein is encoded by a polynucleotide with at least 90% sequence identity to nucleotides 1340-2242 of SEQ ID NO: 1. In some aspects, a variant FimH protein is encoded by a polynucleotide with at least 95% sequence identity to nucleotides 1340-2242 of SEQ ID NO: 1. In some aspects, a variant FimH protein is encoded by a polynucleotide with at least 99% sequence identity to nucleotides 1340-2242 of SEQ ID NO: 1.

In some embodiments, the FimH protein comprises, consists essentially of, or consists of the FimH protein provided in SEQ ID NO: 2 (GenBank Accession No. AJ225176; GI: 3286745) or SEQ ID NO: 25 (GenBank Accession No. AGA03820.1; GI: 429545215). In some embodiments, the FimH protein comprises, consists essentially of, or consists of a variant of SEQ ID NO: 2 or SEQ ID NO: 25. In some embodiments, the FimH protein comprises, consists essentially of, or consists of a portion of SEQ ID NO: 2 or SEQ ID NO: 25; or a portion of a variant of SEQ ID NO: 2 or SEQ ID NO: 25.

In some embodiments, a variant FimH protein comprises, consists essentially of, or consists of a protein having at least 80% sequence identity to the corresponding region of SEQ ID NO: 2 or SEQ ID NO: 25. In some aspects, a variant FimH protein comprises, consists essentially of, or consists of a protein having at least 90% sequence identity to the corresponding region of SEQ ID NO: 2 or SEQ ID NO: 25. In some aspects, a variant FimH protein comprises, consists essentially of, or consists of a protein having at least 95% sequence identity to the corresponding region of SEQ ID NO: 2 or SEQ ID NO: 25. In some aspects, a variant FimH protein comprises, consists essentially of, or consists of a protein having at least 99% sequence identity to the corresponding region of SEQ ID NO: 2 or SEQ ID NO: 25.

In some embodiments, a variant FimH protein is a protein having at least 80% sequence identity to SEQ ID NO: 2 or SEQ ID NO: 25. In some aspects, a variant FimH protein is a protein having at least 90% sequence identity to SEQ ID NO: 2 or SEQ ID NO: 25. In some aspects, a variant FimH protein is a protein having at least 95% sequence identity to SEQ ID NO: 2 or SEQ ID NO: 25. In some aspects, a variant FimH protein is a protein having at least 99% sequence identity to SEQ ID NO: 2 or SEQ ID NO: 25.

A skilled artisan can select an appropriate FimH protein, or variant thereof, based on, for example, the sequence of the FimH protein in an *E. coli* species for which protection against infection is useful. Similarly, a skilled artisan can select a portion of a FimH protein based on, for example, the function of the portion (e.g., the function of a protein domain) and the immunogenicity of the portion (i.e., its ability to stimulate an immune response). In some embodiments, a portion of the FimH protein comprises, consists essentially of, or consists of at least 20, 40, 60, 80, or 100 contiguous amino acid residues from SEQ ID NO: 2 or SEQ ID NO: 25.

2.3. IutA

As described above, a vaccine provided herein can induce an immune response against any suitable IutA protein. In some embodiments, the IutA protein is an IutA protein expressed by a pathogenic *E. coli*. In some embodiments, the pathogenic *E. coli* is an APEC.

In some embodiments, the IutA protein used to vaccinate the subject comprises, consists essentially of, or consists of an IutA protein encoded by nucleotides 304 to 2364 of SEQ ID NO: 5 (GenBank Accession No. X05874; GI: 41261). In some embodiments, the IutA protein used to vaccinate the subject comprises, consists essentially of, or consists of an IutA protein encoded by a variant of nucleotides 304 to 2364 of SEQ ID NO: 5. In some embodiments, the IutA protein used to vaccinate the subject comprises, consists essentially of, or consists of a portion of an IutA protein encoded by a portion of nucleotides 304 to 2364 of SEQ ID NO: 5, or a portion of an IutA protein encoded by a variant of a portion of nucleotides 304 to 2364 of SEQ ID NO: 5.

In some embodiments, a variant IutA protein is encoded by a polynucleotide with at least 80% sequence identity to nucleotides 304 to 2364 of SEQ ID NO: 5. In some aspects, a variant IutA protein is encoded by a polynucleotide with at least 90% sequence identity to nucleotides 304 to 2364 of SEQ ID NO: 5. In some aspects, a variant IutA protein is encoded by a polynucleotide with at least 95% sequence identity to nucleotides 304 to 2364 of SEQ ID NO: 5. In some aspects, a variant IutA protein is encoded by a polynucleotide with at least 99% sequence identity to nucleotides 304 to 2364 of SEQ ID NO: 5.

In some embodiments, the IutA protein comprises, consists essentially of, or consists of the IutA protein provided in SEQ ID NO: 6 (IutA Amino Acid Sequence) or SEQ ID NO: 26 (GenBank Accession No. YP 001481324.1; GI: 157418252). In some embodiments, the IutA protein comprises, consists essentially of, or consists of a variant of SEQ ID NO: 6 or SEQ ID NO: 26. In some embodiments, the IutA protein comprises, consists essentially of, or consists of a portion of SEQ ID NO: 6 or SEQ ID NO: 26; or a portion of a variant of SEQ ID NO: 6 or SEQ ID NO: 26.

In some embodiments, a variant IutA protein is a protein having at least 80% sequence identity to SEQ ID NO: 6 or SEQ ID NO: 26. In some aspects, a variant IutA protein is a protein having at least 90% sequence identity to SEQ ID NO: 6 or SEQ ID NO: 26. In some aspects, a variant IutA protein is a protein having at least 95% sequence identity to SEQ ID NO: 6 or SEQ ID NO: 26. In some aspects, a variant IutA protein is a protein having at least 99% sequence identity to SEQ ID NO: 6 or SEQ ID NO: 26.

A skilled artisan can select an appropriate IutA protein, or variant thereof, based on, for example, the sequence of the IutA protein in an *E. coli* species for which protection against infection is useful. Similarly, a skilled artisan can select a portion of an IutA protein based on, for example, the function of the portion (e.g., the function of a protein domain) and the immunogenicity of the portion (i.e., its ability to stimulate an immune response). In some embodiments, a portion of the IutA protein comprises, consists essentially of, or consists of at least 20, 40, 60, 80, or 100 contiguous amino acid residues from SEQ ID NO: 6 or SEQ ID NO: 26.

3. Protein and Nucleic Acid Forms of the Immunogens

In some embodiments, a vaccine provided herein is a protein-based vaccine comprising, consisting essentially of, or consisting of one or more protein immunogens, portions thereof, or variants thereof as described elsewhere in this disclosure.

In some embodiments, a vaccine provided herein is a nucleic acid-based vaccine comprising, consisting essentially of, or consisting of one or more nucleic acids encoding the one or more protein immunogens, portions thereof, or variants thereof described elsewhere in this disclosure. These nucleic acids may transfect cells in situ, leading to the in situ production of protein immunogens that then induce an immune response. See e.g., Drabick et al., *Mol. Ther.,* 2001, 3:249-255, incorporated by reference in its entirety. Suitable nucleic acids include, for example, plasmids, linear DNA, and RNA.

In some embodiments, a vaccine may comprise, consist essentially of, or consist of both protein immunogens and nucleic acid immunogens.

4. Fusions

In some embodiments, a vaccine provided herein comprises an immunogen fused to another protein (a fusion partner) that increases the immune response to the immunogen. If the vaccine comprises a nucleic acid, then the nucleic acid may encode the immunogen fused to the fusion partner. Any suitable fusion partner can be used.

In some embodiments, the fusion partner is a leukotoxin. Any suitable leukotoxin may be used. In some embodiments, the leukotoxin is a leukotoxin *A. Leukotoxin* A is a part of the family of toxins called RTX (repeats-in-toxin) that have a similar repetitive amino acid sequence (e.g., LXGGXGNDX; SEQ ID NO: 19) that is linked to leukocytic activity.

Any suitable leukotoxin A may be used. Suitable leukotoxin As include, for example, leukotoxin As from *Pasteurella* sp., such as *P. haemolytica; Aggregatibacter* sp., such as *A. actinomycetemcomitans; Fusobacterium* sp., such as *F. necrophorum*; and *Mannheimia* sp., such as *M. glucosidal, M. ruminalis*, and *M. haemolytica*. In some embodiments, the leukotoxin A is a leukotoxin A from *Pasteurella haemolytica* (SEQ ID NO: 20).

Variants of leukotoxin As may also be used. Suitable variants include variants having at least 80%, 85%, 90%, 95%, or 99% sequence identity with a leukotoxin A protein. In some embodiments, a variant has at least 80%, 85%, 90%, 95%, or 99% sequence identity with the *Pasteurella haemolytica* leukotoxin A protein of SEQ ID NO: 20.

Portions of leukotoxin As may also be used. Suitable portions of leukotoxin A include portions having at least 10, 20, 30, or 100 contiguous amino acids from a leukotoxin protein. In some embodiments, a portion of a leukotoxin A has at least 10, 20, 30, or 100 contiguous amino acids from the *Pasteurella haemolytica* leukotoxin A protein of SEQ ID NO: 20. In some embodiments, a portion of a leukotoxin A has at least 10, 20, 30, or 100 contiguous amino acids from a variant of the *Pasteurella haemolytica* leukotoxin A protein of SEQ ID NO: 20.

The fusion partner may be attached to the immunogen at any suitable site. In some embodiments, the fusion partner is attached to the C-terminus of the immunogen. In some embodiments, the fusion partner is attached to the N-terminus of the immunogen. In some embodiments, the fusion partner is attached to both the C-terminus and the N-terminus of the immunogen.

Also included within the scope of the invention are embodiments where leukotoxin is chemically conjugated to an immunogen. Chemical conjugation may be performed by attaching leukotoxin to any of the amino acid residues located along the immunogen, or vice versa.

5. Pharmaceutical Compositions

In some embodiments, a vaccine provided herein is in the form of a pharmaceutical composition. The term “pharmaceutical composition” refers to a composition suitable for administration to a subject.

In some embodiments, the pharmaceutical composition comprises one or more adjuvants. Adjuvants are agents that modulate the immunological response to a vaccine to induce a more significant immune response than would be achieved in the absence of the adjuvant.

Any suitable adjuvant may be used in the vaccines provided herein, and one of ordinary skill in the art is capable of selecting suitable adjuvants. Suitable adjuvants include, for example, chitosan (e.g., methylated, trimethylated, or derivatives thereof), oil emulsions, toxins produced by bacteria, aluminum salts (e.g., aluminum hydroxide, aluminum phosphate), alum, mineral oil (e.g., paraffin oil), squalane, thimerosal, interleukin-1, interleukin-2, interleukin-12, Freund’s complete adjuvant, Freund’s incomplete adjuvant, nucleic acids (e.g., CpG), and polymers (e.g., polysaccharides, polyelectrolytes, polyesters, polyanhydrides, non-ionic block copolymers). In some embodiments, the adjuvant is chitosan. In some embodiments, the adjuvant is chitosan and the pharmaceutical composition further comprises tripolyphosphate (TPP).

The pharmaceutical compositions provided herein may also comprise one or more pharmaceutical excipients. Any suitable pharmaceutical excipient may be used, and one of ordinary skill in the art is capable of selecting suitable pharmaceutical excipients. Accordingly, the pharmaceutical excipients provided below are intended to be illustrative, and not limiting. Additional pharmaceutical excipients include, for example, those described in the *Handbook of Pharmaceutical Excipients*, Rowe et al. (Eds.) 6th Ed. (2009), The Pharmaceutical Press, incorporated by reference in its entirety.

In some embodiments, the pharmaceutical composition comprises a solvent. In some aspects, the solvent is saline solution, such as a sterile isotonic saline solution or dextrose solution. In some aspects, the solvent is water for injection.

In some embodiments, the pharmaceutical composition comprises an anti-foaming agent. Any suitable anti-foaming agent may be used. In some aspects, the anti-foaming agent is selected from an alcohol, an ether, an oil, a wax, a silicone, a surfactant, and combinations thereof. In some aspects, the anti-foaming agent is selected from a mineral oil, a vegetable oil, ethylene bis stearamide, a paraffin wax, an ester wax, a fatty alcohol wax, a long chain fatty alcohol, a fatty acid soap, a fatty acid ester, a silicon glycol, a fluorosilicone, a polyethylene glycol-polypropylene glycol copolymer, polydimethylsiloxane-silicon dioxide, ether, octyl alcohol, capryl alcohol, sorbitan trioleate, ethyl alcohol, 2-ethylhexanol, dimethicone, oleyl alcohol, simethicone, and combinations thereof.

In some embodiments, the pharmaceutical composition comprises a cosolvent. Illustrative examples of cosolvents include ethanol, poly(ethylene) glycol, butylene glycol, dimethylacetamide, glycerin, and propylene glycol.

In some embodiments, the pharmaceutical composition comprises a buffer. Illustrative examples of buffers include acetate, borate, carbonate, lactate, malate, phosphate, citrate, hydroxide, diethanolamine, monoethanolamine, glycine, methionine, guar gum, and monosodium glutamate.

In some embodiments, the pharmaceutical composition comprises a carrier or filler. Illustrative examples of carriers or fillers include lactose, maltodextrin, mannitol, sorbitol, chitosan, stearic acid, xanthan gum, and guar gum.

In some embodiments, the pharmaceutical composition comprises a surfactant. Illustrative examples of surfactants include d-alpha tocopherol, benzalkonium chloride, benzethonium chloride, cetrimide, cetylpyridinium chloride, docusate sodium, glyceryl behenate, glyceryl monooleate, lauric acid, macrogol 15 hydroxystearate, myristyl alcohol, phospholipids, polyoxyethylene alkyl ethers, polyoxyethylene sorbitan fatty acid esters, polyoxyethylene stearates, polyoxylglycerides, sodium lauryl sulfate, sorbitan esters, and vitamin E polyethylene(glycol) succinate.

In some embodiments, the pharmaceutical composition comprises an anti-caking agent. Illustrative examples of anti-caking agents include calcium phosphate (tribasic), hydroxymethyl cellulose, hydroxypropyl cellulose, and magnesium oxide.

In some embodiments, the pharmaceutical composition comprises a propellant. Illustrative examples of propellants include carbon dioxide, chlorodifluoromethane, chlorofluorocarbons, difluoroethane, dimethyl ether, heptafluoropropane, hydrocarbons (e.g., butane, isobutene, propane), nitrogen, nitrous oxide, and tetrafluoroethane.

Other excipients that may be used with the pharmaceutical compositions include, for example, albumin, antioxidants, antibacterial agents, antifungal agents, bioabsorbable polymers, chelating agents, controlled release agents, diluents, dispersing agents, dissolution enhancers, emulsifying agents, gelling agents, ointment bases, penetration enhancers, preservatives, solubilizing agents, solvents, stabilizing agents, and sugars. Specific examples of each of these agents are described, for example, in the *Handbook of Pharmaceutical Excipients*, Rowe et al. (Eds.) 6th Ed. (2009), The Pharmaceutical Press, incorporated by reference in its entirety.

In some embodiments, the pharmaceutical compositions are in a particulate form, such as a microparticle or a nanoparticle. Microparticles and nanoparticles may be formed from any suitable material, such as a polymer or a lipid. In some aspects, the microparticles or nanoparticles are micelles, liposomes, or polymersomes. In some aspects, the particles are chitosan particles.

6. Routes of Administration

The vaccines provided herein may be administered by any suitable routes of administration. The route of administration can be local or systemic. Illustrative routes of administration include, for example, the intranasal, intramuscular, pulmonary, inhalation, intraarterial, intradermal, intralesional, intraperitoneal, intravenous, intrathecal, intravesical, parenteral, rectal, subcutaneous, topical, transdermal, transmucosal, in ovo, and vaginal routes. In some embodiments, the vaccine is administered by the intranasal route of administration. In some embodiments, the vaccine is administered by the intramuscular route of administration.

7. Dosing, Dosage Forms and Dosing Schedules

A skilled doctor or veterinarian can determine the posology considered appropriate for administration of the vaccines provided herein, according to, for example, the age, weight, infectious agent, and other factors specific to the subject to be vaccinated.

In some embodiments, a dose of about 1 μg to about 1 mg of protein or nucleic acid is administered to a subject in need of vaccination. In some aspects, the dose is about 1 μg to about 750 μg. In some aspects, the dose is about 1 μg to about 500 μg. In some aspects, the dose is about 1 μg to about 250 μg. In some aspects, the dose is about 1 μg to about 100 μg. In some aspects, the dose is about 1 μg to about 50 μg. In some aspects, the dose is about 10 μg to about 50 μg. In some aspects, the dose is about 20 μg.

Based on the dose required for a particular subject, a vaccine provided herein can be formulated as a unit dosage form comprising a particular dose of protein or nucleic acid. For example, in some embodiments a unit dosage form comprises about 1 μg to about 1 mg of protein or nucleic acid. In some aspects, the unit dosage form comprises about 1 μg to about 750 μg of protein or nucleic acid. In some aspects, the unit dosage form comprises about 1 μg to about 500 μg of protein or nucleic acid. In some aspects, the unit dosage form comprises about 1 μg to about 250 μg of protein or nucleic acid. In some aspects, the unit dosage form comprises about 1 μg to about 100 μg of protein or nucleic acid. In some aspects, the unit dosage form comprises about 1 μg to about 50 μg of protein or nucleic acid. In some aspects, the unit dosage form comprises about 10 μg to about 50 μg of protein or nucleic acid. In some aspects, the unit dosage form comprises about 20 μg of protein or nucleic acid.

The vaccine may be administered to a subject according to any suitable dosing schedule. In some embodiments, the vaccine is administered once. In some embodiments, the vaccine is administered more than once. In some aspects, the vaccine is administered 2, 3, 4, 5, or 6 times.

In some embodiments, the vaccine is administered according to a particular frequency. In some embodiments, the frequency is daily, every 2 days, every 3 days, every 4 days, every 5 days, every 6 days, every 7 days, every 8 days, every 9 days, every 10 days, every 11 days, every 12 days, every 13 days, or every 14 days. In some embodiments, the frequency is every 3 weeks, every 4 weeks, every 5 weeks, every 6 weeks, every 7 weeks, every 8 weeks, every 9 weeks, every 10 weeks, every 11 weeks, or every 12 weeks. In some embodiments, the frequency is every 1 month, every 2 months, every 3 months, every 4 months, every 5 months, every 6 months, every 7 months, every 8 months, every 9 months, every 10 months, every 11 months, every 12 months, every 13 months, every 14 months, every 15 months, every 16 months, every 17 months, or every 18 months. In some embodiments, the frequency is every 2 years, every 3 years, every 4 years, or every 5 years. In some embodiments, a single dose of the vaccine is administered after the first dose, after an interval described above.

In some embodiments, the vaccine is administered once, followed by a single booster administration 7, 14, 28, 35, 42, 49, or 56 days later. In some embodiments, the booster administration is 28 days after the first administration.

8. Methods of Vaccinating

Also provided herein are methods of vaccinating against a pathogenic *E. coli* by administering a vaccine provided herein to a subject in need thereof. In some embodiments, the pathogenic *E. coli* is an APEC.

In some embodiments, the vaccination prevents infection by the pathogenic *E. coli*. In some embodiments, the vaccination enables the subject's immune system to successfully control or eradicate infection by the pathogenic *E. coli*.

In some embodiments, the vaccine is administered more than once before the subject becomes immunized against the pathogenic *E. coli*. In some embodiments, a second dose of the vaccine is administered at least 5, 7, 10 14, 21, 28, or 35 days after administration of a first dose of the vaccine. In some embodiments, a second dose of the vaccine is administered at least 6, 7, 8, 9, 10, 11, or 12 weeks after administration of a first dose of the vaccine.

More specifically, provided herein are methods of preventing infection of a subject with a pathogenic *E. coli*, comprising administering an effective amount of a vaccine provided herein to the subject.

Also provided are methods of enabling a subject to control an infection by pathogenic *E. coli*, comprising administering an effective amount of a vaccine provided herein to the subject.

Also provided are methods of enabling a subject to eliminate an infection by pathogenic *E. coli*, comprising administering an effective amount of a vaccine provided herein to the subject.

In some embodiments, the subject is selected from an avian and a mammal. In some embodiments the avian is selected from a chicken and a turkey. In some embodiments, the mammal is selected from a cow, a pig, a horse, a sheep, a camel, a dog, a cat, and a human. In some embodiments, the subject is a chicken.

In some embodiments, the pathogenic *E. coli* causes a disease selected from colibacillosis, urinary tract infection, gastrointestinal infections, skin infections, respiratory infections, neonatal meningitis, inflammation, septicemia, metritis, mastitis, perihepatitis, pericarditis, and peritonitis.

In some embodiments, administration of a vaccine provided herein to the subject induces a mucosal antibody response. In some aspects, the mucosal antibody response comprises the induction of secretory IgA antibody activity in the intestine. In some aspects, the mucosal antibody response comprises the induction of IgA antibody activity in the respiratory tract. In some embodiments, the antibody response further comprises a serum antibody response.

9. Polynucleotides, Proteins, and Host Cells

Also provided are polynucleotides encoding an immunogen described herein and leukotoxin A. In some aspects, a polynucleotide encodes PapG and a leukotoxin A. In some aspects, a polynucleotide encodes FimH and a leukotoxin A. In some aspects, a polynucleotide encodes IutA and a leukotoxin A.

In some embodiments, the immunogens and the leukotoxin A are expressed as a fusion protein. In some embodiments, the leukotoxin A is fused to the N-terminal portion of the immunogen. In some embodiments, the leukotoxin A is fused to the C-terminal portion of the immunogen.

In some embodiments, a linker is used to attach the immunogen to the leukotoxin A. In some embodiments, the linker comprises glycine and serine.

Also provided are fusion proteins expressed from the polynucleotides. The fusion proteins can be expressed using methods known to those of ordinary skill in the art, as further described in the examples provided herein.

Also provided are cells comprising the polynucleotides. The cells can be used to express the fusion proteins described herein. A person of ordinary skill in the art is capable of picking an appropriate cell type based on, for example, the fusion protein to be expressed, and the desired yield.

10. Kits

Also provided herein are kits for use with the compositions and methods provided herein. In some embodiments, the kit comprises a vaccine provided in this disclosure and instructions for administration of the vaccine.

In some embodiments, the vaccine is provided in a lyophilized form. In some embodiments, the kit further comprises a solvent for reconstitution of the vaccine prior to administration to a subject. In some embodiments, the kit further comprises instructions for administration of the vaccine to the subject.

In some embodiments, the kit further comprises a device for delivery of the vaccine. In some embodiments, the device is a device for intramuscular delivery or intranasal delivery. In some aspects, the device is selected from a needle and device that delivers droplets intranasally.

In some embodiments, the kit further comprises packaging. In some aspects, this packaging includes a container suitable for holding a vaccine. The container can be made of any suitable material. Suitable materials include, for example, glass, plastic paper, laminates, and the like.

EXAMPLES

Example 1

Cloning and Expression of Avian Pathogenic *E. coli* Genes Fused to Leukotoxin A genomic DNA preparation from a frozen stock of *E. coli* EC317 was completed and used for PCR of the three *E. coli* genes identified by GenBank accession numbers AJ225176 (GI: 3286745), X61237 (GI: 42307), and X05874 (GI: 41261).

GenBank accession number AJ225176 (GI: 3286745) provides the polynucleotide sequence of a cluster of *E. coli* genes that encode fimD, fimF, fimG, fimH, uxaA & gntP genes (SEQ ID NO: 1). The type 1 fimbriae adhesion (FimH) precursor polypeptide is encoded by nucleotides 1340-2242 of SEQ ID NO: 1, and has the amino acid sequence provided in SEQ ID NO: 2.

GenBank accession number X61237 (GI: 42307) provides the polynucleotide sequence of the *E. coli* papG gene (SEQ ID NO: 3).The polypeptide product of this gene (i.e., the PapG protein) has the amino acid sequence provided in SEQ ID NO: 4.

GenBank accession number X05874 (GI: 41261) provides the polynucleotide sequence of the *E. coli* plasmid pFS8 cloacin DF13/aerobactin receptor gene (iutA) (SEQ ID NO: 5). The polypeptide product IutA has the amino acid sequence provided in SEQ ID NO: 6.

Briefly, the bacteria were grown from frozen stock by inoculating a loopful of frozen stock into Brain Heart Infusion broth overnight. A loopful of the overnight growth was streaked on LB medium and grown at 37° C. One pure colony was streaked subsequently to obtain a pure plate of EC317. Genomic DNA was extracted using a Qiagen genomic DNA miniprep kit (Qiagen, Mississauga, ON). DNA concentration was measured using spectrophotometry.

To amplify the targeted genes, PCR primers were designed based on the GenBank sequences (Table 1). The primers were also designed to enable fusion of the amplified PCR products to the *Pasteurella haemolytica* leukotoxin gene within the pAA352 construct. Leukotoxin is highly immunogenic and the construct used in this study is highly stable and yields high amounts of protein.

TABLE 1

Sequences of the primers used to amplify the genes fimH, iutA, and papG. To amplify the targeted genes, PCR primers were designed based on the GenBank sequences. The primers were also designed to enable fusion of the amplified PCR products to the *Pasteurella haemolytica* leukotoxin gene within the pAA352 construct. Leukotoxin is highly immunogenic and the construct used in this study is highly stable and yields high amounts of protein. Primers were synthesized by Invitrogen Life Technologies.

| Primer | Sequence |
|---|---|
| AJ225176 (fimH F) | 5'-GCGTCCGGATCCAAACGAGTTATTACCCTGTTTG-3' (SEQ ID NO: 7) |
| AJ2251766 (fimH R) | 5'GCGCCGCGCCATGGTTATTGATAAACAAAAGTCACGC-3' (SEQ ID NO: 8) |
| X05874 (iutA F) | 5'CGCGGCGGATCCATAAGCAAAAAGTATACGCTTTGG-3' (SEQ ID NO: 9) |
| X05874 (iutA R) | 5'TCTGGACCATGGTCAGAACAGCACAGAGTAGTTC-3' (SEQ ID NO: 10) |
| X61237 (papG F) | 5'GCGCAGGGATCCAAAAAATGGTTCCCAGCTTTG-3' |
| X61237 (papG R) | 5'GCGCAGGCTAGCTTATGGCAATATCATGAGCAG-3' (SEQ ID NO: 11) |

To amplify the targeted genes, PCR reactions were prepared using PCR master mix from Fermentas (cat #K0171) using a final concentration of 20 μM for each primer and 100 ng of genomic DNA. The reactions were carried out on an MJ Research PTC-100 thermal cycler under the following conditions: 94° C. 5 minutes; 29 cycles of: 94° C. for 50 seconds, 55° C. for 40 seconds, and 72° C. for 2 minutes 30 seconds; 72° C. for 5 minutes.

To visualize the amplification products, PCR reactions were run on a 1% agarose gel. The amplified products were cut out and purified from the gel using a Qiagen QIAquick Gel Extraction Kit (cat #28704). Briefly, cut-out gels were dissolved in 3× the weight of QG buffer. The tube was then incubated at 50° C. for 10 minutes. After vortexing, a 1 × volume of isopropanol was added and the tube was centrifuged. The supernatant was applied to a spin column and centrifuged. The column was washed and the eluent collected. DNA was quantified using a Nanodrop machine (Thermo Fisher).

The purified AJ225176, X61237 and X05874 PCR products were digested with BamHI/NcoI restriction endonucleases (New England Biolabs) for one hour at 37° C. The same enzymes were used to digest the pAA352 vector plasmid. The vector was dephosphorylated using Antarctic phosphatase (NEB) and all digests were run on a 1% agarose gel and purified from the gel as described previously. One microliter of each purified and digested DNA was run on a 1% agarose gel to evaluate the recovered quantity. DNA ligations were set up with T4 DNA Ligase (NEB) and incubated at 16° C. overnight.

The ligated DNA was transformed into chemically competent *E.coli* DH5cdQ cells. Briefly, frozen competent cells were thawed on ice, flicked, and 25 μg of DNA were added to the competent cells. After 10 minutes of incubation on ice, cells were transferred to a 42° C. water bath for 50 seconds. Cells were placed back on ice for 2 minutes. SOC media was added and the tube was flicked. The cells were plated on Luria Bertani (LB) agar medium containing 100 μg/ml ampicillin and the plates incubated at 37° C. overnight.

Colonies were chosen, grown in 5 ml of LB broth+50 μg/ml ampicillin and plasmids isolated using alkaline lysis. Plasmid DNA was digested with BamHI/NcoI restriction endonucleases to confirm presence of an insert. All tested colonies were positive for an insert. Five milliliters of cultures of positive transformants were grown to an optical density 600 nm of 0.6 then induced for 2 hours with 1 mM (final) IPTG. The cells were pelleted, suspended in sample buffer and run on 11% SDS-PAGE gels to look for an induced protein product. Induced protein was detected for all three constructs.

Figure 2:
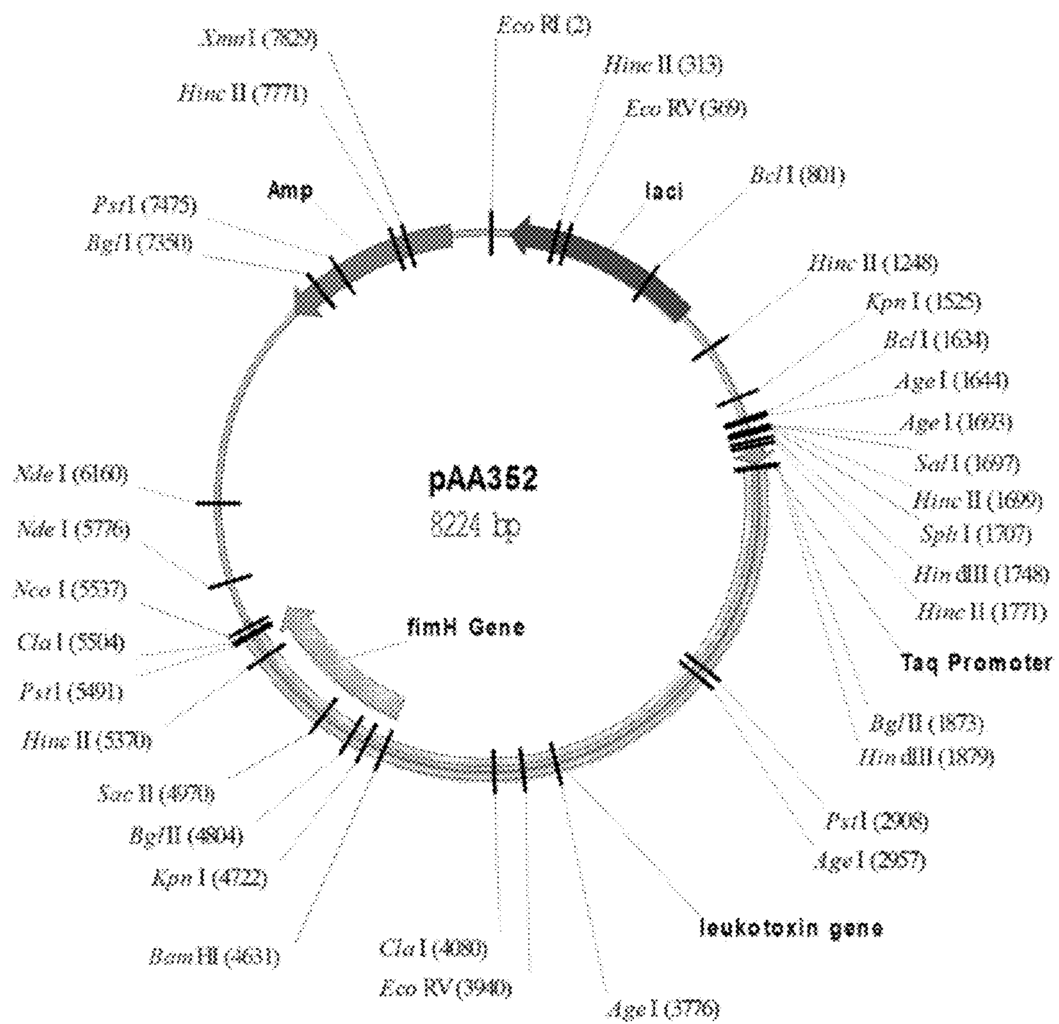
FIG. 2 provides a map of plasmid pAA352 with the inserted adhesion of type I fimbriae (fimH) gene. The plasmid has a *Pasteurella haemolytica* leukotoxin gene fused to fimH so that they can be expressed as a fusion protein. The plasmid also contains an inducible promoter and ampicillin resistance gene.
Figure 3:
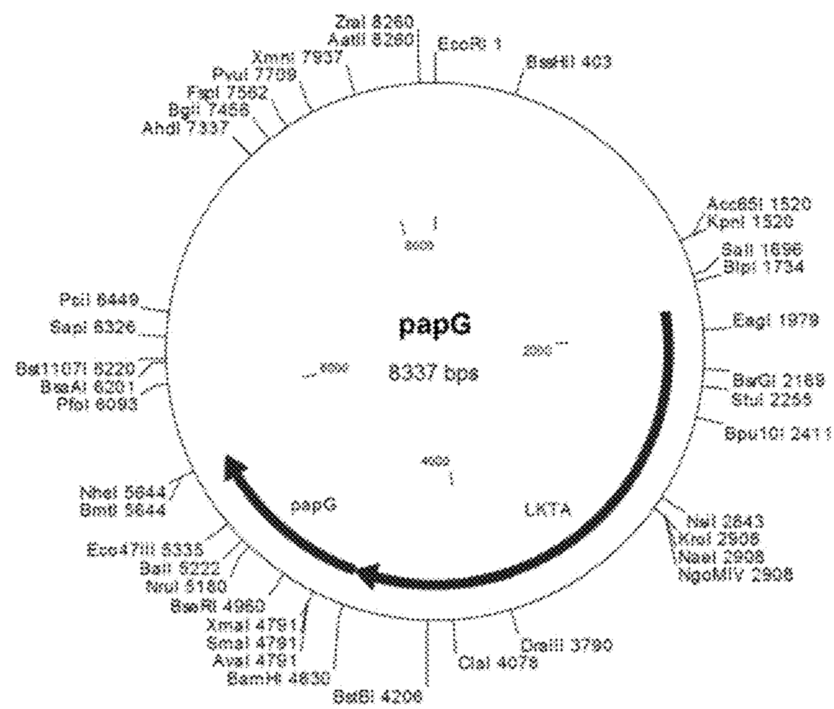
FIG. 3 provides a map of plasmid pAA352 with the inserted papG gene. The plasmid has a *Pasteurella haemolytica* leukotoxin gene fused to fimH so that they can be expressed as a fusion protein. The plasmid also contains an inducible promoter and ampicillin resistance gene.

FIG. 1 provides a map of plasmid pAA352 with the inserted aerobactin receptor gene (iutA). FIG. 2 provides a map of plasmid pAA352 with the inserted adhesion of type I fimbriae (fimH) gene. FIG. 3 provides a map of plasmid pAA352 with the inserted papG gene. The plasmids have a *Pasteurella haemolytica* leukotoxin gene fused to iutA, fimH, or papG, respectively, so that they can be expressed as a fusion protein. The plasmids also contain an inducible promoter and ampicillin resistance gene.

Figure 4:
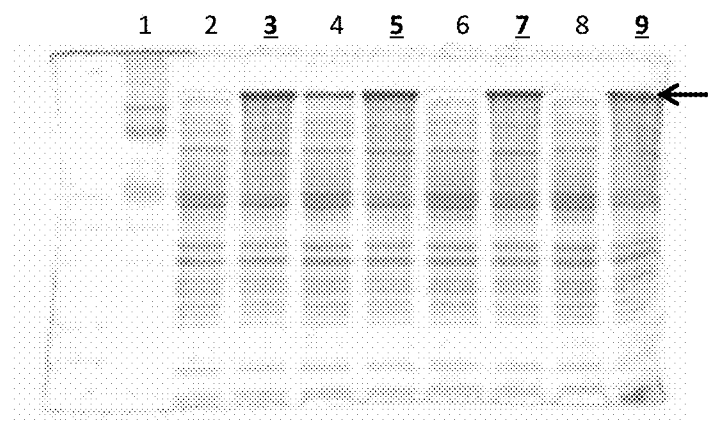
FIG. 4 provides a sodium dodecyl sulfate-polyacrylamide gel electrophoresis (SDS-PAGE) gel showing overexpression of FimH protein fused to the *Pasteurella haemolytica* leukotoxin gene, as indicated by the arrow. Induced protein can be seen at the top of lanes 3, 5, 7, and 9.

FIG. 4 provides a sodium dodecyl sulfate-polyacrylamide gel electrophoresis (SDS-PAGE) gel showing overexpression of FimH protein fused to the *Pasteurella haemolytica* leukotoxin gene, as indicated by the arrow. Induced protein can be seen at the top of lanes 3, 5, 7, and 9.

Figure 5:
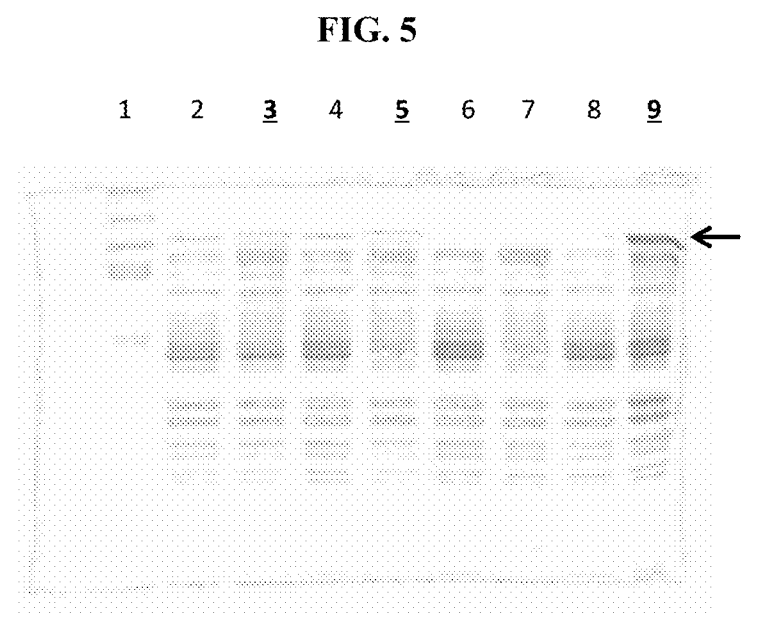

FIG. 5 provides an SDS-PAGE gel showing overexpression of IutA protein fused to the *Pasteurella haemolytica* leukotoxin gene, as indicated by the arrow. Induced protein can be seen at the top of lanes 3, 5, and 9.

Figure 6:
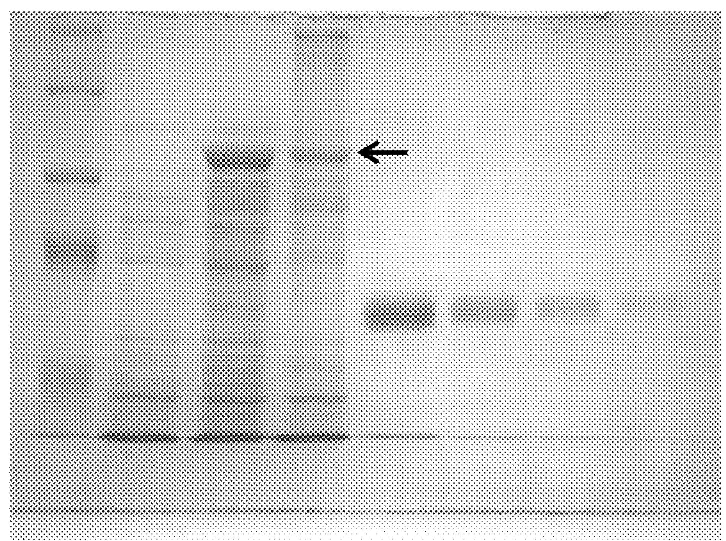
FIG. 6 provides an SDS-PAGE gel showing overexpression of PapG protein fused to the *Pasteurella haemolytica* leukotoxin gene, as indicated by the arrow. Induced protein can be seen in lanes 2 and 3, which contain whole cell lysate from induced cells and aggregates isolated from induced cells, respectively. Lane 1 contains non-induced cells, and lanes 4-7 contain different amounts of a bovine serum albumin (BSA) standard.

FIG. 6 provides an SDS-PAGE gel showing overexpression of PapG protein fused to the *Pasteurella haemolytica* leukotoxin gene, as indicated by the arrow. Induced protein can be seen in lanes 2 and 3, which contain whole cell lysate from induced cells and aggregates isolated from induced cells, respectively. Lane 1 contains non-induced cells, and lanes 4-7 contain different amounts of a bovine serum albumin (BSA) standard.

High quality plasmid DNA from transformants expressing recombinant protein was prepared for DNA sequencing and sequenced using the sequencing primers provided in Table 2 (synthesized by Life Technologies). The sequencing analysis confirmed the insertions of the genes into the vector.

The sequence of the polynucleotide encoding the leukotoxin A-FimH fusion is provided in SEQ ID NO: 27. In this sequence, the polynucleotide sequence from 1858 to 4635 encodes leukotoxin A, and the polynucleotide sequence from 4636 to 5535 encodes FimH.

The sequence of the polynucleotide encoding the leukotoxin A-PapG fusion is provided in SEQ ID NO: 28. In this sequence, the polynucleotide sequence from 1858 to 4635 encodes leukotoxin A, and the polynucleotide sequence from 4636 to 5634 encodes PapG.

The sequence of the polynucleotide encoding the leukotoxin A-IutA fusion is provided in SEQ ID NO: 29. In this sequence, the polynucleotide sequence from 1858 to 4635 encodes leukotoxin A, and the polynucleotide sequence from 4636 to 6828 encodes leukotoxin.

TABLE 2

Primers designed for sequencing of purified constructed plasmids. High quality plasmid DNA was prepared for DNA sequencing.

| Primer | Sequence |
|---|---|
| AJ225176 (fimHseqF1) | 5'-TTCCCTACTACCAGCGAAAC-3' (SEQ ID NO: 12) |
| AJ225176 (fimHseqF2) | 5'-GTACAGTTGACGCGCAACGG-3' (SEQ ID NO: 13) |
| X05874 (aerobactin receptor FS8FseqF1) | 5'-GACAGCCGACAACTGGACTC-3' (SEQ ID NO: 14) |
| X05874 (aerobactin receptor FS8FseqF2) | 5'-AATCCCGGCAGCTTCAGTTG-3' (SEQ ID NO: 15) |
| X05874 (aerobactin receptor FS8FseqF3) | 5'-CCTCCAACCAGATGTTCTTC-3' (SEQ ID NO: 16) |
| X05874 (aerobactin receptor FS8FseqF4) | 5'-AACGGCCATCTTCCTCTAAC-3' (SEQ ID NO: 17) |
| X05874 (aerobactin receptor FS8FseqF5) | 5'-AGAGCACCACCTCCTTTGAC-3' (SEQ ID NO: 18) |

Example 2

Overexpression and Purification of Protein Aggregates

The following protocol was used to overexpress and extract proteins using denaturing conditions:

Day 1: A 100 ml terrific broth culture+ampicillin selective antimicrobial marker was inoculated with either PapG, IutA, or FimH transformant and incubated overnight at 37° C.

Day 2: The 100 ml overnight culture was spun down and resuspend in a total volume of 5 ml terrific broth+ampicillin and inoculated into 1000 ml of terrific broth containing ampicillin (in a 2 flask to an O.D.600 of 0.1 and incubated at 37° C. until the OD600 reached 0.6. Before adding IPTG, a 1.5 ml aliquot of the cells was taken, centrifuged in a microcentrifuge tube and dissolved in 120 μl of 1× sample buffer for further analysis. Isopropyl β-D-1-thiogalactopyranoside (IPTG) was added to the culture at a concentration of 1 mM and incubated for a another 2 hours at 37° C. (1.0 ml of 1 M in 1000 ml=1 mM). The culture was spun down in 500 ml bottles at 4000 rpm for 15 minutes. The supernatant was decanted and discarded, the pellets resuspended in a total volume of 4 ml of 25% sucrose/50 mM Tris pH 8.0 and transferred to Corning 50 ml centrifuge tubes and frozen at −70° C. for 30 minutes. Cells were thawed at room temperature and a total volume of 1 ml of 10 mg/ml lysozyme solution (10 mg lysozyme per ml of 0.25 M Tris pH 8.0) was added to the 4 ml of cells which were placed on ice for 15 minutes. To lyse the cells, 30 ml of freshly prepared RIPA/TET (5:4-35 ml 2× RIPA+28 ml TET) detergent mixture was added, thoroughly mixed and placed on ice for 5 minutes. The following recipe was used for 2× RIPA and TET:

2× RIPA

| | |
|---|---|
| 1.0M Tris pH 7.5 →20 mM | 700 μl |
| 2.5M NaCl →300 mM | 4.2 ml |
| Deoxycholic Acid (2%) | 0.7 g |
| NP-40 (2%) | 700 μl |
| Deionized Water | → 35 ml (29.4 ml) |

TET

| | |
|---|---|
| 2M Tris pH 8.0 → 0.1M | 1.5 ml |
| 0.25M EDTA pH 8.0 → 0.05M | 6 ml |
| Triton X-100 (2%) | 600 μl |
| Deionized Water | → 30 ml (21.9 ml) |

Using a large probe, the pellet was sonicated for 3×30 seconds (or until the viscosity is that of water) at maximum setting. The lysed cells were then transferred to 50 ml Nalgene centrifuge tubes and centrifuged at 12,000 rpm for 20 minutes at 4° C. The supernatant was discarded and protein resuspended in 500 μl of 4M guanidine and was allowed to dissolve at 4° C. overnight then transferred the supernatant to a fresh Eppendorf tube after centrifugation. The proteins were stored at −20° C.

Example 3

Formulation, Preparation, and Immunization of Broiler Chickens

A total of 50 broiler day-old chicks were purchased from a commercial poultry hatchery. Birds were received unvaccinated to minimize interference with the study. Birds were transferred immediately to the animal care facility and were placed in 4 cages with fresh water and commercially prepared antibiotic-free feed provided ad libitum. The room temperature was set at 33° C. to ensure enough warmth for the first growth phase.

Blood samples were collected 1 week after the arrival to a blank tube from the wing veins from chickens in all groups. A total of 0.5 ml blood was collected and tubes were allowed to set at room temperature for 30 minutes to ensure proper clotting. Blood was then incubated at 37° C. for 2 hours to generate serum which was collected into a 0.2 ml tubes. Collected serum was centrifuged at 5000×rpm for 5 minutes to precipitate any RBCs aspired during the process. Serum was transferred into a new tube and stored at −20° C. until used.

Immunization of Chickens

Chickens were divided into 5 groups, with 10 birds per group as detailed in Table 3.

TABLE 3

Description of the groups in the study. "LKT" refers to the protein product of the *Pasteurella haemolytica* leukotoxin gene fusions described above. "Mixture" refers to a mixture of all three gene fusions. The "LKT" immunogen does not have an antigen conjugated to it. "IM" refers to intramuscular administration. "IN" refers to intranasal administration.

| Group | Immunogen | Route |
|---|---|---|
| 1 | Mixture | IM |
| 2 | PapG-LKT | IN |
| 3 | IutA-LKT | IN |
| 4 | FimH-LKT | IN |
| 5 | LKT | IN |

Dosage Calculation

Each group had 10 chickens, with each chicken receiving 20 μg of total protein. Subjects in groups 2-5 received 20 μg of the protein indicated in Table 3. Subjects in group 1 received 20 μg of total protein, split equivalently between PapG-LKT, IutA-LKT, and FimH-LKT. Each dose was incorporated into 100 μl of chitosan-tripolyphosphate (chitosan-TPP). Based on concentrations determined using a spectrophotometer the following amounts were mixed, as described in Table 4.

TABLE 4

Components of each formulation administered to the birds.

| Group | TPP solution (μL) | Phosphate buffer (μL) | Protein (μL) | Chitosan solution (μL) | Total volume (μL) |
|---|---|---|---|---|---|
| Mix | 163.2 | 382 | PapG 20 IutA 20 FimH 40 | 375 | 1000 |
| PapG (Conc. = 1.6 μg/(μL) | 163.2 | 774.3 | 187.5 | 375 | 1500 |
| FimH (Conc. = 0.2 μg/μl) | 163.2 | 761.8 | 200 | 375 | 1500 |
| IutA (Conc. = 2 μg/μl) | 163.2 | 811.8 | 150 | 375 | 1500 |
| LKT (Conc. = 8.4 μg/μl) | 163.2 | 926.8 | 35 | 375 | 1500 |

Feed was withheld in the morning and vaccination was performed as described in Table 4 at 3:00 PM. All chickens were checked for any signs of lameness or difficulty breathing with none observed throughout the experiment. Excess vaccines were stored at 4° C. and were analyzed using the following techniques: (1) particle size analysis by Zetasizer (Malvern); (2) scanning electron microscopy (SEM); and (3) enzyme-linked immunosorbent assay (ELISA; for protein entrapment efficiency).

Blood samples were obtained 12 days after the first immunization was performed, and serum was isolated. From each bird 200-300 μl of blood were collected. Blood was allowed to clot for 30 minutes before transportation. Samples were incubated at 37° C. for 2 hrs. Serum was collected early morning, centrifuged and stored at −20 until analyzed by ELISA.

A second Immunization was performed using formulations similar to those described in Table 4. TPP was added to the empty tube first, followed by freshly prepared 2M Urea, then 15 μl of acetic acid were applied. Protein was added next and finally chitosan was added drop wise. The turbidity of the formulations increased slightly when adding the last few drops of chitosan, but the formulations remain relatively clear. The tubes were then centrifuged at 8,000× rpm and the excess urea was removed. The pellet was resuspended in PBS to the final volume for the group (see Table 4).

Euthanasia and Sample Collection

Birds were euthanized using the $CO_2$ asphyxiation method. From each bird a blood sample of 3-4 ml was collected into an EDTA blood tube and 1 ml into a blank tube before euthanasia. EDTA tubes were mixed gently and placed on ice while blank tubes were incubated at room temperature for 2 hours to allow the serum to develop.

Lung washes were collected using 10 ml of PBS-0.05% Tween by directly opening a small slit in the trachea aseptically and flushing twice us a 21 G needle attached to a 10 ml syringe. The maximum amount of recovered washes was 8 ml and average was 5 ml. Spleens were collected aseptically in 3 ml of ice cold PBS and stored on ice until processed as described below.

A segment of the intestine including the jejunum, ileum, and duodenum was collected aseptically in a sterile Petri dish and stored on ice until processed.

Samples were transported to the lab and processed immediately as described below.

Splenocytes

For each sample a separate 50 ml Falcon tube was labelled and used. A sterile 100 μl strainer was used to obtain a single cell suspension. Using the head of a sterile Pasteur pipette each spleen was gently squeezed through the strainer. For each spleen a total of 10 ml of RPMI 1640 supplemented with antibiotics was used to process the sample. The volume was brought to 20 ml and samples were centrifuged at 2500 rpm for 10 minutes. Splenocytes were resuspended in 20 ml of media and centrifuged again. The pellet was resuspended in 5 ml freezing media (90% fetal bovine serum+10% DMSO). Samples were immediately stored in pre-labeled cryovials at −80° C. until processing.

Intestinal Wash

A segment of the intestine including the jejunum, illume, and duodenum was collected from each sample to obtain the IgA secreted into the intestine of immunized birds. Each segment was tied at one end using a hemostat, while the other end was held tightly using a forceps. A total of 10 ml of PBS-0.05% Tween 20 was infused into the tied intestine and the filled intestine was massaged gently. The intestinal secretions were collected into a 15 ml Falcon tube, vortexed for 45-60 seconds, and stored on ice until centrifugation at 6,000×rpm for 20 minutes to precipitate fecal material. One ml of the supernatant was collected in a pre-labelled sterile Eppendorf tube and stored at −80° C. immediately until needed.

Blood for PBMC's

From each bird a blood sample of 8 ml was collected into an EDTA blood tube which was inverted gently several times to ensure proper mixing. Samples were stored on ice until processing. A 1:1 volume of Histopaque 1077 (Sigma) was used to layer the blood carefully. Samples were centrifuged at 800×g for 20 minutes with the brakes off to avoid the disturbance of the samples. The buffy coat formed at the interface between the blood and Histopaque containing the white blood cells was collected into a 15 ml Falcon tube. Cells were washed twice using 15 ml RPMI 1640 supplemented with antibiotics. Cells were stored using freezing media (90% fetal bovine serum+10% DMSO) at −80° C. immediately until needed.

Lung Washes

From each bird a sample from lung secretion was collected to obtain the IgA secreted into the lungs of immunized birds. A total of 10 ml of PBS-0.05% Tween 20 was infused into the trachea and aspirated. The washes were collected into a 15 ml Falcon tube, vortexed for 45-60 seconds, and stored on ice until centrifugation at 6,000×rpm for 20 minutes to precipitate large proteins. One ml of the supernatant was collected in a pre-labelled sterile Eppendorf tube and stored at −80° C. immediately until needed.

Serum Collection

Serum was allowed to separate as described above. The serum was collected in an Eppendorf tube and centrifuged at 6,000 rpm for 5 minutes to precipitate any red blood cells (RBC's).

Enzyme-linked Immunosorbent Assay (ELISA)

Flat bottom microtiter plates (Corning Costar Maxisorp) were coated overnight with a 100 μl of 1 μg/ml of the corresponding immunogen (LKT, IutA, PapG, or FimH) suspended in 2M guanidine thiocyanate at 4° C. Excess coating buffer was removed and 10% fetal bovine serum (FBS) in PBS was added to the wells to block non-specific binding. The plates were washed with 0.05% Tween-20 in PBS after two hours of incubation at 37° C. Each serum sample was diluted 1:100 in 10% FBS-PBS and a 100 μl was added to each well. As a control, each plate contained two negative serum samples and one blank. The plates were incubated for one hour at 37° C. and washed as above. Horseradish peroxidase (HRP)-labelled goat anti-chicken IgY (Abcam) was added as a secondary antibody and plates were incubated for 1 hour at 37° C. After washing the plates, TMB One Component HRP Microwell Substrate (Sigma) was added and plates were incubated for 14 minutes. Substrate development was stopped using Liquid Stop Solution (Sigma). O.D. was measured spectrophotometrically at wavelength of 450 nm (Sunrise microplate reader, Tecan). All samples were performed in duplicates and the average was used as a final reading.

Figure 7:
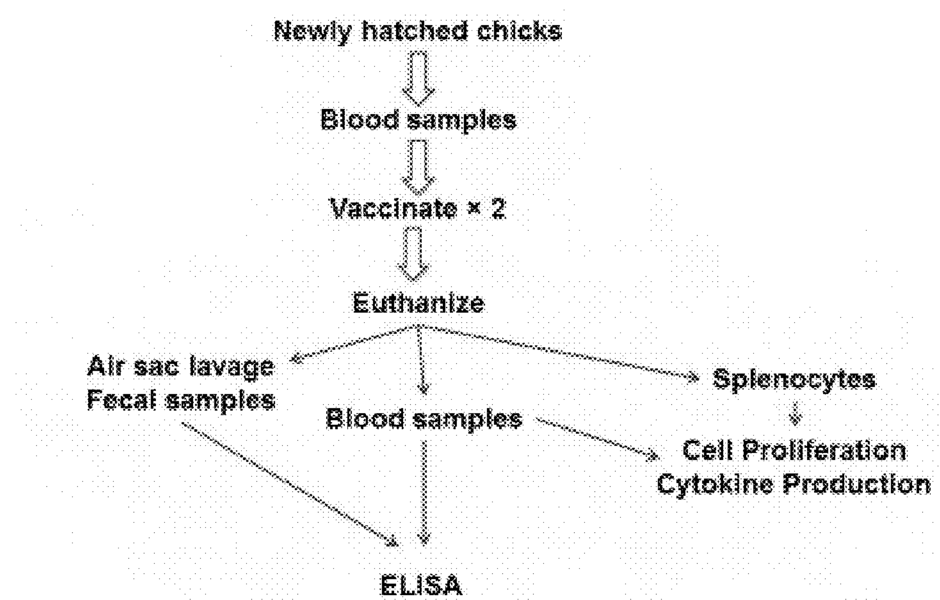
FIG. 7 provides an overview of the experimental design and sample collection process described in Example 3.

FIG. 7 provides an overview of the experimental design and sample collection process, as described above.

Figure 8:
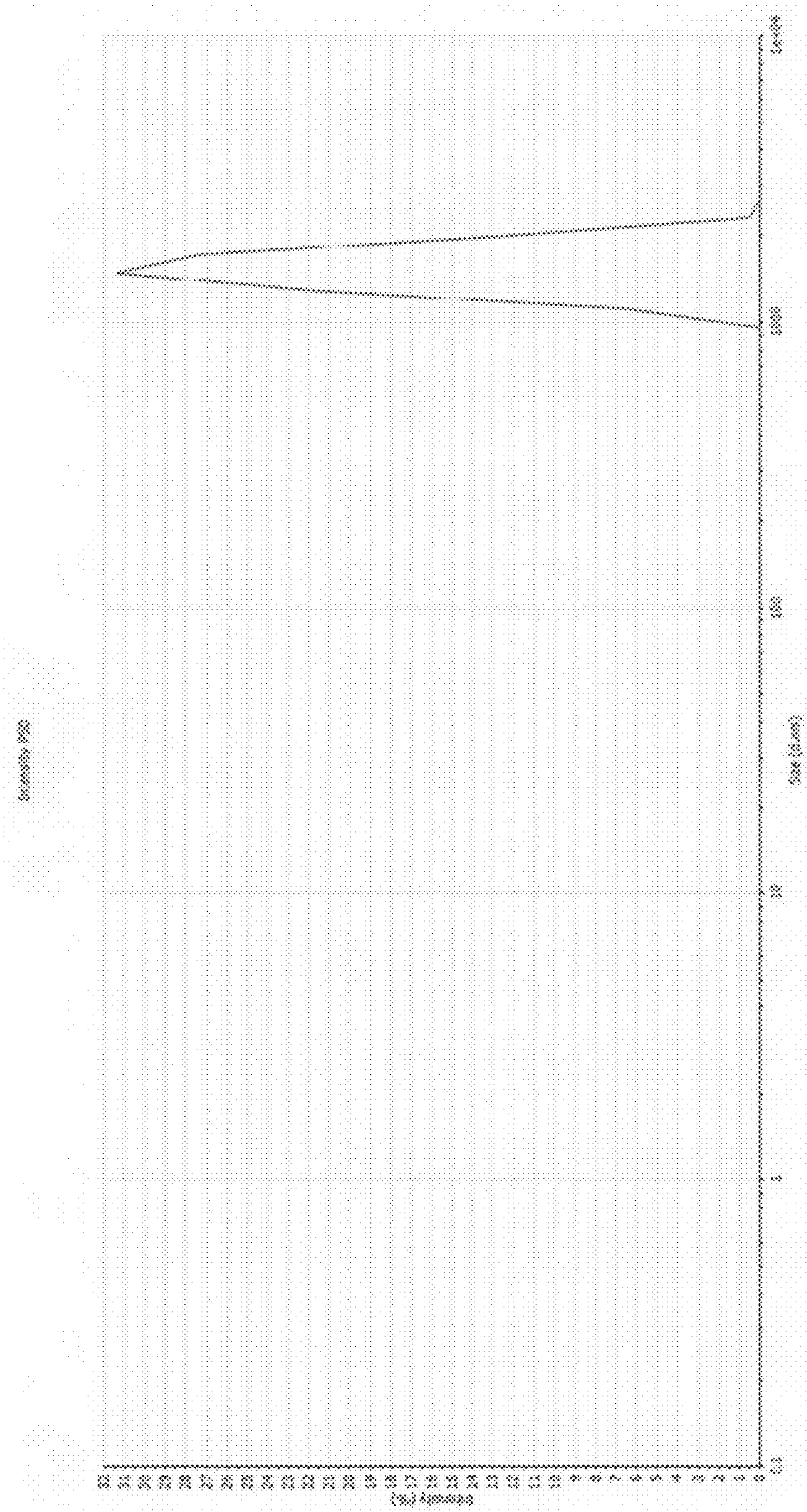
FIG. 8 provides the particle size distribution and homogeneity of IutA-LKT fusion proteins entrapped in chitosan, using a Zetasizer (Malvern), as described in Example 3.

FIG. 8 provides the particle size distribution and homogeneity of IutA-LKT fusion proteins entrapped in chitosan, using a Zetasizer (Malvern), as described above.

Figure 9:
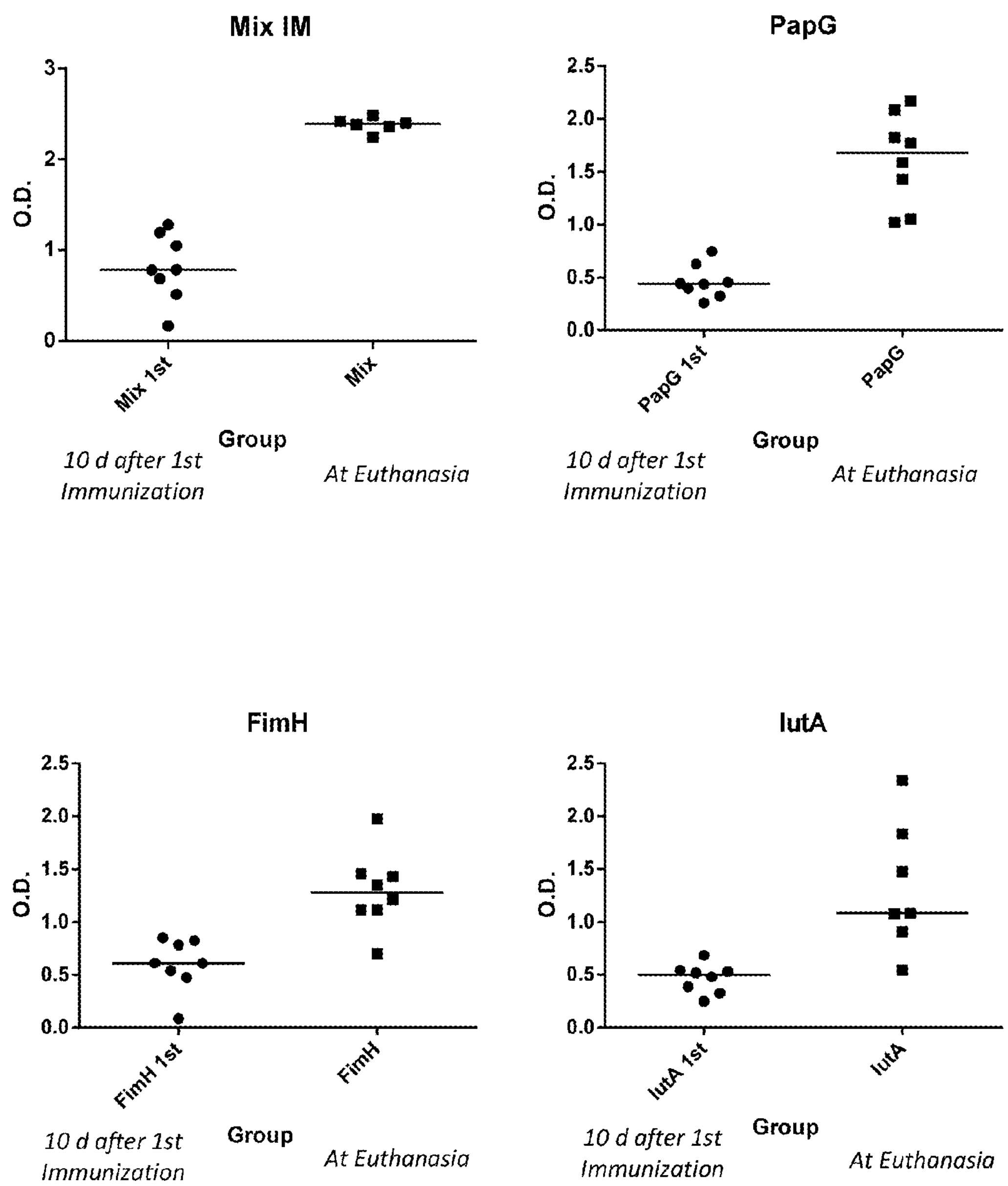
FIG. 9 provides the results of the ELISA assay performed as described in Example 3, measuring IgY antibody titers in the serum of immunized birds. Each panel of FIG. 9 presents results obtained from samples collected 10 days after the first immunization (left-side of each panel), and after euthanasia (right side of each panel).

FIG. 9 provides the results of an ELISA assay performed as described above, showing IgY antibody activity in the serum of immunized birds. Each panel of FIG. 9 presents results obtained from samples collected 10 days after the first immunization (left-side of each panel), and after euthanasia (right side of each panel).

Figure 10:
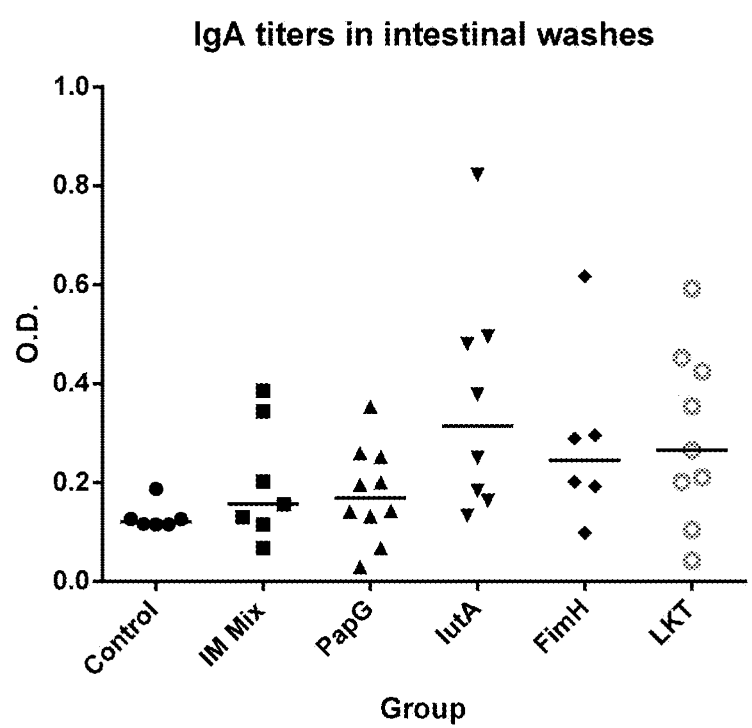
FIG. 10 provides the results of an ELISA assay performed as described in Example 3, measuring secretory IgA (sIgA) titers in the intestinal washes of immunized birds.

FIG. 10 provides the results of an ELISA assay performed as described above, showing secretory IgA (sIgA) activity in the intestinal washes of the immunized birds. A one-way analysis of variance (ANOVA) analysis shows that there is a significant difference ($P<0.05$) between the means of the of the groups of that received IutA, FimH, and LKT as an immunogen and the control. There was no significant difference between the means of the groups that received an IM protein mixture or PapG and the control.

The immunization schedule described above resulted a humoral and mucosal immune responses in broiler chickens against the antigens used in the formulation. These antigens are vital for APEC colonization and therefore a strong immune response against them will impair the infection process. A vaccine comprising antigens fused to leukotoxin A and entrapped in chitosan is capable of inducing an immune response.

Example 4

Assay Optimization for Monitoring Proliferation and Cytokine Production by Peripheral Blood Mononuclear Cells (PBMCs) and Splenocytes This assay is designed to characterize the cell-mediated immune responses induced by the vaccine described above. Cells are stored in freezing media as described above (90% FBS, 10% DMSO). Cells are thawed and processed for proliferation assays and IFN-y secretion using the following protocol:

Protocol

Reagents Required:

- RPMI media-1640, Sigma
- Fetal Bovine Serum (FBS), Sigma
- Penicillin-streptomycin, Cat #P0781, Sigma
- PMA Cat #P8139, Sigma
- Ionomycin Cat #I3909, Sigma
- Centrifuge (50 ml tubes)
- Microscope
- BSC
- Ice bucket and ice
- Hemocytometer (disposable)
- Trypan blue Counting and Preparation of PBMCs and Splenocytes

- Prepare RPMI media (sterile)+10% FBS (sterile and heat-inactivated for lhr at 56° C.)+1% Antibiotic(penicillin/streptomycin):
  - Remove 55 ml media, and add 50 ml FBS+5 ml pen/strep
  - Place prepared media in the 37° C. water bath for 5-10 minutes.
- Add 20 ml of warm prepared media to pre-labeled Falcon tubes (one tube/sample)
- One tube at a time, thaw the PBMCs/splenocytes quickly in the 37° C. water bath until half the pellet becomes liquid
- Spray the vials containing the PBMCs/splenocytes with 70% ethanol and place inside the BSC
- Drop the PBMCs/splenocytes into the corresponding Falcon tube
- Rinse each vial with media from the corresponding Falcon tube. Make sure to take out all the cells.
- Once all cells have been thawed, centrifuge Falcon tubes at 1600 rpm at 4° C. for 5 minutes
- Check if there is a pellet and place the tubes on ice
- Inside the BSC decant the supernatant
- Add 5 ml of complete media to each Falcon tube and pipette up and down slowly and gently (do not vortex the cells)
- To prepare the PBMCs for counting, add 90 μl of filtered Trypan blue to appropriately labelled 0.5 ml Eppendorf tubes
- Mix Falcon tubes by gentle inversion
- Take 10 μl of cell suspension (cells+media) and add into 90 μl of Trypan blue in appropriately labelled 0.5 ml Eppendorf tube. Mix by tapping.
- Pipette up and down and take 10 μl of cell suspension-dye solution and place into a labelled hemocytometer
- Repeat above steps with next Falcon tube/sample and place cell suspension-dye solution into the other side of the hemocytometer
- Count the cells in each side, recording the number in each quadrant
- Take the average of the 4 quadrants
- Number of cells/ml=average×dilution factor×10000

Example=177/4=44.3×10×10000=4.4×$10^6$ cells/ml

- Prepare 2.0×$10^6$ cells/ml

Example: 4.4×$10^6$ cells/ml×5 ml=2.0×$10^6$ cells/ml×V2=11 ml final volume

- Spin cells down as above, and this time resuspend as above but with calculated final volume of media
- Keep cell suspensions on ice until ready to add to plates Preparation of Stimulants

- Prepare stimulants in complete media as per calculations (see plate plan—remember to double the concentrations)
- Leave on ice in the BSC PMA/Ionomycin Preparation:

PMA stock: 5 mg/ml in DMSO, aliquots of 50 μl, store at −80 C)

Ionomycin stock: 1 mM in DMSO (add 1.3 ml DMSO to the 1 mg vial and mix).

Dilute 25 μl of PMA in 2.5 ml of culture media (10% FCS) to make a stock of 50 μg/ml (diluted PMA)

Mix 20 μl of diluted PMA (final 5 μg/ml)+13.5 μl of ionomycin (final 50 μg/ml)+166.5 μl of culture media.

Add 10 μl of PMA/Ionomycin mix per 1 ml of cells (Final concentrations of PMA and Ionomycin in media will be 50 ng/ml and 500 ng/ml, respectively). Per tube of 200 μl of cells add 2 μl.

Brefeldin A (BFA)

Dissolve 1 mg of BFA (Sigma #) in 1 ml of 100% EtOH, and store at −80 C.

Add 10 μl of BFA per 1 ml of cells

CFSE Staining for Proliferation:

CFSE is a dye that passively diffuses into cells. It is colorless and nonfluorescent until the acetate groups are cleaved by intracellular esterases to yield highly fluorescent carboxyfluorescein succinimidyl ester. The succinimidyl ester group reacts with intracellular amines, forming fluorescent conjugates that are well retained and can be fixed with aldehyde fixatives. Excess unconjugated reagent and by-products passively diffuse to the extracellular medium, where they can be washed away. The dye-protein adducts that form in labeled cells are retained by the cells throughout development and meiosis, and can be used for in vivo tracing using flow cytometry. Herein, we optimized a CFSE assay to label PBMC's and splenocytes collected from the immunized chickens and monitor their proliferation in the presence of the antigen used for immunization.

Cells were resuspended in prewarmed PBS-0.1% BCS at a final concentration of 1×$10^6$ cells/mL. A total of 2 μL of 5 mM stock CFSE solution per 1 ml of cells for a final working concentration of 10 μM was added. Cells were stimulated using a final concentration of 2 μg/ml of the protein. Stimulation continued for 96 hours at 41° C. at 5% $CO_2$ concentration. Cells were checked for viability using propidium iodide (PI) staining 11. Equivalents The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in this application, in applications claiming priority from this application, or in related applications. Such claims, whether directed to a different invention or to the same invention, and whether broader, narrower, equal, or different in scope in comparison to the original claims, also are regarded as included within the subject matter of the inventions of the present disclosure.

12. Sequence Listing

GenBank AJ225176

*Escherichia coli* fimD, fimF, fimG, fimH, uxaA & gntP

SEQ ID NO: 1

```
   1   gcgcgcgttg ggataaaact gctcatgacg ctaacccaca ataataagcc gctgccgttt

  61   ggggcgatgg tgacatcaga gagtagccag agtagcggca ttgttgcgga taatggtcag

 121   gtttacctca gcggaatgcc tttagcggga aaagtgcagg tgaaatgggg agaagaggaa

 181   aatgctcact gtgtcgccaa ttatcaactg ccaccagaga gtcagcagca gttattaacc

 241   cagctatcag ctgaatgtcg ttaagggggc gtgatgagaa acaaaccttt ttatcttctt

 301   tgcgcttttt tgtggctggc ggtaagtcac gctttggctg cggatagcac gattactatc

 361   cgcggctatg tcagagataa tggctgtagt gtggccgctg aatcaaccaa ttttactgtt

 421   gatctgatgg aaaacgcggc gaagcaattt aacaacattg gcgcgacgac tcctgttgtt

 481   ccatttcgta ttttgctgtc accctgtggt aacgccgttt ctgccgtaaa ggttgggttt

 541   accggcgttg cagatagcca caatgccaac ctgcttgcac ttgaaaatac ggtgtcagcg

 601   gctgcgggac tgggaataca gcttctgaat gagcagcaaa atgagatacc ccttaatgcc

 661   ccatcgtccg cgatttcgtg gacgaccctg acgccgggta aaccaaatac gttgaatttt

 721   tacgcccggc taatggcgac acaggtgcct gtcactgcgg ggcatattaa tgccacggct

 781   accttcactc ttgaatatca gtaactggag atgctcatga aatggtgcaa acgtgggtat

 841   ttattggcgg caatgttggc gttcgcaagt gcgacgatac aggcagccga tgtcaccatc

 901   acggtgaacg gtaaggtcgt cgccaaaccg tgcacagttt ccaccaccaa tgccacggta

 961   gatctcggcg atctttattc tttcagtctt atgtctgccg ggcggcatc ggcctggcat

1021   gatgttgcgc ttgagttgac taattgtccg gtgggaacgt cgagggtcac tgccagcttc

1081   agcggggcag ccgacagtac cggatattat aaaaatcagg ggaccgcgca aaacatccag

1141   ttagagctac aggatgacag tggcaacaca ttgaatactg gcgcaaccaa aacagttcag

1201   gtggatgatt cctcacaatc agcgcacttc ccgttacagg tcagagcatt gaccgtaaat

1261   ggtggagcca ctcagggaac cattcaggca gtgattagca tcacctatac ctacagctga

1321   acccaaagag atgattgtaa tgaaacgagt tattaccctg tttgctgtac tgctgatggg

1381   ctggtcggta aatgcctggt cattcgcctg taaaaccgcc aatggtaccg caatccctat

1441   tggcggtggc agcgccaatg tttatgtaaa ccttgcgcct gccgtgaatg tggggcaaaa

1501   gctggtcgta gatctttcga cgcaaatctt ttgccataac gattacccag aaaccattac

1561   agactatgtc acactgcaac gaggttcggc ttatggcggc gtgttatcta gtttttccgg

1621   gaccgtaaaa tataatggca gtagctatcc tttccctact accagcgaaa cgccgcgggt

1681   tgtttataat tcgagaacgg ataagccgtg gccggtggcg ctttatttga cgccggtgag

1741   cagtgcgggg ggagtggcga ttaaagctgg ctcattaatt gccgtgctta ttttgcgaca

1801   gaccaacaac tataacagcg atgatttcca gtttgtgtgg aatatttacg ccaataatga

1861   tgtggtggtg cccactggcg gctgcgatgt ttctgctcgt gatgtcaccg ttactctgcc

1921   ggactaccct ggttcagtgc cgattcctct taccgtttat tgtgcgaaaa gccaaaacct
```

-continued

12. Sequence Listing

```
1981   ggggtattac ctctccggca caaccgcaga tgcgggcaac tcgattttca ccaataccgc
2041   gtcgttttca cccgcgcagg gcgtcggcgt acagttgacg cgcaacggta cgattattcc
2101   agcgaataac acggtatcgt taggagcagt agggacttcg gcggtaagtc tgggattaac
2161   ggcaaattac gcacgtaccg gagggcaggt gactgcaggg aatgtgcaat cgattattgg
2221   cgtgactttt gtttatcaat aaagaaatca cagggcattg ctaatgcagg tacgcaatat
2281   tacctgaagc taaaatctgc acgttagccc tttgtaggcc agataagacg cgtcagcgtc
2341   gcatctggca taaacaaagc gcactttacc gacaatccga acagagcctg ccaatggcag
2401   gctcaggtgc tcttttacgc taccatgcta ataatcagca caataatcag cccaaccacg
2461   gagttgacca gctccagcag accccaggtt ttcaacgtgt cttttactga caggtcaaag
2521   taatctaaga ggcattgcta atgtagggaa tgtgtctgaa cctgcggtca ttgtcagtac
2581   cagcatcagg ccaatgccga ataccaccca gagaatgtta agcacatgca taacgtttta
2641   ccttacctgg ttgaaccgtt gttattttgg gcgacatgtt atgtaaattg gtcaaccatt
2701   gttgcgatga atgtcacatc ctctgatcaa taaccatcga ttaccctttg ctgcaatttg
2761   cagcaacaac caggagagtg aaattcttgt gatgtggtta accaatttta gaattcgggt
2821   tgacatgtct taccaaaagg tagaacttat acgccatctc atccgatgca acgccacggc
2881   tgcggtctgg ttgttcatcc ggatacctaa acaactccgg ggctccacgt ctctttgctg
2941   tggaacccac tatgtgaaag aggaaaaatc atggaacaga cctggcgctg gtacggccca
3001   aacgatccgg ittctttagc tgatgtccgt caggcgggcg caactggcgt ggttaccgcg
3061   ctgcaccata tcccgaacgg cgaagtatgg tccgtagaag agatcctcaa acgcaaggcg
3121   atcgttgaag acgcaggcct ggtgtggtct gtcgttgaaa gcgtaccaat tcacgaagat
3181   atcaaaaccc acactggcaa ctatgagcag tggattgcta actatcagca gaccctgcgc
3241   aacctggcgc agtgcggcat tcgcaccgtg tgctacaact tcatgccggt gctcgactgg
3301   acccgtactg acctcgaata cgtgctgcca gacggctcca aagctctgcg cttcga
```

GenBank AJ225176
Type 1 fimbriae adhesin, precursor polypeptide (FimH)

SEQ ID NO: 2

```
MKRVITLFAVLLMGWSVNAWSFACKTANGTAIPIGGGSANVYVNLAPAVNVGQKLVVDLSTQIFCHNDY
PETITDYVTLQRGSAYGGVLSSFSGTVKYNGSSYPFPTTSETPRVVYNSRTDKPWPVALYLTPVSSAGG
VAIKAGSLIAVLILRQTNNYNSDDFQFVWNIYANNDVVVPTGGCDVSARDVTVTLPDYPGSVPIPLTVY
CAKSQNLGYYLSGTTADAGNSIFTNTASFSPAQGVGVQLTRNGTIIPANNTVSLGAVGTSAVSLGLTAN
YARTGGQVTAGNVQSIIGVTFVYQ
```

GenBank X61237
*E. coli* papG gene for P-pili protein

SEQ ID NO: 3

```
  1    atgaaaaaat ggttcccagc tttgttattt tccttgtgtg tgtctggtga gtcctctgca
 61    tggaataata ttgtctttta ctcccttgga aacgttaact cttatcaggg agggaatgtg
121    gtgattactc aaaggccaca atttataact tcgtggcgcc cgggcattgc tacggtaacc
181    tggaatcagt gtaatggtcc tgggtttgct gatggttcct gggcttacta cagggagtat
241    attgcgtggg tagtattccc caaaaaggtt atgaccaaaa atggatatcc cttatttatt
301    gaggttcata ataaaggtag ctggagtgag gagaatactg gtgacaatga cagctatttt
361    tttctcaagg ggtataagtg ggatgagcgg gcctttgatg caggtaattt gtgtcagaaa
421    ccaggagaaa caacccgtct gactgagaaa tttgacgata ttatttttaa agtcgcccta
481    cctgcagatc ttcctttagg ggattattct gttacaattc catacacttc cggcatgcag
541    cgtcatttcg cgagttactt gggggcccgt tttaaaatcc catacaatgt ggccaaaact
```

-continued

| 12. Sequence Listing |
| --- |

601 ctcccaagag agaatgaaat gttattctta tttaagaata tcggcggatg ccgtccttct 661 gcacagtctc tggaaataaa gcatggtgat ctgtctatta atagcgctaa taatcattat 721 gcggctcaga ctctttctgt gtcttgcgat gtgcctgcaa atattcgttt tatgctgtta 781 agaaatacaa ctccgacata cagccatggt aagaaatttt cggttggtct ggggcatggc 841 tgggactcca ttgtttcggt taacggggtg gacacaggag agacaacgat gagatggtac 901 aaagcaggta cacaaaacct gaccatcggc agtcgcctct atggtgaatc ttcaaagata 961 caaccaggag tactatctgg ttcagcaacg ctgctcatga tattgccata a GenBank X61237
PapG Protein

SEQ ID NO: 4

MKKWFPALLFSLCVSGESSAWNNIVFYSLGNVNSYQGGNVVITQRPQFITSWRPGIATVTWNQCNGPGFA
DGSWAYYREYIAWVVFPKKVMTKNGYPLFIEVHNKGSWSEENTGDNDSYFFLKGYKWDERAFDAGNLC
QKPGETTRLTEKFDDIIFKVALPADLPLGDYSVTIPYTSGMQRHFASYLGARFKIPYNVAKTLPRENEMLF
LFKNIGGCRPSAQSLEIKHGDLSINSANNHYAAQTLSVSCDVPANIRFMLLRNTTPTYSHGKKFSVGLGHG
WDSIVSVNGVDTGETTMRWYKAGTQNLTIGSRLYGESSKIQPGVLSGSATLLMILP

*E. coli* plasmid pFS8 cloacin DF13/aerobactin receptor gene
(Includes IutA)

SEQ ID NO: 5

1 gatctgcacg tattcttaat cgcgtaatgg gacgtgattt attcgatctc agtatgccgc 61 ccgccctgat tcagtggcgc aggcacctag ggaaaacgca gccggacttg tctttaactc 121 gctacacagc atctttgggc tgattttttc cgcccgtatg gaggaataat gatgataagc 181 aaaaagtata cgctttgggc tctcaaccca ctgcttctta ccatgatggc gccagcagtc 241 gctcaacaaa ccgatgatga aacgttcgtg gtgtctgcca accgcagcaa tcgcaccgta 301 gcggagatgg cgcaaaccac ctgggttatc gaaaacgccg aactggaaca gcagattcag 361 ggcggcaaag agcttaaaga cgcactggct cagctgatcc ctggccttga cgtcagcagc 421 cggagccgca ccaactacgg tatgaatgtg cgtggccgcc cgctggtcgt gctggttgac 481 ggcgtgcgtc tcaactcttc acgtaccgac agccgacaac tggactctat agatcctttt 541 aatatgcacc atattgaagt gatcttcggt gcgacgtccc tgtacggcgg cggcagtacc 601 ggtggcctga tcaacatcgt gaccaaaaaa ggccagccgg aaaccatgat ggagtttgag 661 gctggcacca aaagtggctt tagcagcagt aaagatcacg atgaacgcat tgccggagct 721 gtctccggcg gaaatgagca tatctccgga cgtctttccg tggcatatca gaaatttggc 781 ggctggtttg acggtaacgg cgatgccacc ttgcttgata acacccagac cggcctgcag 841 tactccgatc ggctggacat catgggaact ggtacgctga acatcgatga atcccggcag 901 cttcagttga tcacacagta ctataaaagc cagggcgacg acgattacgg gcttaatctc 961 gggaaaggct tctctgccat cagagggacc agcacgccat tcgtcagtaa cgggctgaat 1021 tccgaccgta ttcccggcac tgacgggcat ttgatcagcc tgcagtactc tgacagcgct 1081 tttctgggac aggagctggt cggtcaggtt tactaccgcg atgagtcgtt gcgattctac 1141 ccgttcccga cggtaaatgc gaacaaacag gtgacggctt tctcttcgtc acagcaggac 1201 accgaccagt acggcatgaa actgactctg aacagcaaac cgatggacgg ctggcaaatc 1261 acctgggggc tggatgctga tcatgagcgc tttacctcca accagatgtt cttcgacctg 1321 gctcaggcaa gcgcttccgg agggctgaac aacaagaaga tttacaccac cgggcgctat 1381 ccgtcgtatg acatcaccaa cctggcggcc ttcctgcaat caggctatga catcaataat 1441 ctctttaccc tcaacggtgg cgtacgctat cagtacactg aaaacaagat tgatgatttc -continued

| 12. Sequence Listing |
|---|
| 1501 atcggctacg cgcagcaacg gcagattggc gccgggaagg ctacatccgc cgacgcattc |
| 1561 tggcggctca gtcgattacg acacttcctg ttcaacgccg gtctgctgat gcacatcacc |
| 1621 gaaccgcagc aggcatggct caacttctcc cagggcctgg agctgccgga cccgggtaaa |
| 1681 tactatggtc gcggcatcta tggtgctgca gtgaacggcc atcttcctct aacaaagagt |
| 1741 gtgaacgtca gcgacagcaa gctggaaggc gtgaaagtcg attcttatga gctgggctgg |
| 1801 cgctttactg gcaataatct gcgtacccaa atcgcggcct actattcgat ttctgataag |
| 1861 agcgtggtgg cgaataaaga tctgaccatc agcgtggtgg acgacaaacg ccgtatttac |
| 1921 ggcgtggaag gtgcggtgga ctacctgatt cctgatactg actggagtac cggagtgaac |
| 1981 ttcaacgtgc tgaaaactga gtcgaaagtg aacggtacct ggcagaaata cgatgtgaag |
| 2041 acagcaagcc catcaaaagc gacagcctac attggctggg caccggaccc gtggagtctg |
| 2101 cgcgtgcaga gcaccacctc ctttgacgtg agcgacgcgc agggctacaa ggtcgatggc |
| 2161 tataccaccg tggatctgct cggcagttat cagcttccgg tgggtacact cagcttcagc |
| 2221 attgaaaacc tcttcgaccg tgactacacc actgtctggg ggcagcgtgc accactgtac |
| 2281 tacagcccgg gttacggccc agcgtcactg tacgactaca aaggcagggg ccgaaccttt |
| 2341 ggtctgaact actctgtgct gttctgaccg gtattccttt acaacaaagg tacgctgata |
| 2401 tcaacatggc cgctgacagc caagttgata tcatataata cacgacataa tctgtagtca |
| 2461 gggaggatag actctttact gactacagat tatgtcctgt tccgtgctca tttcctcaaa |
| 2521 aaaatacaag aaaagaatta gtattctaac aaaaagtgaa ataaattgta tcaaactccc |
| 2581 tcttttaatc ctgttgagta aatcagcttt tgcaatagga ttgaaagagt gtaagtggaa |
| 2641 tctcttccgg atactcgtta ccaccgtggc tagaatatct acggctgcgg gggtgatgct |
| 2701 gccaacttac tgatttagtg tatgatggtg tttttgaggt gctccagtgg cttctgtttc |
| 2761 tatcagctg |
| IutA Amino Acid Sequence |
| SEQ ID NO: 6 |
| 1 mmiskkytlw alnpllltmm apavaqqtdd etfvvsanrs nrtvaemaqt twvienaele |
| 61 qqiqggkelk dalaqlipgl dvssrsrtny gmnvrgrplv vlvdgvrlns srtdsrqlds |
| 121 idpfnidhie visgatslyg ggstgglini vtkkgqpetm mefeagtksg fssskdhder |
| 181 iagavsggne hisgrlsvay qkfggwfdgn gdatlldntq tglqysdrld imgtgtlnid |
| 241 esrqlqlitq yyksqgdddy glnlgkgfsa irgtstpfvs nglnsdripg terhlislqy |
| 301 sdsaflgqel vgqvyyrdes lrfypfptvn ankqvtafss sqqdtdqygm kltlnskpmd |
| 361 gwqitwglda dherftsnqm ffdlaqasas gglnnkkiyt tgrypsydit nlaaflqsgy |
| 421 dinnlfflng gvryqytenk iddfigyaqq rqiaagkats adaipggsvd ydnflfnagl |
| 481 lmhiterqqa wlnfsqgvel pdpgkyygrg iygaavnghl pltksvnvsd sklegvkvds |
| 541 yelgwrftgn nlrtqiaayy sisdksvvan kdltisvvdd krriygvega vdylipdtdw |
| 601 stgvnfnvlk teskvngtwq kydvktasps katayigwap dpwslrvqst tsfdvsdaqg |

-continued

12. Sequence Listing

```
661    ykvdgyttad llgsyqlpvg tlsfsienlf drdyttvwgq raplyyspgy gpaslydykg

721    rgrtfglnys vlf
```

Leukotoxin Repeat Sequence

SEQ ID NO: 19

LXGGXGNDX

*Pasteurella haemolytica* leukotoxin A protein sequence

SEQ ID NO: 20

```
  1    mgnkltnist nlksswltak sglnrtgqsl akagqslktg akkiilyipk dyqydtdkgn

 61    glqdlvkaae elgievqkee sndiakaqts lgtihnvlgl tergivlsap qldkllqktk

121    vgqaigsten itkgfsnakt vlsgiqsilg svlagmdlde alqnnsnelt lakagleltn

181    slieniansv ktldafgdqi nqlgsklqnv kglsslgekl kglsgfdkts lgldivsgll

241    sgataalvla dknastsrkv gagfelanqv vgnitkayss yilaqrvaag lsstgpvaal

301    iastvslais plsfagiadk fnhakslesy aerfkklgyd gdnllaeyqr gtgtidasvt

361    aintalaaia ggvsaaaags vvaspiallv sgitgvisti lqyskqamfe hvankihnki

421    veweknnpgk nyfengydar ylanlqdnmk fllnlnkelq aerviaitqq qwdnnigdla

481    gisrlgekvl sgkayvdafe egqhlkadkl vqldsakgii dvsntgeakt qhilfrtpll

541    tpgtekrery qtgkyeyitk lhinrvdswk itdgaasstf dltnvvqrig ieldnagnvt

601    ktketkiiak lgegddnvfv gsgtteidgg egydrvhysr gnygaltida tketeqgsyt

661    vnrfvesgka lhevtsthta lvgnreekie yrhsnnqhha gyytkdtlka veeiigtshn

721    difkgskfnd afnggdgvdt idgndgndrl fggkgddiid ggngddfidg gkgndllhgg

781    kgddifvhrq gdgndsites egndklsfsd snlkdltfek vnhhlvitnt kqekvtiqnw

841    freaefakti qnyvatrddk ieeiigqnge ritskqvdel iekgngkiaq seltkvvdny

901    qllkysrdas nsldklissa saftssndsr nvlasptsml dpslssiqfa raa
```

GenBank Accession No. AY212280.1 (GI: 37786764)
*Escherichia coli* strain APEC 41 PapGII (papGII) gene, complete cds

SEQ ID NO: 21

```
  1    atgaaaaaat ggttccctgc tttgttattt tccttgtgtg tgtctggtga gtcctctgca

 61    tggaataata ttgtctttta ctcccttgga aacgttaact cttatcaggg agggaatgtg

121    gtgattactc aaaggccaca atttataact tcgtggcgcc cgggcattgc tacggtaacc

181    tggaatcagt gtaatggtcc tgggtttgct gatggttcct gggcttacta cagggagtat

241    attgcgtggg tagtattccc caaaaaggtt atgaccaaaa atggatatcc cttatttatt

301    gaggttcata ataaaggtag ctggagtgag gagaatactg gtgacaatga cagctatttt

361    tttctcaagg ggtataagtg ggatgagcgg gcctttgatg caggtaattt gtgtcagaaa

421    ccaggagaaa caacccgtct gactgagaaa tttgacgata ttatttttaa agtcgcccta

481    cctgcagatc ttcctttagg ggattattct gttacaattc catacacttc cggcatgcag

541    cgtcatttcg cgagttactt gggagcccgt tttaaaatcc catacaatgt ggccaaaact

601    ctcccaagag agaatgaaat gttattctta tttaagaata tcggcggatg ccgtccttct

661    gcacagtctc tggaaataaa gcatggtgat ctgtctatta atagcgctaa taatcattat

721    gcggctcaga ctctttctgt gtcttgcgat gtgcctgcaa atattcgttt tatgctgtta

781    agaaatacaa ctccgacata cagccatggt aagaaatttt cggttggtct ggggcatggc
```

-continued

12. Sequence Listing

```
841   tgggactcca ttgtttcggt taacggggtg gacacaggag agacaacgat gagatggtac

901   aaagcaggta cacaaaacct gaccatcggc agtcgcctct atggtgaatc ttcaaagata

961   caaccaggag tactatctgg ttcagcaacg ctgctcatga tattgccata a
```

GenBank Accession No. AY212279.1 (GI: 37786762)
*Escherichia coli* strain APEC 1 PapGII (papGII) gene, complete cds
SEQ ID NO: 22

```
  1   atgaaaaaat ggttccctgc tttgttattt tccttgtgtg tgtctggtga gtcctctgca

 61   tggaataata ttgtctttta ctcccttgga aacgttaact cttatcaggg agggaatgtg

121   gtgattactc aaaggccaca atttataact tcgtggcgcc cgggcattgc tacggtaacc

181   tggaatcagt gtaatggtcc tgggtttgct gatggtttct gggcttacta cagggagtat

241   attgcgtggg tagtattccc caaaaaggtt atgaccaaaa atggatatcc cttatttatt

301   gaggttcata ataaaggtag ctggagtgag gagaatactg gtgacaatga cagctatttt

361   tttctcaagg ggtataagtg ggatgagcgg gcctttgatg caggtaattt gtgtcagaaa

421   ccaggagaaa caacccgtct gactgagaaa tttgacgata ttatttttaa agtcgcccta

481   cctgcagatc ttcctttagg ggattattct gttacaattc catacacttc cggcatgcag

541   cgtcatttcg cgagttactt gggagcccgt tttaaaatcc catacaatgt ggccaaaact

601   ctcccaagag agaatgaaat gttattctta tttaagaata tcggcggatg ccgtccttct

661   gcacagtctc tggaaataaa gcatggtgat ctgtctatta atagcgctaa taatcattat

721   gcggctcaga ctctttctgt gtcttgcgat gtgcctgcaa atattcgttt tatgctgtta

781   agaaatacaa ctccgacata cagccatggt aagaaatttt cggttggtct ggggcatggc

841   tgggactcca ttgtttcggt taacggggtg gacacaggag agacaacgat gagatggtac

901   aaagcaggta cacaaaacct gaccatcggc agtcgcctct atggtgaatc ttcaaagata

961   caaccaggag tactatctgg ttcagcaacg ctgctcatga tattgccata a
```

GenBank Accession No. AY212280.1 (GI: 37786764)
*Escherichia coli* strain APEC 41 PapGII (papGII) gene, complete cds
SEQ ID NO: 23

```
MKKWFPALLFSLCVSGESSAWNNIVFYSLGNVNSYQGGNVVITQRPQFITSWRPGIATVTWNQCNGPGFA
DGSWAYYREYIAWVVFPKKVMTKNGYPLFIEVHNKGSWSEENTGDNDSYFFLKGYKWDERAFDAGNLC
QKPGETTRLTEKFDDIIFKVALPADLPLGDYSVTIPYTSGMQRHFASYLGARFKIPYNVAKTLPRENEML
FLFKNIGGCRPSAQSLEIKHGDLSINSANNHYAAQTLSVSCDVPANIRFMLLRNTTPTYSHGKKFSVGLGH
GWDSIVSVNGVDTGETTMRWYKAGTQNLTIGSRLYGESSKIQPGVLSGSATLLMILP
```

GenBank Accession No. AY212279.1 (GI: 37786762)
*Escherichia coli* strain APEC 1 PapGII (papGII) gene, complete cds
SEQ ID NO: 24

```
MKKWFPALLF SLCVSGESSAWNNIVFYSLGNVNSYQGGNVVITQRPQFITSWRPGIATVTWNQCNGPGFA
DGFWAYYREYIAWVVFPKKVMTKNGYPLFIEVHNKGSWSEENTGDNDSYFFLKGYKWDERAFDAGNLC
QKPGETTRLTEKFDDIIFKVALPADLPLGDYSVTIPYTSGMQRHFASYLGARFKIPYNVAKTLPRENEML
FLFKNIGGCRPSAQSLEIKHGDLSINSANNHYAAQTLSVSCDVPANIRFMLLRNTTPTYSHGKKFSVGLGH
GWDSIVSVNGVDTGETTMRWYKAGTQNLTIGSRLYGESSKIQPGVLSGSATLLMILP
```

GenBank Accession No. AGA03820.1 (GI: 429545215)
FimH [*Escherichia coli*]
SEQ ID NO: 25

```
  1   mkrvitlfav llmgwsvnaw sfacktangt aipigggsan vyvnlapavn vgqnlvvdls

 61   tqifchndyp etitdyvtlq rgsayggvls nfsgtvkysg ssypfpttse tprvvynsrt

121   dkpwpvalyl tpvssaggva ikagsliavl ilrqtnnyns ddfqfvwniy anndvvvptg
```

-continued

12. Sequence Listing

```
181    gcdvsardvt vtlpdypgsv pipltvycak sqnlgyylsg ttadagnsif tntasfspaq

241    gvgvqltrng tiipanntvs lgavgtsays lgltanyart ggqvtagnvk siigvtfvyq
```

GenBank Accession No. YP_001481324.1 (GI: 157418252)
IutA [*Escherichia coli* APEC O1]

SEQ ID NO: 26

```
  1    mmiskkytlw alnpllltmm apavaqqtdd etfvvsanrs nrtvaemaqt twvienaele

 61    qqiqggkelk dalaglipgl dvssrsrtny gmnvrgrplv vlvdgvrins srtdsrqlds

121    idpfnidhie visgatslyg ggstgglini vtkkgqpetm mefeagtksg fssskdhder

181    iagaysggne hisgrlsvay qkfggwfdgn gdatlldntq tglqysdrld imgtgtlnid

241    esrqlqlitq yyksqgdddy glnlgkgfsa irgtstpfvs nglnsdripg terhlislqy

301    sdsaflgqel vgqvyyrdes lrfypfptvn ankqvtafss sqqdtdqygm kltlnskpmd

361    gwqitwglda dherftsnqm ffdlaqasas gglnnkkiyt tgrypsydit nlaaflqsgy

421    dinnlffing gvryqytenk iddfigyaqq rqiaagkats adaipggsvd ydnflfnagl

481    lmhiterqqa wlnfsqgvel pdpgkyygrg iygaavnghl pltksvnvsd sklegvkvds

541    yelgwrftgn nlrtqiaayy sisdksvvan kdltisvvdd krriygvega vdylipdtdw

601    stgvnfnvlk teskvngtwq kydvktasps katayigwap dpwslrvqst tsfdvsdaqg

661    ykvdgyttad llgsyqlpvg tlsfsienlf drdyttvwgq raplyyspgy gpaslydykg

721    rgrtfglnys vlf
```

Leukotoxin-FimH Fusion

SEQ ID NO: 27

```
GAATTCCGGGGGATTATGCGTTAAGCATAAAGTGTAAAGCCTGGGGTGCCTAATGAGTGA
GCTAACTCACATTAATTGCGTTGCGCTCACTGCCCGCTTTCCAGTCGGGAAACCTGTCGT
GCCAGCTGCATTAATGAATCGGCCAACGCGCGGGGAGAGGCGGTTTGCGTATTGGGCGCC
AGGGTGGTTTTTCTTTTCACCAGTGAGACGGGCAACAGCTGATTGCCCTTCACCGCCTGG
CCCTGAGAGAGTTGCAGCAAGCGGTCCACGCTGGTTTGCCCCAGCAGGCGAAAATCCTGT
TTGATGGTGGTTGACGGCGGGATATAACATGAGCTGTCTTCGGTATCGTCGTATCCCACT
ACCGAGATATCCGCACCAACGCGCAGCCCGGACTCGGTAATGGCGCGCATTGCGCCCAGC
GCCATCTGATCGTTGGCAACCAGCATCGCAGTGGGAACGATGCCCTCATTCAGCATTTGC
ATGGTTTGTTGAAAACCGGACATGGCACTCCAGTCGCCTTCCCGTTCCGCTATCGGCTGA
ATTTGATTGCGAGTGAGATATTTATGCCAGCCAGCCAGACGCAGACGCGCCGAGACAGAA
CTTAATGGGCCCGCTAACAGCGCGATTTGCTGGTGACCCAATGCGACCAGATGCTCCACG
CCCAGTCGCGTACCGTCTTCATGGGAGAAAATAATACTGTTGATGGGTGTCTGGTCAGAG
ACATCAAGAAATAACGCCGGAACATTAGTGCAGGCAGCTTCCACAGCAATGGCATCCTGG
TCATCCAGCGGATAGTTAATGATCAGCCCACTGACGCGTTGCGCGAGAAGATTGTGCACC
GCCGCTTTACAGGCTTCGACGCCGCTTCGTTCTACCATCGACACCACCACGCTGGCACCC
AGTTGATCGGCGCGAGATTTAATCGCCGCGACAATTTGCGACGGCGCGTGCAGGGCCAGA
CTGGAGGTGGCAACGCCAATCAGCAACGACTGTTTGCCCGCCAGTTGTTGTGCCACGCGG
TTGGGAATGTAATTCAGCTCCGCCATCGCCGCTTCCACTTTTTCCCGCGTTTTCGCAGAA
ACGTGGCTGGCCTGGTTCACCACGCGGGAAACGGTCTGATAAGAGACACCGGCATACTCT
GCGACATCGTATAACGTTACTGGTTTCACATTCACCACCCTGAATTGACTCTCTTCCGGG
CGCTATCATGCCATACCGCGAAAGGTTTTGCGCCATTCGATGGTGTCAACCTTGCAGAGC
TGCGCCTTTATTATTATCCGCCGGGAGAAAATATTGTGGAGGTTTATCCAATAGGTATTG
GATTGCAGGGGCTGGAAACCCGGTGATGGAAACGCGTGTTGGGCAGAAAATCCCTAACCC
AACCTGGACGCCTACGCAGGCATTCGTCAGCGTTCGCTGGAGGTGCGGATTAAATTACCG
CCAGTCGTTCTGCCGACCAAATAACCCGCTAGACGTTACGCACTGCCTCGTGCATGGTAA
TGGCGAATACCTCATTCATGGTACCAGTGCGCCGGACAGCGTCGGTTTGCGCGTCAGTTC
AGGGTGTATTCGCATGAATGCACCGGATATTAAAGCCTTGTTCTCCAGGTGCGGACGGGA
ACGTGGTGAAAGTGATCAACGAACCGGTAAATATTCCGTGGATCTAACGGGATGCGTTAT
GTTGAAGTGAGACCGGTCGACGCATGCCAGGACAACTTCTGGTCCGGTAACGTGCTGAGC
CCGGCCAAGCTTACTCCCCATCCCCCTGTTGACAATTAATCATCGGCTCGTATAATGTGT
GGAATTGTGAGCGGATAACAATTTCACAGGAAACAGGATCACTAAGGAGGTTTAAATATG
GCTACTGTTATAGATCTAAGCTTCCCAAAAACTGGGGCAAAAAAAATTATCCTCTATATT
CCCCAAAATTACCAATATGATACTGAACAAGGTAATGGTTTACAGGATTTAGTCAAAGCG
GCCGAAGAGTTGGGGATTGAGGTACAAAGAGAAGAACGCAATAATATTGCAACAGCTCAA
ACCAGTTTAGGCACGATTCAAACCGCTATTGGCTTAACTGAGCGTGGCATTGTGTTATCC
GCTCCACAAATTGATAAATTGCTACAGAAAACTAAAGCAGGCCAAGCATTAGGTTCTGCC
GAAAGCATTGTACAAAATGCAAATAAAGCCAAAACTGTATTATCTGGCATTCAATCTATT
TTAGGCTCAGTATTGGCTGGAATGGATTTAGATGAGGCCTTACAGAATAACAGCAACCAA
CATGCTCTTGCTAAAGCTGGCTTGGAGCTAACAAATTCATTAATTGAAAATATTGCTAAT
TCAGTAAAAACACTTGACGAATTTGGTGAGCAAATTAGTCAATTTGGTTCAAAACTACAA
AATATCAAAGGCTTAGGGACTTTAGGAGACAAACTCAAAAATATCGGTGGACTTGATAAA
GCTGGCCTTGGTTTAGATGTTATCTCAGGGCTATTATCGGGCGCAACAGCTGCACTTGTA
```

-continued

| 12. Sequence Listing |
| --- |

```
CTTGCAGATAAAAATGCTTCAACAGCTAAAAAAGTGGGTGCGGGTTTTGAATTGGCAAAC
CAAGTTGTTGGTAATATTACCAAAGCCGTTTCTTCTTACATTTTAGCCCAACGTGTTGCA
GCAGGTTTATCTTCAACTGGGCCTGTGGCTGCTTTAATTGCTTCTACTGTTTCTCTTGCG
ATTAGCCCATTAGCATTTGCCGGTATTGCCGATAAATTTAATCATGCAAAAAGTTTAGAG
AGTTATGCCGAACGCTTTAAAAAATTAGGCTATGACGGAGATAATTTATTAGCAGAATAT
CAGCGGGGAACAGGGACTATTGATGCATCCGTTACTGCAATTAATACCGCATTGGCCGCT
ATTGCTGGTGGTGTGTCTGCTGCTGCAGCCGGCTCGGTTATTGCTTCACCGATTGCCTTA
TTAGTATCTGGGATTACCGGTGTAATTTCTACGATTCTGCAATATTCTAAACAAGCAATG
TTTGAGCACGTTGCAAATAAAATTCATAACAAAATTGTAGAATGGGAAAAAAATAATCAC
GGTAAGAACTACTTTGAAAATGGTTACGATGCCCGTTATCTTGCGAATTTACAAGATAAT
ATGAAATTCTTACTGAACTTAAACAAAGAGTTACAGGCAGAACGTGTCATCGCTATTACT
CAGCAGCAATGGGATAACAACATTGGTGATTTAGCTGGTATTAGCCGTTTAGGTGAAAAA
GTCCTTAGTGGTAAAGCCTATGTGGATGCGTTTGAAGAAGGCAAACACATTAAAGCCGAT
AAATTAGTACAGTTGGATTCGGCAAACGGTATTATTGATGTGAGTAATTCGGGTAAAGCG
AAAACTCAGCATATCTTATTCAGAACGCCATTATTGACGCCGGGAACAGAGCATCGTGAA
CGCGTACAAACAGGTAAATATGAATATATTACCAAGCTCAATATTAACCGTGTAGATAGC
TGGAAAATTACAGATGGTGCAGCAAGTTCTACCTTTGATTTAACTAACGTTGTTCAGCGT
ATTGGTATTGAATTAGAGAATGCTGGAAATGTAACTAAAACCAAAGAAACAAAAATTATT
GCCAAACTTGGTGAAGGTGATGACAACGTATTTGTTGGTTCTGGTACGACGGAAATTGAT
GGCGGTGAAGGTTACGACCGAGTTCACTATAGCcGTGGAAACTATGGTGCTTTAACTATT
GATGCAACCAAAGAGACCGAGCAAGGTAGTTATACCGTAAATCGTTTCGTAGAAACCGGT
AAAGCACTACACGAAGTGACTTCAACCCATACCGCATTAGTGGGCAACCGTGAAGAAAAA
ATAGAATATCGTCATAGCAATAACCAGCACCATGCCGGTTATTACACCAAAGATACCTTG
AAAGCTGTTGAAGAAATTATCGGTACATCACATAACGATATCTTTAAAGGTAGTAAGTTC
AATGATGCCTTTAACGGTGGTGATGGTGTCGATACTATTGACGGTAACGACGGCAATGAC
CGCTTATTTGGTGGTAAAGGCGATGATATTCTCGATGGTGGAAATGGTGATGATTTTATC
GATGGCGGTAAAGGCAACGACCTATTACACGGTGGCAAGGGCGATGATATTTTCGTTCAC
CGTAAAGGCGATGGTAATGATATTATTACCGATTCTGACGGCAATGATAAATTATCATTC
TCTGATTCGAACTTAAAAGATTTAACATTTGAAAAAGTTAAACATAATCTTGTCATCACG
AATAGCAAAAAAGAGAAAGTGACCATTCAAAACTGGTTCCGAGAGGCTGATTTTGCTAAA
GAAGTGCCTAATTATAAAGCAACTAAAGATGAGAAAATCGAAGAAATCATCGGTCAAAAT
GGCGAGCGGATCACCTCAAAGCAAGTTGATGATCTTATCGCAAAAGGTAACGGCAAAATT
ACCCAAGATGAGCTATCAAAAGTTGTTGATAACTATGAATTGCTCAAACATAGCAAAAAT
GTGACAAACAGCTTAGATAAGTTAATCTCATCTGTAAGTGCATTTACCTCGTCTAATGAT
TCGAGAAATGTATTAGTGGCTCCAACTTCAATGTTGGATCAAAGTTTATCTTCTCTTCAA
TTTGCTAGGGGATCXAAACGAGTTATTACGCTGTTTGCTGTACTGCTGATGGGCTGGTCG
GTAAATGCCTGGTCATTCGCCTGTAAAACCGCCAATGGTACCGCAATCCCTATTGGCGGT
GGCAGCGCCAATGTTTATGTAAACCTTGCGCCTGCCGTGAATGTCGGGCAAAAGCTGGTC
GTAGATCTTTCGACGCAAATCTTTTGCCATAACGATTACCCAGAAACCATTACAGACTAT
GTCACACTGCAACGAGGTTCGGCTTATGGCGGCGTGTTATCTAGTTTTTCCGGGACCGTA
AAATATAATGGCAGTAGCTATCCTTTCCCTACTACCAGCGAAACGCCGCGGGTTGTTTAT
AATTCGAGAACGGATAAGCCGTGGCCGGTGGCGCTTTATTTGACGCCGGTGAGCAGTGCG
GGGGGAGTGGCGATTAAAGCTGGCTCATTAATTGCCGTGCTTATTTTGCGACAGACCAAC
AACTATAACAGCGATGATTTCCAGTTTGTGTGGAATATTTACGCCAATAATGATGTGGTG
GTGCCCACTGGCGGCTGCGATGTTTCTGCTCGTGATGTCACCGTTACTCTGCCGGACTAC
CCTGGTTCAGTGCCGATTCCTCTTACCGTTTATTGTGCGAAAAGCCAAAACCTGGGGTAT
TACCTCTCCGGCACAACCGCAGATGCGGGCAACTCGATTTTCACCAATACCGCGTCGTTT
TCACCCGCGCAGGGCGTCGGCGTACAGTTGACGCGCAACGGTACGATTATTCCAGCGAAT
AACACGGTATCGTTAGGAGCAGTAGGGACTTCGGCGGTAAGTCTGGGATTAACGGCAAAT
TACGCACGTACCGGAGGGCAGGTGACTGCAGGGAATGTGCAATCGATTATTGGCGTGACT
TTTGTTTATCAATAACCATGGCATCACAGTATCGTGATGACAGAGGCAGGGAGTGGGACA
AAATTGAAATCAAATAATGATTTTATTTTGACTGATAGTGACCTGTTCGTTGCAACAAAT
TGATAAGCAATGCTTTTTTATAATGCCAACTTAGTATAAAAAAGCTGAACGAGAAACGTA
AAATGATATAAATATCAATATATTAAATTAGATTTTGCATAAAAAACAGACTACATAATA
CTGTAAAACACAACATATGCAGTCACTATGAATCAACTACTTAGATGGTATTAGTGACCT
GTAACAGAGCATTAGCGCAAGGTGATTTTTGTCTTCTTGCGCTAATTTTTTGTCATCAAA
CCTGTCGCACTCCAGAGAAGCACAAAGCCTCGCAATCCAGTGCAAAGCTCTGCCTCGCGC
GTTTCGGTGATGACGGTGAAAACCTCTGACACATGCAGCTCCCGGAGACGGTCACAGCTT
GTCTGTAAGCGGATGCCGGGAGCAGACAAGCCCGTCAGGGCGCGTCAGCGGGTGTTGGCG
GGTGTCGGGGCGCAGCCATGACCCAGTCACGTAGCGATAGCGGAGTGTATACTGGCTTAA
CTATGCGGCATCAGAGCAGATTGTACTGAGAGTGCACCATATGCGGTGTGAAATACCGCA
CAGATGCGTAAGGAGAAAATACCGCATCAGGCGCTCTTCCGCTTCCTGGCTCACTGACTC
GCTGCGCTCGGTCGTTCGGCTGCGGCGAGCGGTATCAGCTCACTCAAAGGCGGTAATACG
GTTATCCACAGAATCAGGGGATAACGCAGGAAAGAACATGTGAGCAAAAGGCCAGCAAAA
GGCCAGGAACCGTAAAAAGGCCGCGTTGCTGGCGTTTTTCCATAGGCTCCGCCCCCCTGA
CGAGCATCACAAAAATCGACGCTCAAGTCAGAGGTGGCGAAACCCGACAGGACTATAAAG
ATACCAGGCGTTTCCCCCTGGAAGCTCCCTCGTGCGCTCTCCTGTTCCGACCCTGCCGCT
TACCGGATACCTGTCCGCCTTTCTCCCTTCGGGAAGCGTGGCGCTTTCTCATAGCTCACG
CTGTAGGTATCTCAGTTCGGTGTAGGTCGTTCGCTCCAAGCTGGGCTGTGTGCACGAACC
CCCCGTTCAGCCCGACCGCTGCGCCTTATCCGGTAACTATCGTCTTGAGTCCAACCCGGT
AAGACACGACTTATCGCCACTGGCAGCAGCCACTGGTAACAGGATTAGCAGAGCGAGGTA
TGTAGGCGGTGCTACAGAGTTCTTGAAGTGGTGGCCTAACTACGGCTACACTAGAAGGAC
AGTATTTGGTATCTGCGCTCTGCTGAAGCCAGTTACCTTCGGAAAAAGAGTTGGTAGCTC
TTGATCCGGCAAACAAACCACCGCTGGTAGCGGTGGTTTTTTTGTTTGCAAGCAGCAGAT
TACGCGCAGAAAAAAAGGATCTCAAGAAGATCCTTTGATCGGGGCTACGGGGTCTGACGC
TCAGTGGAACGAAAACTCACGTTAAGGGATTTTGGTCATGAGATTATCAAAAAGGATCTT
CACCTAGATCCTTTTAAATTAAAAATGAAGTTTTAAATCAATCTAAAGTATATATGAGTA
```

-continued

12. Sequence Listing

AACTTGGTCTGACAGTTACCAATGCTTAATCAGTGAGGCACCTATCTCAGCGATCTGTCT
ATTTCGTTCATCCATAGTTGCCTGACTCCCCGTCGTGTAGATAACTACGATACGGGAGGG
CTTACCATCTGGCCCCAGTGCTGCAATGATACCGCGAGACCCACGCTCACCGGCTCCAGA
TTTATCAGCAATAAACCAGCCAGCCGGAAGGGCCGAGCGCAGAAGTGGTCCTGCAACTTT
ATCCGCCTCCATCCAGTCTATTAATTGTTGCCGGGAAGCTAGAGTAAGTAGTTCGCCAGT
TAATAGTTTGCGCAACGTTGTTGCCATTGCTGCAGGCATCGTGGTGTCACGCTCGTCGTT
TGGTATGGCTTCATTCAGCTCCGGTTCCCAACGATCAAGGCGAGTTACATGATCCCCCAT
GTTGTGCAAAAAAGCGGTTAGCTCCTTCGGTCCTCCGATCGTTGTCAGAAGTAAGTTGGC
CGCAGTGTTATCACTCATGGTTATGGCAGCACTGCATAATTCTCTTACTGTCATGCCATC
CGTAAGATGCTTTTCTGTGACTGGTGAGTACTCAACCAAGTCATTCTGAGAATAGTGTAT
GCGGCGACCGAGTTGCTCTTGCCCGGCGTCAACACGGGATAATACCGCGCCACATAGCAG
AACTTTAAAAGTGCTCATCATTGGAAAACGTTCTTCGGGGCGAAAACTCTCAAGGATCTT
ACCGCTGTTGAGATCCAGTTCGATGTAACCCACTCGTGCACCCAACTGATCTTCAGCATC
TTTTACTTTCACCAGCGTTTCTGGGTGAGCAAAAACAGGAAGGCAAAATGCCGCAAAAAA
GGGAATAAGGGCGACACGGAAATGTTGAATACTCATACTCTTCCTTTTTCAATATTATTG
AAGCATTTATCAGGGTTATTGTCTCATGAGCGGATACATATTTGAATGTATTTAGAAAAA
TAAACAAATAGGGGTTCCGCGCACATTTCCCCGAAAAGTGCCACCTGACGTCTAAGAAAC
CATTATTATCATGACATTAACCTATAAAAATAGGCGTATCACGAGGCCCTTTCGTCTTCA
AGAA

Leukotoxin-PapG Fusion

SEQ ID NO: 28

GAATTCCGGGGGATTATGCGTTAAGCATAAAGTGTAAAGCCTGGGGTGCCTAATGAGTGA
GCTAACTCACATTAATTGCGTTGCGCTCACTGCCCGCTTTCCAGTCGGGAAACCTGTCGT
GCCAGCTGCATTAATGAATCGGCCAACGCGCGGGGAGAGGCGGTTTGCGTATTGGGCGCC
AGGGTGGTTTTTCTTTTCACCAGTGAGACGGGCAACAGCTGATTGCCCTTCACCGCCTGG
CCCTGAGAGAGTTGCAGCAAGCGGTCCACGCTGGTTTGCCCCAGCAGGCGAAAATCCTGT
TTGATGGTGGTTGACGGCGGGATATAACATGAGCTGTCTTCGGTATCGTCGTATCCCACT
ACCGAGATATCCGCACCAACGCGCAGCCCGGACTCGGTAATGGCGCGCATTGCGCCCAGC
GCCATCTGATCGTTGGCAACCAGCATCGCAGTGGGAACGATGCCCTCATTCAGCATTTGC
ATGGTTTGTTGAAAACCGGACATGGCACTCCAGTCGCCTTCCCGTTCCGCTATCGGCTGA
ATTTGATTGCGAGTGAGATATTTATGCCAGCCAGCCAGACGCAGACGCGCCGAGACAGAA
CTTAATGGGCCCGCTAACAGCGCGATTTGCTGGTGACCCAATGCGACCAGATGCTCCACG
CCCAGTCGCGTACCGTCTTCATGGGAGAAAATAATACTGTTGATGGGTGTCTGGTCAGAG
ACATCAAGAAATAACGCCGGAACATTAGTGCAGGCAGCTTCCACAGCAATGGCATCCTGG
TCATCCAGCGGATAGTTAATGATCAGCCCACTGACGCGTTGCGCGAGAAGATTGTGCACC
GCCGCTTTACAGGCTTCGACGCCGCTTCGTTCTACCATCGACACCACCACGCTGGCACCC
AGTTGATCGGCGCGAGATTTAATCGCCGCGACAATTTGCGACGGCGCGTGCAGGGCCAGA
CTGGAGGTGGCAACGCCAATCAGCAACGACTGTTTGCCCGCCAGTTGTTGTGCCACGCGG
TTGGGAATGTAATTCAGCTCCGCCATCGCCGCTTCCACTTTTTCCCGCGTTTTCGCAGAA
ACGTGGCTGGCCTGGTTCACCACGCGGGAAACGGTCTGATAAGAGACACCGGCATACTCT
GCGACATCGTATAACGTTACTGGTTTCACATTCACCACCCTGAATTGACTCTCTTCCGGG
CGCTATCATGCCATACCGCGAAAGGTTTTGCGCCATTCGATGGTGTCAACCTTGCAGAGC
TGCGCCTTTATTATTATCCGCCGGGAGAAAATATTGTGGAGGTTTATCCAATAGGTATTG
GATTGCAGGGGCTGGAAACCCGGTGATGGAAACGCGTGTTGGGCAGAAAATCCCTAACCC
AACCTGGACGCCTACGCAGGCATTCGTCAGCGTTCGCTGGAGGTGCGGATTAAATTACCG
CCAGTCGTTCTGCCGACCAAATAACCCGCTAGACGTTACGCACTGCCTCGTGCATGGTAA
TGGCGAATACCTCATTCATGGTACCAGTGCGCCGGACAGCGTCGGTTTGCGCGTCAGTTC
AGGGTGTATTCGCATGAATGCACCGGATATTAAAGCCTTGTTCTCCAGGTGCGGACGGGA
ACGTGGTGAAAGTGATCAACGAACCGGTAAATATTCCGTGGATCTAACGGGATGCGTTAT
GTTGAAGTGAGACCGGTCGACGCATGCCAGGACAACTTCTGGTCCGGTAACGTGCTGAGC
CCGGCCAAGCTTACTCCCCATCCCCCTGTTGACAATTAATCATCGGCTCGTATAATGTGT
GGAATTGTGAGCGGATAACAATTTCACAGGAAACAGGATCACTAAGGAGGTTTAAATATG
GCTACTGTTATAGATCTAAGCTTCCCAAAAACTGGGGCAAAAAAAATTATCCTCTATATT
CCCCAAAATTACCAATATGATACTGAACAAGGTAATGGTTTACAGGATTTAGTCAAAGCG
GCCGAAGAGTTGGGGATTGAGGTACAAAGAGAAGAACGCAATAATATTGCAACAGCTCAA
ACCAGTTTAGGCACGATTCAAACCGCTATTGGCTTAACTGAGCGTGGCATTGTGTTATCC
GCTCCACAAATTGATAAATTGCTACAGAAAACTAAAGCAGGCCAAGCATTAGGTTCTGCC
GAAAGCATTGTACAAAATGCAAATAAAGCCAAAACTGTATTATCTGGCATTCAATCTATT
TTAGGCTCAGTATTGGCTGGAATGGATTTAGATGAGGCCTTACAGAATAACAGCAACCAA
CATGCTCTTGCTAAAGCTGGCTTGGAGCTAACAAATTCATTAATTGAAAATATTGCTAAT
TCAGTAAAAACACTTGACGAATTTGGTGAGCAAATTAGTCAATTTGGTTCAAAACTACAA
AATATCAAAGGCTTAGGGACTTTAGGAGACAAACTCAAAAATATCGGTGGACTTGATAAA
GCTGGCCTTGGTTTAGATGTTATCTCAGGGCTATTATCGGGCGCAACAGCTGCACTTGTA
CTTGCAGATAAAAATGCTTCAACAGCTAAAAAAGTGGGTGCGGGTTTTGAATTGGCAAAC
CAAGTTGTTGGTAATATTACCAAAGCCGTTTCTTCTTACATTTTAGCCCAACGTGTTGCA
GCAGGTTTATCTTCAACTGGGCCTGTGGCTGCTTTAATTGCTTCTACTGTTTCTCTTGCG
ATTAGCCCATTAGCATTTGCCGGTATTGCCGATAAATTTAATCATGCAAAAAGTTTAGAG
AGTTATGCCGAACGCTTTAAAAAATTAGGCTATGACGGAGATAATTTATTAGCAGAATAT
CAGCGGGGAACAGGGACTATTGATGCATCGGTTACTGCAATTAATACCGCATTGGCCGCT
ATTGCTGGTGGTGTGTCTGCTGCTGCAGCCGGCTCGGTTATTGCTTCACCGATTGCCTTA
TTAGTATCTGGGATTACCGGTGTAATTTCTACGATTCTGCAATATTCTAAACAAGCAATG
TTTGAGCACGTTGCAAATAAAATTCATAACAAAATTGTAGAATGGGAAAAAAATAATCAC
GGTAAGAACTACTTTGAAAATGGTTACGATGCCCGTTATCTTGCGAATTTACAAGATAAT
ATGAAATTCTTACTGAACTTAAACAAAGAGTTACAGGCAGAACGTGTCATCGCTATTACT
CAGCAGCAATGGGATAACAACATTGGTGATTTAGCTGGTATTAGCCGTTTAGGTGAAAAA
GTCCTTAGTGGTAAAGCCTATGTGGATGCGTTTGAAGAAGGCAAACACATTAAAGCCGAT

-continued

12. Sequence Listing

AAATTAGTACAGTTGGATTCGGCAAACGGTATTATTGATGTGAGTAATTCGGGTAAAGCG
AAAACTCAGCATATCTTATTCAGAACGCCATTATTGACGCCGGGAACAGAGCATCGTGAA
CGCGTACAAACAGGTAAATATGAATATATTACCAAGCTCAATATTAACCGTGTAGATAGC
TGGAAAATTACAGATGGTGCAGCAAGTTCTACCTTTGATTTAACTAACGTTGTTCAGCGT
ATTGGTATTGAATTAGACAATGCTGGAAATGTAACTAAAACCAAAGAAACAAAAATTATT
GCCAAACTTGGTGAAGGTGATGACAACGTATTTGTTGGTTCTGGTACGACGGAAATTGAT
GGCGGTGAAGGTTACGACCGAGTTCACTATAGCCGTGGAAACTATGGTGCTTTAACTATT
GATGCAACCAAAGAGACCGAGCAAGGTAGTTATACCGTAAATCGTTTCGTAGAAACCGGT
AAAGCACTACACGAAGTGACTTCAACCCATACCGCATTAGTGGGCAACCGTGAAGAAAAA
ATAGAATATCGTCATAGCAATAACCAGCACCATGCCGGTTATTACACCAAAGATACCTTG
AAAGCTGTTGAAGAAATTATCGGTACATCACATAACGATATCTTTAAAGGTAGTAAGTTC
AATGATGCCTTTAACGGTGGTGATGGTGTCGATACTATTGACGGTAACGACGGCAATGAC
CGCTTATTTGGTGGTAAAGGCGATGATATTCTCGATGGTGGAAATGGTGATGATTTTATC
GATGGCGGTAAAGGCAACGACCTATTACACGGTGGCAAGGGCGATGATATTTTCGTTCAC
CGTAAAGGCGATGGTAATGATATTATTACCGATTCTGACGGCAATGATAAATTATCATTC
TCTGATTCGAACTTAAAAGATTTAACATTTGAAAAAGTTAAACATAATCTTGTCATCACG
AATAGCAAAAAAGAGAAAGTGACCATTCAAAACTGGTTCCGAGAGGCTGATTTTGCTAAA
GAAGTGCCTAATTATAAAGCAACTAAAGATGAGAAAATCGAAGAAATCATCGGTCAAAAT
GGCGAGCGGATCACCTCAAAGCAAGTTGATGATCTTATCGCAAAAGGTAACGGCAAAATT
ACCCAAGATGAGCTATCAAAAGTTGTTGATAACTATGAATTGCTCAAACATAGCAAAAAT
GTGACAAACAGCTTAGATAAGTTAATCTCATCTGTAAGTGCATTTACCTCGTCTAATGAT
TCGAGAAATGTATTAGTGGCTCCAACTTCAATGTTGGATCAAAGTTTATCTTCTCTTCAA
TTTGCTAGGGGATCCAAAAAATGGTTCCCAGCTTTGTTATTTTCCTTGTGTGTGTCTGGT
GAGTCCTCTGCATGGAATAATATTGTCTTTTACTCCCTTGGAAACGTTAACTCTTATCAG
GGAGGGAATGTGGTGATTACTCAAAGGCCACAATTTATAACTTCGTGGCGCCCGGGCATT
GCTACGGTAACCTGGAATCAGTGTAATGGTCCTGGGTTTGCTGATGGTTCCTGGGCTTAC
TACAGGGAGTATATTGCGTGGGTAGTATTCCCCAAAAAGGTTATGACCAAAAATGGATAT
CCCTTATTTATTGAGGTTCATAATAAAGGTAGCTGGAGTGAGGAGAATACTGGTGACAAT
GACAGCTATTTTTTTCTCAAGGGGTATAAGTGGGATGAGCGGGCCTTTGATGCAGGTAAT
TTGTGTCAGAAACCAGGAGAAACAACCCGTCTGACTGAGAAATTTGACGATATTATTTTT
AAAGTCGCCCTACCTGCAGATCTTCCTTTAGGGGATTATTCTGTTACAATTCCATACACT
TCCGGCATGCAGCGTCATTTCGCGAGTTACTTGGGGGCCCGTTTTAAAATCCCATACAAT
GTGGCCAAAACTCTCCCAAGAGAGAATGAAATGTTATTCTTATTTAAGAATATCGGCGGA
TGCCGTCCTTCTGCACAGTCTCTGGAAATAAAGCATGGTGATCTGTCTATTAATAGCGCT
AATAATCATTATGCGGCTCAGACTCTTTCTGTGTCTTGCGATGTGCCTGCAAATATTCGT
TTTATGCTGTTAAGAAATACAACTCCGACATACAGCCATGGTAAGAAATTTTCGGTTGGT
CTGGGGCATGGCTGGGACTCCATTGTTTCGGTTAACGGGGTGGACACAGGAGAGACAACG
ATGAGATGGTACAAAGCAGGTACACAAAACCTGACCATCGGCAGTCGCCTCTATGGTGAA
TCTTCAAAGATACAACCAGGAGTACTATCTGGTTCAGCAACGCTGCTCATGATATTGCCA
TAAGCTAGCCATGGCATCACAGTATCGTGATGACAGAGGCAGGGAGTGGGACAAAATTGA
AATCAAATAATGATTTTATTTTGACTGATAGTGACCTGTTCGTTGCAACAAATTGATAAG
CAATGCTTTTTTATAATGCCAACTTAGTATAAAAAAGCTGAACGAGAAACGTAAAATGAT
ATAAATATCAATATATTAAATTAGATTTTGCATAAAAAACAGACTACATAATACTGTAAA
ACACAACATATGCAGTCACTATGAATCAACTACTTAGATGGTATTAGTGACCTGTAACAG
AGCATTAGCGCAAGGTGATTTTTGTCTTCTTGCGCTAATTTTTTGTCATCAAACCTGTCG
CACTCCAGAGAAGCACAAAGCCTCGCAATCCAGTGCAAAGCTCTGCCTCGCGCGTTTCGG
TGATGACGGTGAAAACCTCTGACACATGCAGCTCCCGGAGACGGTCACAGCTTGTCTGTA
AGCGGATGCCGGGAGCAGACAAGCCCGTCAGGGCGCGTCAGCGGGTGTTGGCGGGTGTCG
GGGCGCAGCCATGACCCAGTCACGTAGCGATAGCGGAGTGTATACTGGCTTAACTATGCG
GCATCAGAGCAGATTGTACTGAGAGTGCACCATATGCGGTGTGAAATACCGCACAGATGC
GTAAGGAGAAAATACCGCATCAGGCGCTCTTCCGCTTCCTGGCTCACTGACTCGCTGCGC
TCGGTCGTTCGGCTGCGGCGAGCGGTATCAGCTCACTCAAAGGCGGTAATACGGTTATCC
ACAGAATCAGGGGATAACGCAGGAAAGAACATGTGAGCAAAAGGCCAGCAAAAGGCCAGG
AACCGTAAAAAGGCCGCGTTGCTGGCGTTTTTCCATAGGCTCCGCCCCCCTGACGAGCAT
CACAAAAATCGACGCTCAAGTCAGAGGTGGCGAAACCCGACAGGACTATAAAGATACCAG
GCGTTTCCCCCTGGAAGCTCCCTCGTGCGCTCTCCTGTTCCGACCCTGCCGCTTACCGGA
TACCTGTCCGCCTTTCTCCCTTCGGGAAGCGTGGCGCTTTCTCATAGCTCACGCTGTAGG
TATCTCAGTTCGGTGTAGGTCGTTCGCTCCAAGCTGGGCTGTGTGCACGAACCCCCCGTT
CAGCCCGACCGCTGCGCCTTATCCGGTAACTATCGTCTTGAGTCCAACCCGGTAAGACAC
GACTTATCGCCACTGGCAGCAGCCACTGGTAACAGGATTAGCAGAGCGAGGTATGTAGGC
GGTGCTACAGAGTTCTTGAAGTGGTGGCCTAACTACGGCTACACTAGAAGGACAGTATTT
GGTATCTGCGCTCTGCTGAAGCCAGTTACCTTCGGAAAAAGAGTTGGTAGCTCTTGATCC
GGCAAACAAACCACCGCTGGTAGCGGTGGTTTTTTTGTTTGCAAGCAGCAGATTACGCGC
AGAAAAAAAGGATCTCAAGAAGATCCTTTGATCGGGGCTACGGGGTCTGACGCTCAGTGG
AACGAAAACTCACGTTAAGGGATTTTGGTCATGAGATTATCAAAAAGGATCTTCACCTAG
ATCCTTTTAAATTAAAAATGAAGTTTTAAATCAATCTAAAGTATATATGAGTAAACTTGG
TCTGACAGTTACCAATGCTTAATCAGTGAGGCACCTATCTCAGCGATCTGTCTATTTCGT
TCATCCATAGTTGCCTGACTCCCCGTCGTGTAGATAACTACGATACGGGAGGGCTTACCA
TCTGGCCCCAGTGCTGCAATGATACCGCGAGACCCACGCTCACCGGCTCCAGATTTATCA
GCAATAAACCAGCCAGCCGGAAGGGCCGAGCGCAGAAGTGGTCCTGCAACTTTATCCGCC
TCCATCCAGTCTATTAATTGTTGCCGGGAAGCTAGAGTAAGTAGTTCGCCAGTTAATAGT
TTGCGCAACGTTGTTGCCATTGCTGCAGGCATCGTGGTGTCACGCTCGTCGTTTGGTATG
GCTTCATTCAGCTCCGGTTCCCAACGATCAAGGCGAGTTACATGATCCCCCATGTTGTGC
AAAAAAGCGGTTAGCTCCTTCGGTCCTCCGATCGTTGTCAGAAGTAAGTTGGCCGCAGTG
TTATCACTCATGGTTATGGCAGCACTGCATAATTCTCTTACTGTCATGCCATCCGTAAGA
TGCTTTTCTGTGACTGGTGAGTACTCAACCAAGTCATTCTGAGAATAGTGTATGCGGCGA
CCGAGTTGCTCTTGCCCGGCGTCAACACGGGATAATACCGCGCCACATAGCAGAACTTTA

12. Sequence Listing

AAAGTGCTCATCATTGGAAAACGTTCTTCGGGGCGAAAACTCTCAAGGATCTTACCGCTG
TTGAGATCCAGTTCGATGTAACCCACTCGTGCACCCAACTGATCTTCAGCATCTTTTACT
TTCACCAGCGTTTCTGGGTGAGCAAAAACAGGAAGGCAAAATGCCGCAAAAAAGGGAATA
AGGGCGACACGGAAATGTTGAATACTCATACTCTTCCTTTTTCAATATTATTGAAGCATT
TATCAGGGTTATTGTCTCATGAGCGGATACATATTTGAATGTATTTAGAAAAATAAACAA
ATAGGGGTTCCGCGCACATTTCCCCGAAAAGTGCCACCTGACGTCTAAGAAACCATTATT
ATCATGACATTAACCTATAAAAATAGGCGTATCACGAGGCCCTTTCGTCTTCAAGAA

Leukotoxin-IutA Fusion

SEQ ID NO: 29

GAATTCCGGGGGATTATGCGTTAAGCATAAAGTGTAAAGCCTGGGGTGCCTAATGAGTGA
GCTAACTCACATTAATTGCGTTGCGCTCACTGCCCGCTTTCCAGTCGGGAAACCTGTCGT
GCCAGCTGCATTAATGAATCGGCCAACGCGCGGGGAGAGGCGGTTTGCGTATTGGGCGCC
AGGGTGGTTTTTCTTTTCACCAGTGAGACGGGCAACAGCTGATTGCCCTTCACCGCCTGG
CCCTGAGAGAGTTGCAGCAAGCGGTCCACGCTGGTTTGCCCCAGCAGGCGAAAATCCTGT
TTGATGGTGGTTGACGGCGGGATATAACATGAGCTGTCTTCGGTATCGTCGTATCCCACT
ACCGAGATATCCGCACCAACGCGCAGCCCGGACTCGGTAATGGCGCGCATTGCGCCCAGC
GCCATCTGATCGTTGGCAACCAGCATCGCAGTGGGAACGATGCCCTCATTCAGCATTTGC
ATGGTTTGTTGAAAACCGGACATGGCACTCCAGTCGCCTTCCCGTTCCGCTATCGGCTGA
ATTTGATTGCGAGTGAGATATTTATGCCAGCCAGCCAGACGCAGACGCGCCGAGACAGAA
CTTAATGGGCCCGCTAACAGCGCGATTTGCTGGTGACCCAATGCGACCAGATGCTCCACG
CCCAGTCGCGTACCGTCTTCATGGGAGAAAATAATACTGTTGATGGGTGTCTGGTCAGAG
ACATCAAGAAATAACGCCGGAACATTAGTGCAGGCAGCTTCCACAGCAATGGCATCCTGG
TCATCCAGCGGATAGTTAATGATCAGCCCACTGACGCGTTGCGCGAGAAGATTGTGCACC
GCCGCTTTACAGGCTTCGACGCCGCTTCGTTCTACCATCGACACCACCACGCTGGCACCC
AGTTGATCGGCGCGAGATTTAATCGCCGCGACAATTTGCGACGGCGCGTGCAGGGCCAGA
CTGGAGGTGGCAACGCCAATCAGCAACGACTGTTTGCCCGCCAGTTGTTGTGCCACGCGG
TTGGGAATGTAATTCAGCTCCGCCATCGCCGCTTCCACTTTTTCCCGCGTTTTCGCAGAA
ACGTGGCTGGCCTGGTTCACCACGCGGGAAACGGTCTGATAAGAGACACCGGCATACTCT
GCGACATCGTATAACGTTACTGGTTTCACATTCACCACCCTGAATTGACTCTCTTCCGGG
CGCTATCATGCCATACCGCGAAAGGTTTTGCGCCATTCGATGGTGTCAACCTTGCAGAGC
TGCGCCTTTATTATTATCCGCCGGGAGAAAATATTGTGGAGGTTTATCCAATAGGTATTG
GATTGCAGGGGCTGGAAACCCGGTGATGGAAACGCGTGTTGGGCAGAAAATCCCTAACCC
AACCTGGACGCCTACGCAGGCATTCGTCAGCGTTCGCTGGAGGTGCGGATTAAATTACCG
CCAGTCGTTCTGCCGACCAAATAACCCGCTAGACGTTACGCACTGCCTCGTGCATGGTAA
TGGCGAATACCTCATTCATGGTACCAGTGCGCCGGACAGCGTCGGTTTGCGCGTCAGTTC
AGGGTGTATTCGCATGAATGCACCGGATATTAAAGCCTTGTTCTCCAGGTGCGGACGGGA
ACGTGGTGAAAGTGATCAACGAACCGGTAAATATTCCGTGGATCTAACGGGATGCGTTAT
GTTGAAGTGAGACCGGTCGACGCATGCCAGGACAACTTCTGGTCCGGTAACGTGCTGAGC
CCGGCCAAGCTTACTCCCCATCCCCCTGTTGACAATTAATCATCGGCTCGTATAATGTGT
GGAATTGTGAGCGGATAACAATTTCACAGGAAACAGGATCACTAAGGAGGTTTAAATATG
GCTACTGTTATAGATCTAAGCTTCCCAAAAACTGGGGCAAAAAAAATTATCCTCTATATT
CCCCAAAATTACCAATATGATACTGAACAAGGTAATGGTTTACAGGATTTAGTCAAAGCG
GCCGAAGAGTTGGGGATTGAGGTACAAAGAGAAGAACGCAATAATATTGCAACAGCTCAA
ACCAGTTTAGGCACGATTCAAACCGCTATTGGCTTAACTGAGCGTGGCATTGTGTTATCC
GCTCCACAAATTGATAAATTGCTACAGAAAACTAAAGCAGGCCAAGCATTAGGTTCTGCC
GAAAGCATTGTACAAAATGCAAATAAAGCCAAAACTGTATTATCTGGCATTCAATCTATT
TTAGGCTCAGTATTGGCTGGAATGGATTTAGATGAGGCCTTACAGAATAACAGCAACCAA
CATGCTCTTGCTAAAGCTGGCTTGGAGCTAACAAATTCATTAATTGAAAATATTGCTAAT
TCAGTAAAAACACTTGACGAATTTGGTGAGCAAATTAGTCAATTTGGTTCAAAACTACAA
AATATCAAAGGCTTAGGGACTTTAGGAGACAAACTCAAAAATATCGGTGGACTTGATAAA
GCTGGCCTTGGTTTAGATGTTATCTCAGGGCTATTATCGGGCGCAACAGCTGCACTTGTA
CTTGCAGATAAAAATGCTTCAACAGCTAAAAAAGTGGGTGCGGGTTTTGAATTGGCAAAC
CAAGTTGTTGGTAATATTACCAAAGCCGTTTCTTCTTACATTTTAGCCCAACGTGTTGCA
GCAGGTTTATCTTCAACTGGGCCTGTGGCTGCTTTAATTGCTTCTACTGTTTCTCTTGCG
ATTAGCCCATTAGCATTTGCCGGTATTGCCGATAAATTTAATCATGCAAAAAGTTTAGAG
AGTTATGCCGAACGCTTTAAAAAATTAGGCTATGACGGAGATAATTTATTAGCAGAATAT
CAGCGGGGAACAGGGACTATTGATGCATCGGTTACTGCAATTAATACCGCATTGGCCGCT
ATTGCTGGTGGTGTGTCTGCTGCTGCAGCCGGCTCGGTTATTGCTTCACCGATTGCCTTA
TTAGTATCTGGGATTACCGGTGTAATTTCTACGATTCTGCAATATTCTAAACAAGCAATG
TTTGAGCACGTTGCAAATAAAATTCATAACAAAATTGTAGAATGGGAAAAAAATAATCAC
GGTAAGAACTACTTTGAAAATGGTTACGATGCCCGTTATCTTGCGAATTTACAAGATAAT
ATGAAATTCTTACTGAACTTAAACAAAGAGTTACAGGCAGAACGTGTCATCGCTATTACT
CAGCAGCAATGGGATAACAACATTGGTGATTTAGCTGGTATTAGCCGTTTAGGTGAAAAA
GTCCTTAGTGGTAAAGCCTATGTGGATGCGTTTGAAGAAGGCAAACACATTAAAGCCGAT
AAATTAGTACAGTTGGATTCGGCAAACGGTATTATTGATGTGAGTAATTCGGGTAAAGCG
AAAACTCAGCATATCTTATTCAGAACGCCATTATTGACGCCGGGAACAGAGCATCGTGAA
CGCGTACAAACAGGTAAATATGAATATATTACCAAGCTCAATATTAACCGTGTAGATAGC
TGGAAAATTACAGATGGTGCAGCAAGTTCTACCTTTGATTTAACTAACGTTGTTCAGCGT
ATTGGTATTGAATTAGACAATGCTGGAAATGTAACTAAAACCAAAGAAACAAAAATTATT
GCCAAACTTGGTGAAGGTGATGACAACGTATTTGTTGGTTCTGGTACGACGGAAATTGAT
GGCGGTGAAGGTTACGACCGAGTTCACTATAGCCGTGGAAACTATGGTGCTTTAACTATT
GATGCAACCAAAGAGACCGAGCAAGGTAGTTATACCGTAAATCGTTTCGTAGAAACCGGT
AAAGCACTACACGAAGTGACTTCAACCCATACCGCATTAGTGGGCAACCGTGAAGAAAAA
ATAGAATATCGTCATAGCAATAACCAGCACCATGCCGGTTATTACACCAAAGATACCTTG
AAAGCTGTTGAAGAAATTATCGGTACATCACATAACGATATCTTTAAAGGTAGTAAGTTC
AATGATGCCTTTAACGGTGGTGATGGTGTCGATACTATTGACGGTAACGACGGCAATGAC

-continued

12. Sequence Listing

CGCTTATTTGGTGGTAAAGGCGATGATATTCTCGATGGTGGAAATGGTGATGATTTTATC
GATGGCGGTAAAGGCAACGACCTATTACACGGTGGCAAGGGCGATGATATTTTCGTTCAC
CGTAAAGGCGATGGTAATGATATTATTACCGATTCTGACGGCAATGATAAATTATCATTC
TCTGATTCGAACTTAAAAGATTTAACATTTGAAAAAGTTAAACATAATCTTGTCATCACG
AATAGCAAAAAAGAGAAAGTGACCATTCAAAACTGGTTCCGAGAGGCTGATTTTGCTAAA
GAAGTGCCTAATTATAAAGCAACTAAAGATGAGAAAATCGAAGAAATCATCGGTCAAAAT
GGCGAGCGGATCACCTCAAAGCAAGTTGATGATCTTATCGCAAAAGGTAACGGCAAAATT
ACCCAAGATGAGCTATCAAAAGTTGTTGATAACTATGAATTGCTCAAACATAGCAAAAAT
GTGACAAACAGCTTAGATAAGTTAATCTCATCTGTAAGTGCATTTACCTCGTCTAATGAT
TCGAGAAATGTATTAGTGGCTCCAACTTCAATGTTGGATCAAAGTTTATCTTCTCTTCAA
TTTGCTAGGGGATCCATAAGCAAAAAGTATACGCTTTGGGCTCTCAACCCACTGCTTCTT
ACCATGATGGCGCCAGCAGTCGCTCAACAAACCGATGATGAAACGTTCGTGGTGTCTGCC
AACCGCAGCAATCGCACCGTAGCGGAGATGGCGCAAACCACCTGGGTTATCGAAAACGCC
GAACTGGAACAGCAGATTCAGGGCGGCAAAGAGCTTAAAGACGCACTGGCTCAGCTGATC
CCTGGCCTTGACGTCAGCAGCCGGAGCCGCACCAACTACGGTATGAATGTGCGTGGCCGC
CCGCTGGTCGTGCTGGTTGACGGCGTGCGTCTCAACTCTTCACGTACCGACAGCCGACAA
CTGGACTCTATAGATCCTTTTAATATGCACCATATTGAAGTGATCTTCGGTGCGACGTCC
CTGTACGGCGGCGGCAGTACCGGTGGCCTGATCAACATCGTGACCAAAAAAGGCCAGCCG
GAAACCATGATGGAGTTTGAGGCTGGCACCAAAAGTGGCTTTAGCAGCAGTAAAGATCAC
GATGAACGCATTGCCGGAGCTGTCTCCGGCGGAAATGAGCATATCTCCGGACGTCTTTCC
GTGGCATATCAGAAATTTGGCGGCTGGTTTGACGGTAACGGCGATGCCACCTTGCTTGAT
AACACCCAGACCGGCCTGCAGTACTCCGATCGGCTGGACATCATGGGAACTGGTACGCTG
AACATCGATGAATCCCGGCAGCTTCAGTTGATCACACAGTACTATAAAAGCCAGGGCGAC
GACGATTACGGGCTTAATCTCGGGAAAGGCTTCTCTGCCATCAGAGGGACCAGCACGCCA
TTCGTCAGTAACGGGCTGAATTCCGACCGTATTCCCGGCACTGACGGGCATTTGATCAGC
CTGCAGTACTCTGACAGCGCTTTTCTGGGACAGGAGCTGGTCGGTCAGGTTTACTACCGC
GATGAGTCGTTGCGATTCTACCCGTTCCCGACGGTAAATGCGAACAAACAGGTGACGGCT
TTCTCTTCGTCACAGCAGGACACCGACCAGTACCGCATGAAACTGACTCTGAACAGCAAA
CCGATGGACGGCTGGCAAATCACCTGGGGGCTGGATGCTGATCATGAGCGCTTTACCTCC
AACCAGATGTTCTTCGACCTGGCTCAGGCAAGCGCTTCCGGAGGGCTGAACAACAAGAAG
ATTTACACCACCGGGCGCTATCCGTCGTATGACATCACCAACCTGGCGGCCTTCCTGCAA
TCAGGCTATGACATCAATAATCTCTTTACCCTCAACGGTGGCGTACGCTATCAGTACACT
GAAAACAAGATTGATGATTTCATCGGCTACGCGCAGCAACGGCAGATTGGCGCCGGGAAG
GCTACATCCGCCGACGCATTCTGGCGGCTCAGTCGATTACGACACTTCCTGTTCAACGCC
GGTCTGCTGATGCACATCACCGAACCGCAGCAGGCATGGCTCAACTTCTCCCAGGGCCTG
GAGCTGCCGGACCCGGGTAAATACTATGGTCGCGGCATCTATGGTGCTGCAGTGAACGGC
CATCTTCCTCTAACAAAGAGTGTGAACGTCAGCGACAGCAAGCTGGAAGGCGTGAAAGTC
GATTCTTATGAGCTGGGCTGGCGCTTTACTCGCAATAATCTGCGTACCCAAATCGCGGCC
TACTATTCGATTTCTGATAAGAGCGTGGTGGCGAATAAAGATCTGACCATCAGCGTGGTG
GACGACAAACGCCGTATTTACGGCGTGGAAGGTGCGGTGGACTACCTGATTCCTGATACT
GACTGGAGTACCGGAGTGAACTTCAACGTGCTGAAAACTGAGTCGAAAGTGAACGGTACC
TGGCAGAAATACGATGTGAAGACAGCAAGCCCATCAAAAGCGACAGCCTACATTGGCTGG
GCACCGGACCCGTGGAGTCTGCGCGTGCAGAGCACCACCTCCTTTGACGTGAGCGACGCG
CAGGGCTACAAGGTCGATGGCTATACCACCGTGGATCTGCTCGGCAGTTATCAGCTTCCG
GTGGGTACACTCAGCTTCAGCATTGAAAACCTCTTCGACCGTGACTACACCACTGTCTGG
GGGCAGCGTGCACCACTGTACTACAGCCCGGGTTACGGCCCAGCGTCACTGTACGACTAC
AAAGGCAGGGGCCGAACCTTTGGTCTGAACTACTCTGTGCTGTTCTGACCATGGCATCAC
AGTATCGTGATGACAGAGGCAGGGAGTGGGACAAAATTGAAATCAAATAATGATTTTATT
TTGACTGATAGTGACCTGTTCGTTGCAACAAATTGATAAGCAATGCTTTTTTATAATGCC
AACTTAGTATAAAAAAGCTGAACGAGAAACGTAAAATGATATAAATATCAATATATTAAA
TTAGATTTTGCATAAAAAACAGACTACATAATACTGTAAAACACAACATATGCAGTCACT
ATGAATCAACTACTTAGATGGTATTAGTGACCTGTAACAGAGCATTAGCGCAAGGTGATT
TTTGTCTTCTTGCGCTAATTTTTTGTCATCAAACCTGTCGCACTCCAGAGAAGCACAAAG
CCTCGCAATCCAGTGCAAAGCTCTGCCTCGCGCGTTTCGGTGATGACGGTGAAAACCTCT
GACACATGCAGCTCCCGGAGACGGTCACAGCTTGTCTGTAAGCGGATGCCGGGAGCAGAC
AAGCCCGTCAGGGCGCGTCAGCGGGTGTTGGCGGGTGTCGGGGCGCAGCCATGACCCAGT
CACGTAGCGATAGCGGAGTGTATACTGGCTTAACTATGCGGCATCAGAGCAGATTGTACT
GAGAGTGCACTATATGCGGTGTGAAATACCGCACAGATGCGTAAGGAGAAAATACCGCAT
CAGGCGCTCTTCCGCTTCCTGGCTCACTGACTCGCTGCGCTCGGTCGTTCGGCTGCGGCG
AGCGGTATCAGCTCACTCAAAGGCGGTAATACGGTTATCCACAGAATCAGGGGATAACGC
AGGAAAGAACATGTGAGCAAAAGGCCAGCAAAAGGCCAGGAACCGTAAAAAGGCCGCGTT
GCTGGCGTTTTTCCATAGGCTCCGCCCCCCTGACGAGCATCACAAAAATCGACGCTCAAG
TCAGAGGTGGCGAAACCCGACAGGACTATAAAGATACCAGGCGTTTCCCCCTGGAAGCTC
CCTCGTGCGCTCTCCTGTTCCGACCCTGCCGCTTACCGGATACCTGTCCGCCTTTCTCCC
TTCGGGAAGCGTGGCGCTTTCTCATAGCTCACGCTGTAGGTATCTCAGTTCGGTGTAGGT
CGTTCGCTCCAAGCTGGGCTGTGTGCACGAACCCCCCGTTCAGCCCGACCGCTGCGCCTT
ATCCGGTAACTATCGTCTTGAGTCCAACCCGGTAAGACACGACTTATCGCCACTGGCAGC
AGCCACTGGTAACAGGATTAGCAGAGCGAGGTATGTAGGCGGTGCTACAGAGTTCTTGAA
GTGGTGGCCTAACTACGGCTACACTAGAAGGACAGTATTTGGTATCTGCGCTCTGCTGAA
GCCAGTTACCTTCGGAAAAAGAGTTGGTAGCTCTTGATCCGGCAAACAAACCACCGCTGG
TAGCGGTGGTTTTTTTGTTTGCAAGCAGCAGATTACGCGCAGAAAAAAAGGATCTCAAGA
AGATCCTTTGATCGGGGCTACGGGGTCTGACGCTCAGTGGAACGAAAACTCACGTTAAGG
GATTTTGGTCATGAGATTATCAAAAAGGATCTTCACCTAGATCCTTTTAAATTAAAAATG
AAGTTTTAAATCAATCTAAAGTATATATGAGTAAACTTGGTCTGACAGTTACCAATGCTT
AATCAGTGAGGCACCTATCTCAGCGATCTGTCTATTTCGTTCATCCATAGTTGCCTGACT
CCCCGTCGTGTAGATAACTACGATACGGGAGGGCTTACCATCTGGCCCCAGTGCTGCAAT
GATACCGCGAGACCCACGCTCACCGGCTCCAGATTTATCAGCAATAAACCAGCCAGCCGG

-continued

| 12. Sequence Listing |
| --- |
| AAGGGCCGAGCGCAGAAGTGGTCCTGCAACTTTATCCGCCTCCATCCAGTCTATTAATTG<br>TTGCCGGGAAGCTAGAGTAAGTAGTTCGCCAGTTAATAGTTTGCGCAACGTTGTTGCCAT<br>TGCTGCAGGCATCGTGGTGTCACGCTCGTCGTTTGGTATGGCTTCATTCAGCTCCGGTTC<br>CCAACGATCAAGGCGAGTTACATGATCCCCCATGTTGTGCAAAAAAGCGGTTAGCTCCTT<br>CGGTCCTCCGATCGTTGTCAGAAGTAAGTTGGCCGCAGTGTTATCACTCATGGTTATGGC<br>AGCACTGCATAATTCTCTTACTGTCATGCCATCCGTAAGATGCTTTTCTGTGACTGGTGA<br>GTACTCAACCAAGTCATTCTGAGAATAGTGTATGCGGCGACCGAGTTGCTCTTGCCCGGC<br>GTCAACACGGGATAATACCGCGCCACATAGCAGAACTTTAAAAGTGCTCATCATTGGAAA<br>ACGTTCTTCGGGGCGAAAACTCTCAAGGATCTTACCGCTGTTGAGATCCAGTTCGATGTA<br>ACCCACTCGTGCACCCAACTGATCTTCAGCATCTTTTACTTTCACCAGCGTTTCTGGGTG<br>AGCAAAAACAGGAAGGCAAAATGCCGCAAAAAAGGGAATAAGGGCGACACGGAAATGTTG<br>AATACTCATACTCTTCCTTTTTCAATATTATTGAAGCATTTATCAGGGTTATTGTCTCAT<br>GAGCGGATACATATTTGAATGTATTTAGAAAAATAAACAAATAGGGGTTCCGCGCACATT<br>TCCCCGAAAAGTGCCACCTGACGTCTAAGAAACCATTATTATCATGACATTAACCTATAA<br>AAATAGGCGTATCACGAGGCCCTTTCGTCTTCAAGAA |

What is claimed is:

1. A composition comprising leukotoxin A set forth as SEQ.ID.NO:19 or SEQ.ID.NO: 20 and an immunogenic portion of at least two isolated proteins selected from the group consisting of: Pap fimbrial adhesin PapG protein set forth as SEQ ID NO: 4, SEQ ID NO: 23, or SEQ ID NO: 24 or 80% sequence identity with the PapG protein of SEQ ID NO: 4, SEQ ID NO: 23, or SEQ ID NO: 24, Type 1 fimbrial adhesin FimH protein set forth as SEQ ID NO: 2 or SEQ ID NO: 25 or 80% sequence identity with the FimH protein of SEQ ID NO: 2, SEQ ID NO: 25 and ferric aerobactin receptor lutA protein set forth as SEQ ID NO: 6 or SEQ ID NO: 26, or 80% sequence identity with the lutA protein of SEQ ID NO: 6 or SEQ ID NO: 26 , wherein the immunogenic portion comprises at least 20 amino acid of SEQ ID NO: 4, SEQ ID NO: 23, SEQ ID NO: 24, SEQ ID NO: 2, SEQ ID NO: 25, SEQ ID NO: 6 or SEQ ID NO: 26 wherein the leukotoxin A is fused or conjugated to the immunogenic portion of PapG, FimH, and/or lutA.

2. The composition of claim 1, further comprising an adjuvant.

3. The composition of claim 2, wherein the adjuvant is selected from chitosan, an oil emulsion, a toxin, an aluminum salt, alum, a mineral oil, squalane, thimerosal, interleukin-1, interleukin-2, interleukin-12, Freund's complete adjuvant, Freund's incomplete adjuvant, a polymer, and CpG.

4. The composition of claim 1, further comprising at least one pharmaceutically acceptable excipient.

5. A kit comprising the composition of claim 1, and instructions for administration of the composition to a subject.

* * * * *